US009839450B2

(12) United States Patent
Blain et al.

(10) Patent No.: US 9,839,450 B2
(45) Date of Patent: Dec. 12, 2017

(54) DEVICE AND METHOD FOR REINFORCEMENT OF A FACET

(71) Applicant: SPINAL ELEMENTS, INC., Carlsbad, CA (US)

(72) Inventors: Jason Blain, Encinitas, CA (US); Christopher Newton, San Diego, CA (US); Gregory Martin, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 106 days.

(21) Appl. No.: 14/274,575

(22) Filed: May 9, 2014

(65) Prior Publication Data
US 2015/0094766 A1 Apr. 2, 2015

Related U.S. Application Data

(60) Provisional application No. 61/883,960, filed on Sep. 27, 2013.

(51) Int. Cl.
*A61B 17/70* (2006.01)
*A61B 17/82* (2006.01)

(52) U.S. Cl.
CPC .......... *A61B 17/7064* (2013.01); *A61B 17/82* (2013.01)

(58) Field of Classification Search
CPC .............................. A61B 17/7064; A61B 17/82
See application file for complete search history.

(56) References Cited

U.S. PATENT DOCUMENTS

| 86,016 | A | 1/1869 | Howell |
|---|---|---|---|
| 1,630,239 | A | 5/1927 | Binkley et al. |
| 1,822,280 | A | 9/1931 | Ervay |
| 1,822,330 | A | 9/1931 | Anslie |
| 2,486,303 | A | 10/1949 | Longfellow |
| 2,706,023 | A | 4/1955 | Merritt |
| 2,967,282 | A | 1/1961 | Schwartz et al. |
| 3,111,945 | A | 11/1963 | Von Solbrig |
| 3,149,808 | A | 9/1964 | Weckesser |

(Continued)

FOREIGN PATENT DOCUMENTS

| CA | 2 437 575 | 4/2009 |
|---|---|---|
| DE | 93 04 368 | 5/1993 |

(Continued)

OTHER PUBLICATIONS

Official Communication in European Application No. 14177951.2, dated Nov. 13, 2014.

(Continued)

*Primary Examiner* — Ellen C Hammond
(74) *Attorney, Agent, or Firm* — Knobbe, Martens, Olson & Bear, LLP

(57) ABSTRACT

In some embodiments, a device for reinforcement of a facet joint is provided. The device comprises a lumen configured to receive a fastener member. In some embodiments, a second segment comprises a second lumen configured to receive a fastener member or fastener. In some embodiments, kits are provided with a fastener member and a facet reinforcement device. Methods are also provided for treating a spine. In some embodiments, the fastener member is placed through both articular processes of a facet joint and a facet reinforcement device.

19 Claims, 70 Drawing Sheets

(56) References Cited

U.S. PATENT DOCUMENTS

| | | |
|---|---|---|
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,573,458 A | 3/1986 | Lower |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,959,065 A | 9/1990 | Arnett et al. |
| 4,969,909 A * | 11/1990 | Barouk .................. A61B 17/72 606/62 |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,330,479 A | 7/1994 | Whitmore |
| 5,360,431 A | 11/1994 | Puno et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A | 7/1999 | Whelan |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |

(56) References Cited

U.S. PATENT DOCUMENTS

| | | | |
|---|---|---|---|
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gi, II et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,470,207 B1 | 10/2002 | Simon et al. |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,195 B2 | 12/2003 | Peters et al. |
| 6,669,697 B1 | 12/2003 | Pisharodi |
| 6,669,729 B2 | 12/2003 | Chin |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| D517,404 S | 3/2006 | Schluter |
| 7,008,429 B2 | 3/2006 | Golobek |
| 7,013,675 B2 * | 3/2006 | Marquez-Pickering A44C 7/003 63/1.11 |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Soboleski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,192,468 B2 | 6/2012 | Biedermann et al. |
| 8,216,275 B2 | 7/2012 | Fielding et al. |
| 8,246,655 B2 | 8/2012 | Jackson et al. |
| 8,292,954 B2 * | 10/2012 | Robinson .................. A61F 2/30 623/14.12 |
| 8,306,307 B2 | 11/2012 | Koike et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,753,345 B2 * | 6/2014 | McCormack ........ A61B 17/025 606/79 |
| 8,784,423 B2 | 7/2014 | Kowarsch et al. |
| 8,858,597 B2 | 10/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| D790,062 S | 6/2017 | Blain et al. |
| 9,675,387 B2 | 6/2017 | Blain |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |

(56) References Cited

U.S. PATENT DOCUMENTS

| | | |
|---|---|---|
| 2003/0040797 A1 | 2/2003 | Fallin et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serh an et al. |
| 2005/0059972 A1 | 3/2005 | Biscup |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0159746 A1 | 7/2005 | Grab et al. |
| 2005/0197700 A1 | 9/2005 | Boehem et al. |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1* | 1/2006 | Alamin ............... A61B 17/842 606/74 |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149375 A1 | 7/2006 | Yuan et al. |
| 2006/0200137 A1 | 9/2006 | Soboleski et al. |
| 2006/0241601 A1 | 10/2006 | Trautwein et al. |
| 2006/0241758 A1 | 10/2006 | Peterman et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0078464 A1 | 4/2007 | Jones et al. |
| 2007/0118218 A1 | 5/2007 | Hooper |
| 2007/0123863 A1 | 5/2007 | Winslow et al. |
| 2007/0149976 A1 | 6/2007 | Hale et al. |
| 2007/0179619 A1 | 8/2007 | Grab |
| 2007/0250166 A1 | 10/2007 | McKay |
| 2007/0270812 A1 | 11/2007 | Peckham |
| 2008/0009866 A1 | 1/2008 | Alamin et al. |
| 2008/0058929 A1 | 3/2008 | Whelan |
| 2008/0177264 A1 | 7/2008 | Alamin et al. |
| 2008/0183211 A1 | 7/2008 | Lamborne et al. |
| 2008/0228225 A1 | 9/2008 | Trautwein et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0076617 A1 | 3/2009 | Ralph et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0326589 A1 | 12/2009 | Lemoine et al. |
| 2010/0010548 A1 | 1/2010 | Hermida Ochoa |
| 2010/0076503 A1 | 3/2010 | Beyar et al. |
| 2010/0131008 A1 | 5/2010 | Overes et al. |
| 2010/0179553 A1 | 7/2010 | Ralph et al. |
| 2010/0185241 A1 | 7/2010 | Malandain et al. |
| 2010/0191286 A1* | 7/2010 | Butler ............... A61B 17/7064 606/247 |
| 2010/0204700 A1 | 8/2010 | Falahee |
| 2010/0204732 A1 | 8/2010 | Aschmann et al. |
| 2010/0234894 A1 | 9/2010 | Alamin et al. |
| 2010/0274289 A1 | 10/2010 | Carls et al. |
| 2010/0298829 A1 | 11/2010 | Schaller et al. |
| 2010/0318133 A1 | 12/2010 | Tornier |
| 2011/0022089 A1 | 1/2011 | Assell et al. |
| 2011/0040301 A1 | 2/2011 | Blain et al. |
| 2011/0098816 A1 | 4/2011 | Jacob et al. |
| 2011/0160772 A1 | 6/2011 | Arcenio et al. |
| 2011/0172712 A1 | 7/2011 | Chee et al. |
| 2011/0224790 A1* | 9/2011 | Robinson ............... A61F 2/4606 623/14.12 |
| 2011/0295318 A1 | 12/2011 | Alamin et al. |
| 2011/0313456 A1 | 12/2011 | Blain |
| 2012/0035658 A1 | 2/2012 | Goble et al. |
| 2012/0046749 A1 | 2/2012 | Tatsumi |
| 2012/0101502 A1* | 4/2012 | Kartalian ............... A61B 17/68 606/74 |
| 2012/0150231 A1 | 6/2012 | Alamin et al. |
| 2012/0221048 A1* | 8/2012 | Blain ............... A61B 17/82 606/247 |
| 2012/0221049 A1 | 8/2012 | Blain |
| 2012/0221060 A1* | 8/2012 | Blain ............... A61B 17/82 606/279 |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2012/0310244 A1 | 12/2012 | Blain et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0253649 A1* | 9/2013 | Davis ............... A61B 17/1615 623/17.16 |
| 2013/0325065 A1 | 12/2013 | Malandain et al. |
| 2014/0012318 A1 | 1/2014 | Goel |
| 2014/0066758 A1 | 3/2014 | Marik et al. |
| 2014/0228883 A1 | 8/2014 | Blain |
| 2014/0257397 A1 | 9/2014 | Akbarnia et al. |
| 2014/0277142 A1 | 9/2014 | Blain |
| 2014/0277148 A1 | 9/2014 | Blain |
| 2014/0277149 A1 | 9/2014 | Rooney et al. |
| 2014/0336653 A1 | 11/2014 | Bromer |
| 2014/0378976 A1 | 12/2014 | Garcia |
| 2015/0081023 A1 | 3/2015 | Blain |
| 2015/0094767 A1 | 4/2015 | Blain et al. |
| 2015/0119988 A1* | 4/2015 | Assell ............... A61F 2/4405 623/17.11 |
| 2015/0164516 A1 | 6/2015 | Blain et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0209096 A1 | 7/2015 | Gephart |
| 2015/0257770 A1 | 9/2015 | Assell et al. |
| 2015/0257773 A1 | 9/2015 | Blain |
| 2015/0327872 A1 | 11/2015 | Assell et al. |

(56) References Cited

U.S. PATENT DOCUMENTS

| | | |
|---|---|---|
| 2016/0051294 A1 | 2/2016 | Blain |
| 2016/0113692 A1 | 4/2016 | Knoepfle |
| 2016/0128739 A1 | 5/2016 | Blain et al. |
| 2016/0128838 A1 | 5/2016 | Assell et al. |
| 2016/0213481 A1 | 7/2016 | Blain |
| 2016/0324549 A1 | 11/2016 | Blain |
| 2017/0000527 A1 | 1/2017 | Blain et al. |
| 2017/0105767 A1 | 4/2017 | Blain |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |
| EP | 1 201 256 | 5/2002 |
| EP | 2 919 717 | 9/2015 |
| FR | 2 704 745 | 11/1994 |
| FR | 2 722 980 | 2/1996 |
| GB | 2 366 736 | 3/2002 |
| JP | 62-270147 | 11/1987 |
| JP | 08-509918 | 10/1996 |
| JP | 10-179622 | 7/1998 |
| JP | 2000-210297 | 8/2000 |
| JP | 2004-508888 | 3/2004 |
| JP | 2004-181236 | 7/2004 |
| JP | 2007-503884 | 3/2007 |
| JP | 2007-517627 | 7/2007 |
| JP | 2007-190389 | 8/2007 |
| JP | 2007-521881 | 8/2007 |
| JP | 2008-510526 | 4/2008 |
| JP | 2009-533167 | 9/2009 |
| JP | 2013-534451 | 9/2013 |
| MX | 6012309 | 1/2007 |
| WO | WO 93/14721 | 8/1993 |
| WO | WO 94/04088 | 3/1994 |
| WO | WO 97/47246 | 12/1997 |
| WO | WO 98/48717 | 11/1998 |
| WO | WO 99/23963 | 5/1999 |
| WO | WO 00/38582 | 7/2000 |
| WO | WO 00/53126 | 9/2000 |
| WO | WO 01/30248 | 5/2001 |
| WO | WO 02/45765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2008/008522 | 1/2008 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2013/022880 | 2/2013 |
| WO | WO 2013/138655 | 9/2013 |
| WO | WO 2014/078541 | 5/2014 |
| WO | WO 2016/044432 | 3/2016 |

OTHER PUBLICATIONS

Official Communication in European Application No. 11818586.7, dated Nov. 6, 2014.
International Search Report and Written Opinion in International Application No. PCT/US2014/056598, dated Dec. 29, 2014.
Notice of Acceptance in Australian Application No. AU2013237744, dated Apr. 23, 2015.
Official Communication in Canadian Application No. 2,803,783, dated Aug. 5, 2015.
Official Communication in European Application No. 14175088.5, dated Nov. 18, 2015.
Official Communication in Japanese Application No. 2012-272106, dated Feb. 23, 2015.
Official Communication in Japanese Application No. 2012-272106, dated Nov. 2, 2015.
Official Communication in Japanese Application No. 2013-524882, dated Mar. 2, 2015.
Official Communication in Japanese Application No. 2013-524882, dated Nov. 16, 2015.
Official Communication in Australian Application No. AU2012222229, dated Aug. 21, 2015.
Official Communication in Australian Application No. AU2012222230, dated Aug. 21, 2015.
Official Communication in Japanese Application No. JP 2013-555591, dated Jan. 4, 2016.
Official Communication in Japanese Application No. JP 2013-555592, dated Dec. 7, 2015.
International Search Report and Written Opinion in International Application No. PCT/US2014/019302, dated May 18, 2015.
International Preliminary Report on Patentability and Written Opinion in International Application No. PCT/US2014/019325, dated Sep. 24, 2015.
International Search Report and Written Opinion in International Application No. PCT/US2015/050441, dated Dec. 28, 2015.
3rd Party Lab Notebook, "Facet Cartilage Repair," dated May 20, 2003 in 2 pages.
ArthroTek, "CurvTek® Bone Tunneling System," Surgical Technique, 2000, pp. 6.
E-mail from 3rd Party citing U.S. Appl. No. 60/721,909; U.S. Appl. No. 60/750,005 and U.S. Appl. No. 60/749,000, initial e-mail dated May 11, 2009, reply e-mail dated May 18, 2009.
King et al., "Mechanism of Spinal Injury Due to Caudocephalad Acceleration," Symposium on the Lumbar Spine, Orthopedic Clinic of North America, Jan. 1975, vol. 6, pp. 19-31.
Parteq Innovations, "Facet Joint Implants & Resurfacing Devices," Technology Opportunity Bulletin, Tech ID 1999-012, Queen's University, Ontario Canada.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Official Communication in Canadian Application No. 2,555,355, dated Sep. 2, 2011.
Official Communication in Canadian Application No. 2,803,783, dated Sep. 29, 2014.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.

(56) References Cited

OTHER PUBLICATIONS

Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
International Search Report and Written Opinion in International Application No. PCT/US2011/047432, dated Dec. 12, 2011.
International Preliminary Report on Patentability in International Application No. PCT/US2011/047432, dated Feb. 28, 2013.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 20, 2014.
International Search Report and Written Opinion in International Application No. PCT/US2014/019325, dated Jun. 17, 2014.
International Search Report in International Application No. PCT/CA2002/000193 filed Feb. 15, 2002, dated Jun. 18, 2002.
International Preliminary Report on Patentability in International Application No. PCT/US2004/028094, dated Aug. 27, 2004.
International Search Report in International Application No. PCT/US2004/028094, dated Aug. 27, 2004.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Official Communication in Australian Application No. AU2015205875, dated Apr. 2, 2016.
Official Communication in Canadian Application No. 2,803,783, dated Jul. 7, 2016.
Official Communication in Australian Application No. AU2012222229, dated May 11, 2016.
International Preliminary Report on Patentability and Written Opinion in International Application No. PCT/US2014/056598, dated Apr. 7, 2016.
International Search Report and Written Opinion in International Application No. PCT/US2016/013062, dated Mar. 16, 2016.
ArthroTek, "CurvTek® Bone Tunneling System," User's Manual, 2000, pp. 20.
Beaman, MD et al., "Substance P Innervation of Lumbar Spine Facet Joints", SPINE, 1993, vol. 18, No. 8, pp. 1044-1049.

Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
Frost, Harold M., "From Wolff's Law to the Utah Paradigm: Insights About Bone Physiology and Its Clinical Applications", The Anatomical Record, 2001, vol. 262, pp. 398-419.
Kurtz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", SPINE, 1993, vol. 18, No. 10, pp. 1298-1310.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (INJURY), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. AU2015205875, dated Jun. 15, 2016.
Official Communication in Australian Application No. 2014277721, dated Sep. 8, 2016.
Official Communication in Japanese Application No. 2015-242990, dated Dec. 12, 2016.
Official Communication in Japanese Application No. JP 2013-555592, dated Aug. 8, 2016.
Official Communication in European Application No. 14774714.1, dated Oct. 21, 2016.
Official Communication in European Application No. 14776445.0, dated Nov. 7, 2016.
Official Communication in European Application No. 14850082.0, dated Aug. 31, 2016.
Sharpe Products, "Metal Round Disks", https://web.archive.org/web/20170705214756/https://sharpeproducts.com/store/metal-round-disks, as archived Jul. 5, 2017 in 3 pages.
Official Communication in Canadian Application No. 2,803,783, dated Apr. 5, 2017.
Official Communication in European Application No. 16180368.9, dated Mar. 31, 2017.
Official Communication in Australian Application No. 2014277721, dated Jan. 9, 2017.
Official Communication in Canadian Application No. 2,804,223, dated Jun. 5, 2017.
Official Communication in European Application No. 11818586.7, dated Feb. 3, 2017.
Official Communication in Japanese Application No. 2015-242990, dated May 8, 2017.
Official Communication in European Application No. EP12749447.4, dated Jan. 4, 2017.
Official Communication in European Application No. EP12749447.4, dated Apr. 4, 2017.
Official Communication in European Application No. 12749251.0, dated Jan. 4, 2017.
Official Communication in European Application No. 12749251.0, dated May 9, 2017.

(56) References Cited

OTHER PUBLICATIONS

International Preliminary Report on Patentability and Written Opinion in International Application No. PCT/US2015/050441, dated Mar. 30, 2017.

* cited by examiner

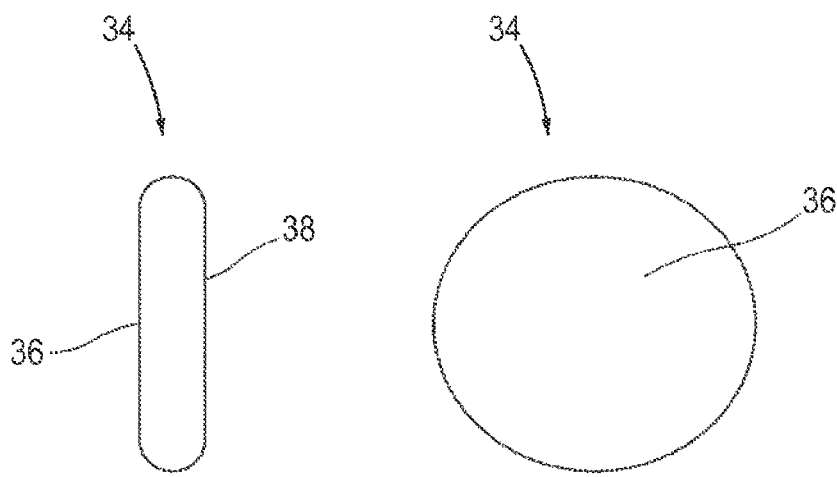
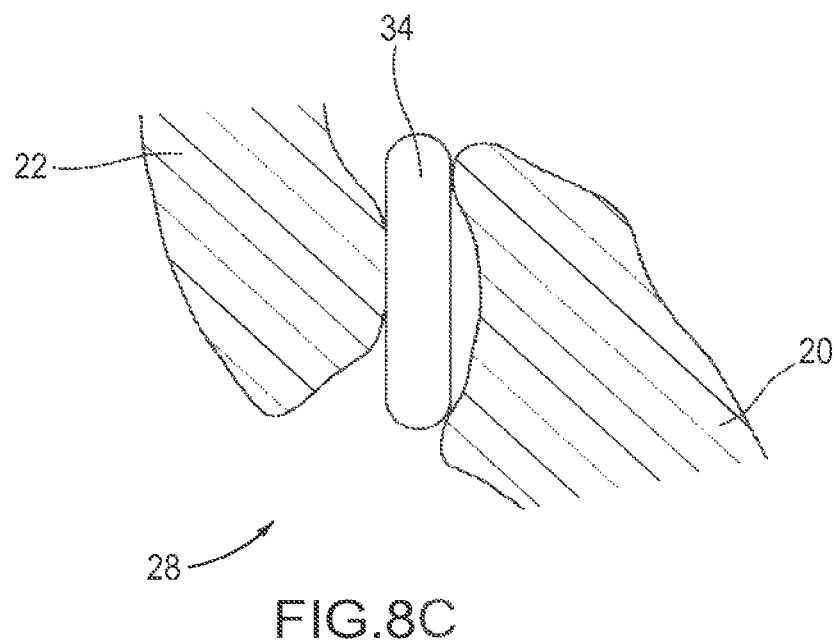

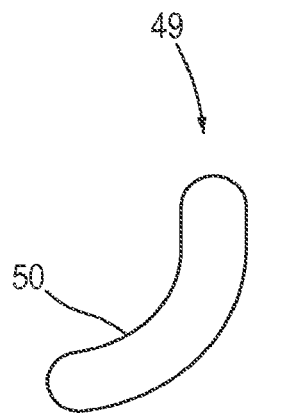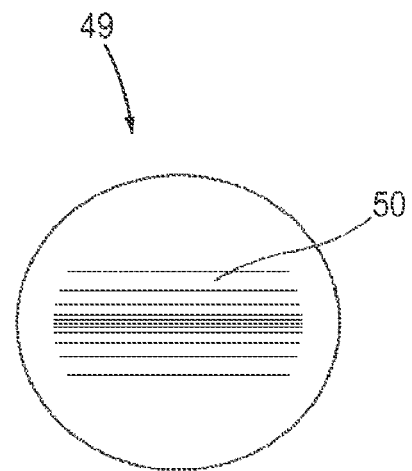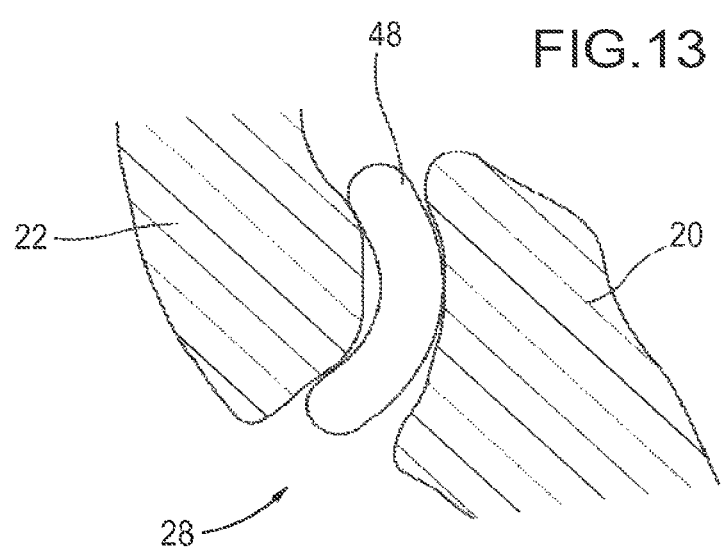

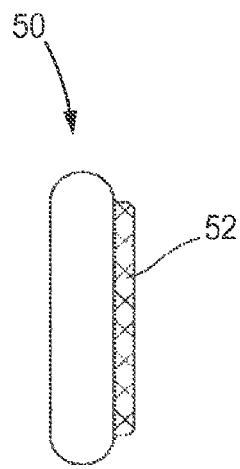 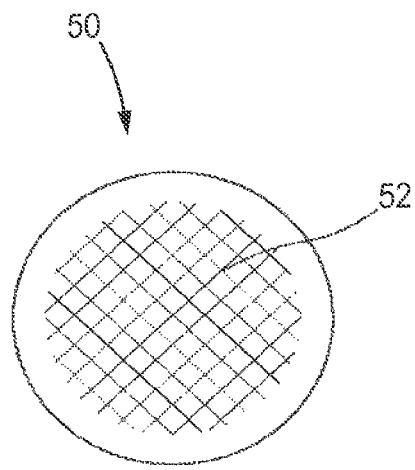
FIG.14A  FIG.14B
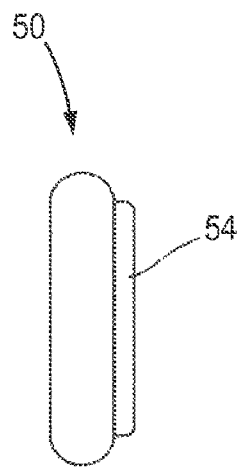 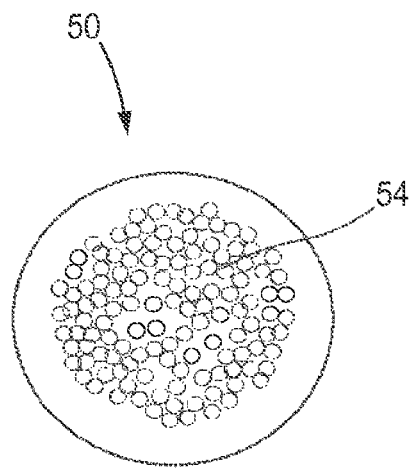
FIG.15A  FIG.15B

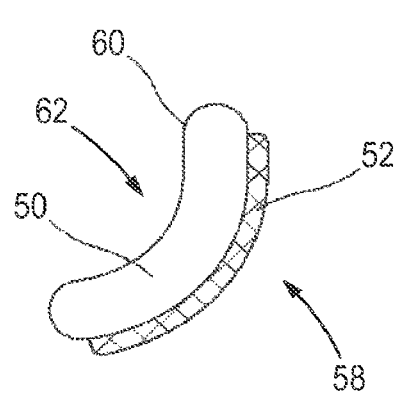
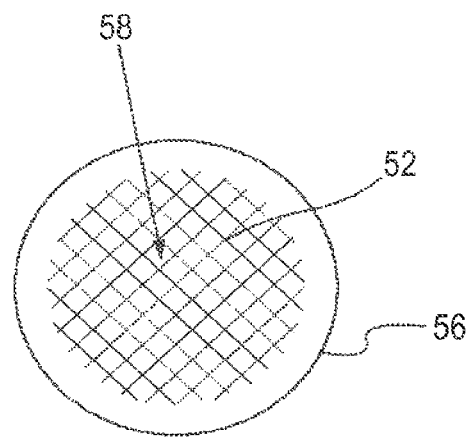
FIG.16A  FIG.16B
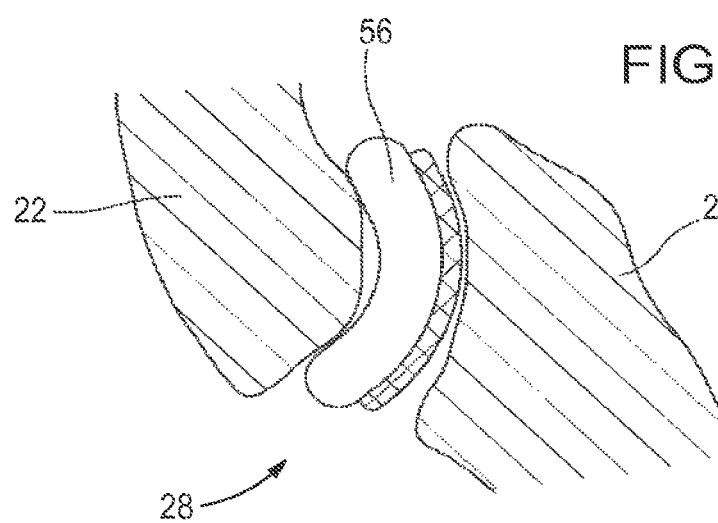
FIG.17

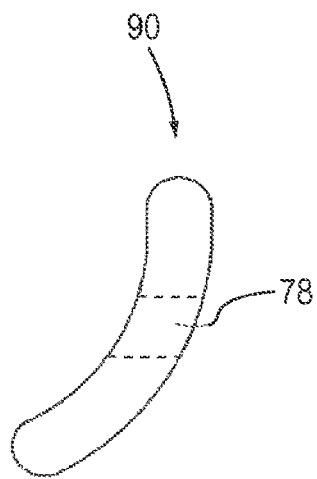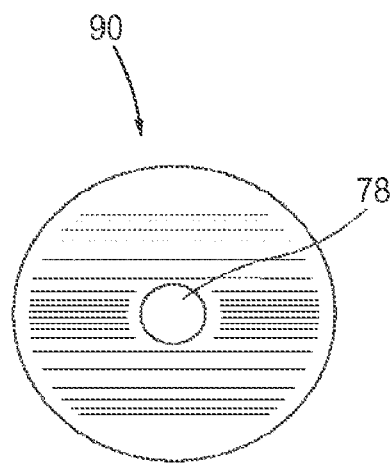
FIG.25A  FIG.25B
FIG.26
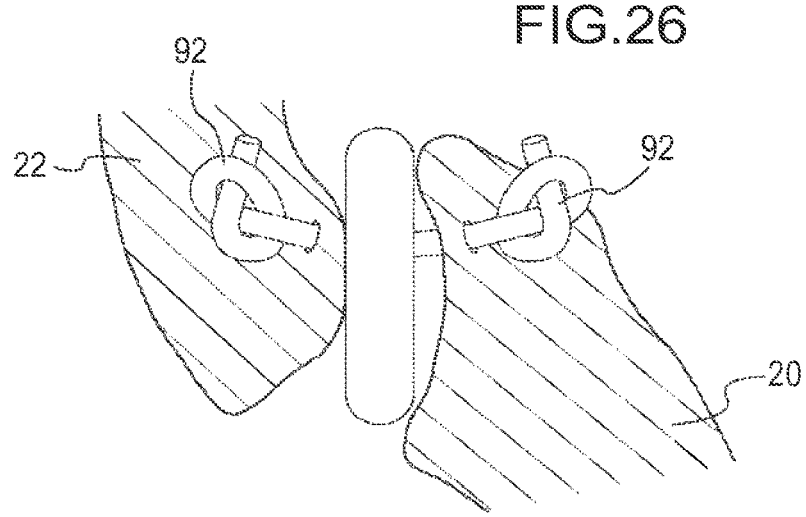

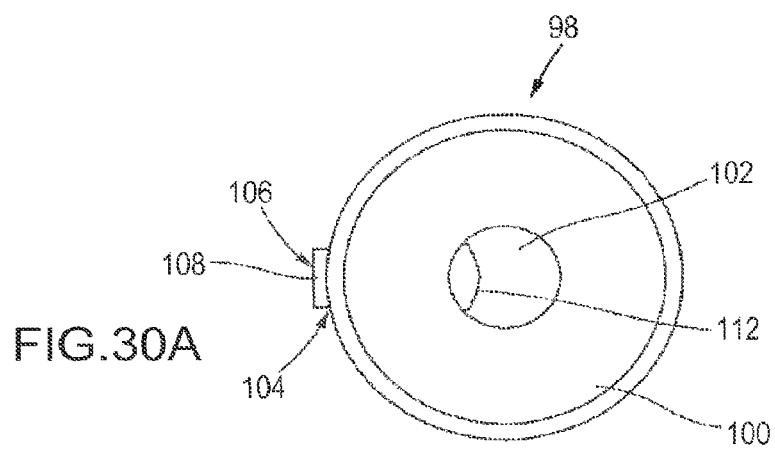
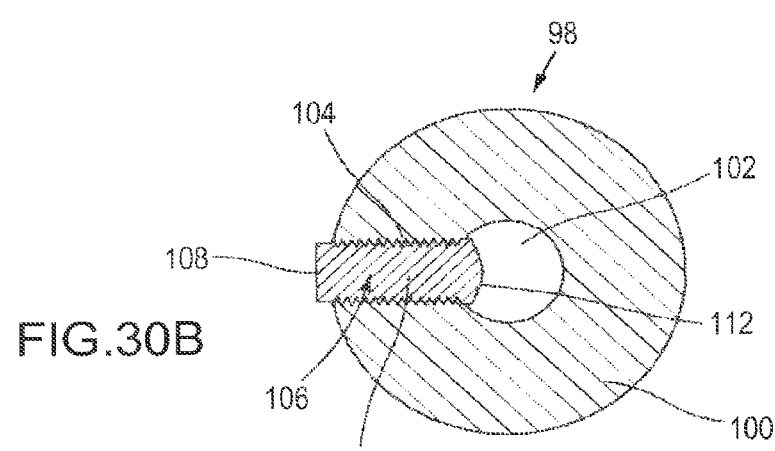
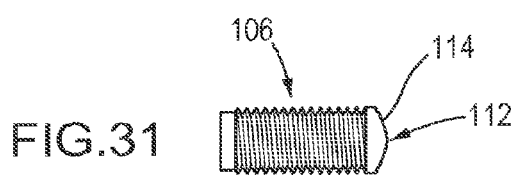
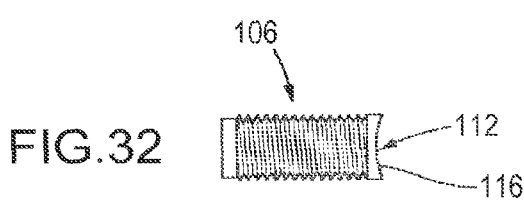
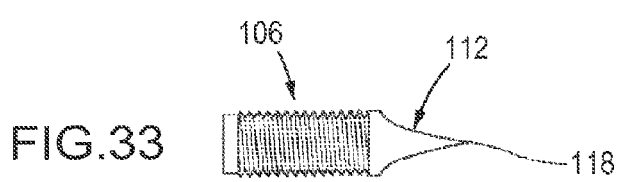

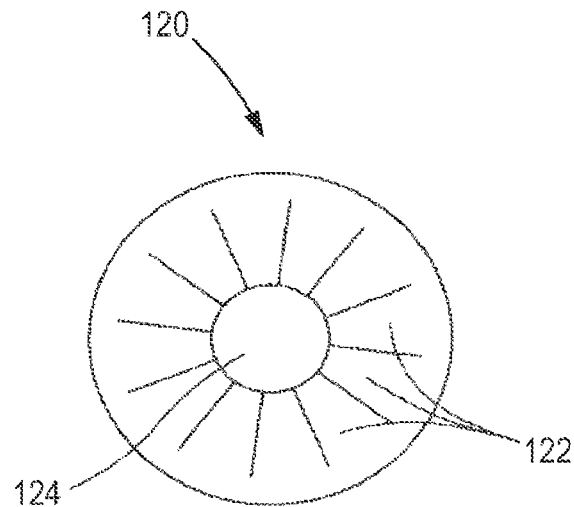
FIG.34A  FIG.34B
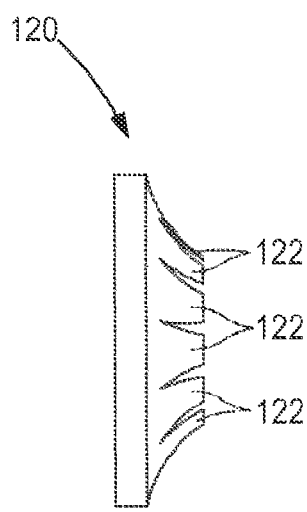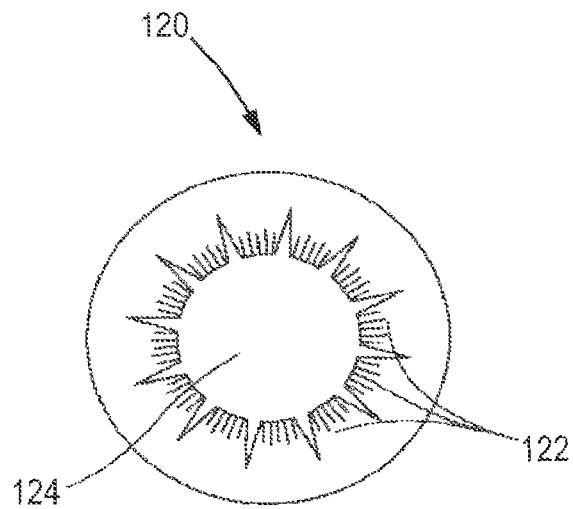
FIG.35A  FIG.35B

DEVICE AND METHOD FOR REINFORCEMENT OF A FACET

INCORPORATION BY REFERENCE TO ANY PRIORITY APPLICATIONS

This application claims priority benefit under 35 U.S.C. §119(e) of U.S. Provisional Patent Application No. 61/883,960, filed Sep. 27, 2013, the entirety of which is hereby incorporated by reference herein.

BACKGROUND OF THE INVENTION

Some embodiments described herein relate generally to methods and implants for fusing bone, for example, fusing vertebrae by securing the articular processes of the vertebrae.

Traumatic, inflammatory, and degenerative disorders of the spine can lead to severe pain and loss of mobility. One source of back and spine pain is related to degeneration of the facets of the spine or facet arthritis. Bony contact or grinding of degenerated facet joint surfaces can play a role in some pain syndromes. While many technological advances have focused on the intervertebral disc and artificial replacement or repair of the intervertebral disc, little advancement in facet repair has been made. Facet joint and disc degeneration frequently occur together. Thus, a need exists to address the clinical concerns raised by degenerative facet joints.

The current standard of care to address the degenerative problems with the facet joints is to fuse the two adjacent vertebrae. By performing this surgical procedure, the relative motion between the two adjacent vertebrae is stopped, thus stopping motion of the facets and any potential pain generated as a result thereof. Procedures to fuse two adjacent vertebrae often involve fixation and/or stabilization of the two adjacent vertebrae until the two adjacent vertebrae fuse.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones can be slow and/or complex Accordingly, a need exists for an apparatus and a procedure to quickly and/or easily stabilize and/or fixate a bone.

SUMMARY OF THE INVENTION

In some embodiments, a device for reinforcing a facet joint implant is provided. The device comprises a first securing segment comprising a proximal surface and a distal surface. The first securing segment comprises a first lumen disposed between the proximal surface and the distal surface. The first lumen is adapted for receiving a fastener member. The device comprises a second securing segment comprising a proximal surface and a distal surface. The second securing segment comprises a second lumen. The device comprises a central portion between the first securing segment and the second securing segment.

In some embodiments a longitudinal axis of the first securing segment is disposed at an angle relative to a longitudinal axis of the second securing segment. In some embodiments, a plane of the distal surface of the first securing segment is not parallel to a plane of the distal surface of the second securing segment. In some embodiments, the distal surface of the facet reinforcement device is configured for engaging a bony surface of a facet. In some embodiments, the distal surface of the facet reinforcement device comprises sharp engagement members.

In some embodiments, a kit for treating a spine is provided. The kit comprises a fastener member. The kit comprises a facet reinforcement device. The facet reinforcement device comprises a proximal surface and a distal surface. The facet reinforcement device comprises a lumen disposed between the proximal surface and the distal surface. The lumen is adapted for receiving the fastener member.

In some embodiments, the facet reinforcement device further comprises a second portion adapted to attach to a spinous process of a vertebra. In embodiments, the second portion of the facet reinforcement device comprises at least one lumen. Some embodiments of the kit, further comprise a fastener for securing the facet reinforcement device to the vertebra. In some embodiments, the fastener secures the facet reinforcement device to the spinous process of the superior vertebra. In some embodiments, the fastener is a screw or bolt.

In some embodiments, a method for treating a spine is provided. The method may include placing a facet reinforcement device comprising a lumen adjacent to a first vertebra. The method may include passing a fastener member through the lumen. The method includes passing the fastener member through a first articular process of a facet joint. The method may include passing the fastener member through a second articular process of the facet joint. The method may include securing one end of the fastener member to the other end of the fastener member, thereby retaining the facet reinforcement device.

In some embodiments, a method for treating a spine is provided. The method may include the step of preparing a facet joint for fixation. The method may include passing a fastener member through a first articular process of a facet joint. The method may include passing a fastener member through a second articular process of the facet joint. The method may include placing a facet reinforcement device with a lumen for receiving the flexible fastening band against a surface of the first articular process. The method may include passing a fastener member through the lumen. The method may include securing the fastener member. The method may include securing the facet reinforcement device to a spinous process with a fastener. The methods may further comprise inserting a facet implant with an interface configured to receive the fastener member into the facet joint. The methods may further comprise passing the fastener member through the interface of the facet implant.

In some embodiments, a method for treating a spine is provided. Methods may further comprise preparing a second facet joint at a same level of the spine for fixation. The method may include placing a second facet reinforcement device against a first articular process of the second facet joint. The method may include passing a second fastener member through a first articular process of the second facet joint. The method may include passing a second fastener member through a second articular process of the second facet joint. The method may include securing the second fastener member. The method may include securing the second facet reinforcement device to a spinous process with a fastener. The methods may further comprise inserting a second facet implant with an interface configured to receive the fastener member into the facet joint. The methods may further comprise passing the second fastener member through the interface of the second facet implant.

In some embodiments, a device for placement on a facet joint is provided, the purpose of the device being to provide reinforcement to the bone when a fastener member is used to secure the joint. The device may include sharp engagement members on a bone contact side to prevent migration. The device may include a through-opening to accept a primary facet fixation device. In some embodiments, the device for placement on a facet joint has a second through-opening for accepting at least one additional fastener. In some embodiments, a screw may be provided for placement through the second through-opening.

BRIEF DESCRIPTION OF THE DRAWINGS

FIGS. 8A and 8B are schematic views of one embodiment of a facet joint implant comprising a circular disc.

FIG. 8C is a schematic view of the implant from FIG. 7A implanted in a facet joint.

FIGS. 12A and 12B are schematic views of one embodiment of a facet joint implant comprising a curved disc.

FIG. 13 is a schematic view of the implant from FIG. 12A implanted in a facet joint.

FIGS. 14A and 14B are schematic views of one embodiment of a facet joint implant comprising a disc with a roughened surface on one face.

FIGS. 15A and 15B are schematic views of one embodiment of a facet joint implant comprising a disc with a porous surface on one face.

FIGS. 16A and 16B are schematic views of one embodiment of a facet joint implant comprising a bent disc with a roughened surface on the greater face.

FIG. 17 is a schematic view of the implant from FIG. 16A implanted in a facet joint.

FIGS. 25A and 25B are schematic views of one embodiment of a facet joint implant comprising a curved disc with a fastener interface.

FIG. 26 depicts one embodiment where the cable is engaged to the articular processes using knots in the cable.

FIGS. 30A and 30B are elevational and cross-sectional views of one embodiment of the set-screw fastener rings, respectively.

FIGS. 31 through 33 are elevational views of various embodiments of the screw in the set-screw fastener rings.

FIGS. 34A to 35B are one embodiment comprising friction fit fastener rings. FIGS. 34A and 34B depict the fastener rings in their reduced state and FIGS. 35A and 35B depict the fastener rings in their expanded state.

FIGS. 36B and 36C depict a threaded fastener member with a pivotable washer.

DETAILED DESCRIPTION

As used in this specification, the singular forms "a," "an" and "the" include plural referents unless the context clearly dictates otherwise. Thus, for example, the term "a ratchet" is intended to mean a single ratchet or a combination of ratchets. As used in this specification, a substance can include any biologic and/or chemical substance, including, but not limited to, medicine, adhesives, etc, and/or a bone graft, including, but not limited to, autograft, allograft, xenograft, alloplastic graft, a synthetic graft, and/or combinations of grafts, medicines, and/or adhesives. While exemplary references are made with respect to vertebra, in some embodiments another bone can be involved. While specific reference may be made to a specific vertebra and/or subset and/or grouping of vertebrae, it is understood that any vertebra and/or subset and/or grouping, or combination of vertebrae can be used.

Figure 1:
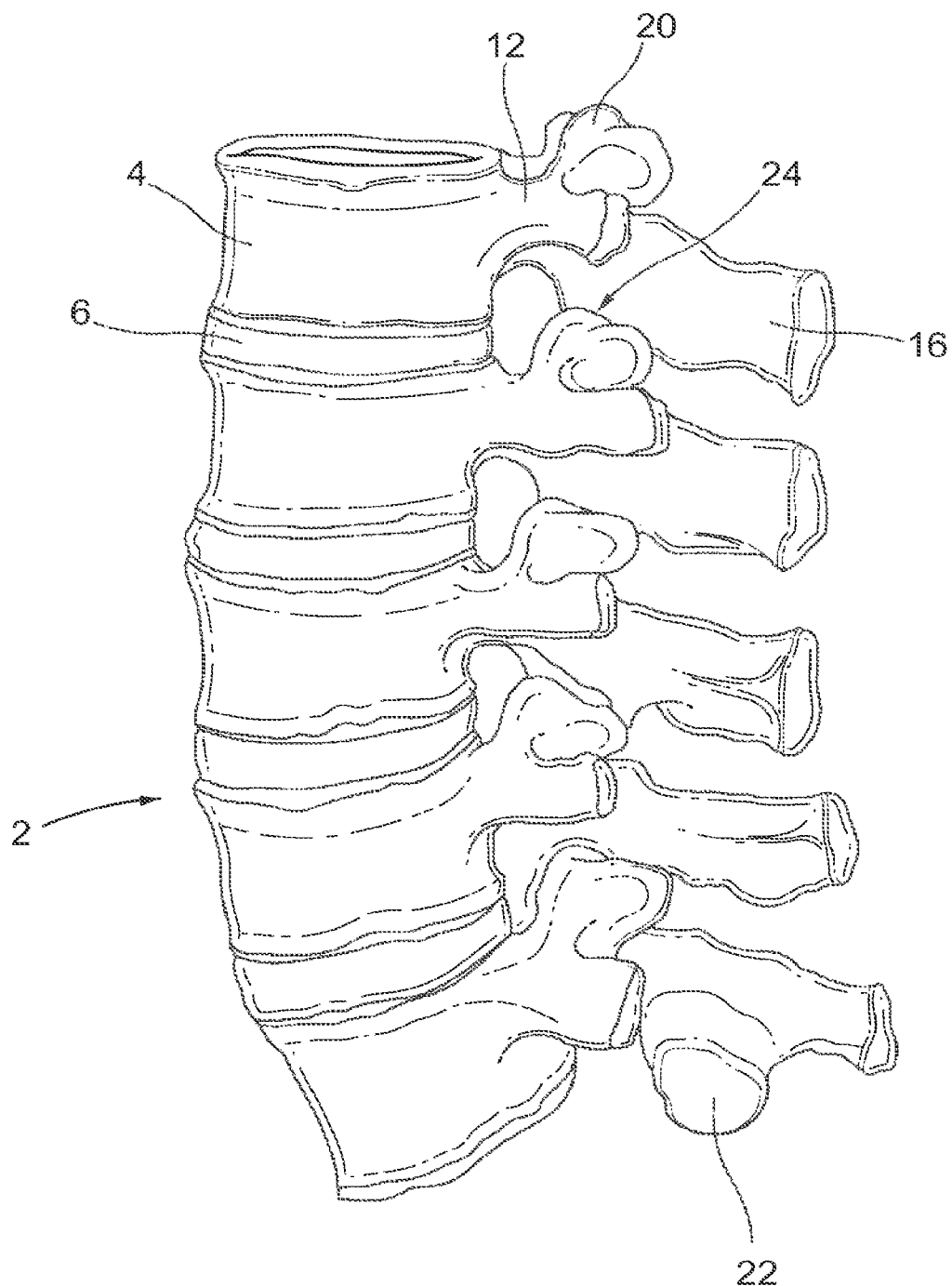
FIG. 1 is a lateral elevational view of a portion of the vertebral column.
Figure 2A:
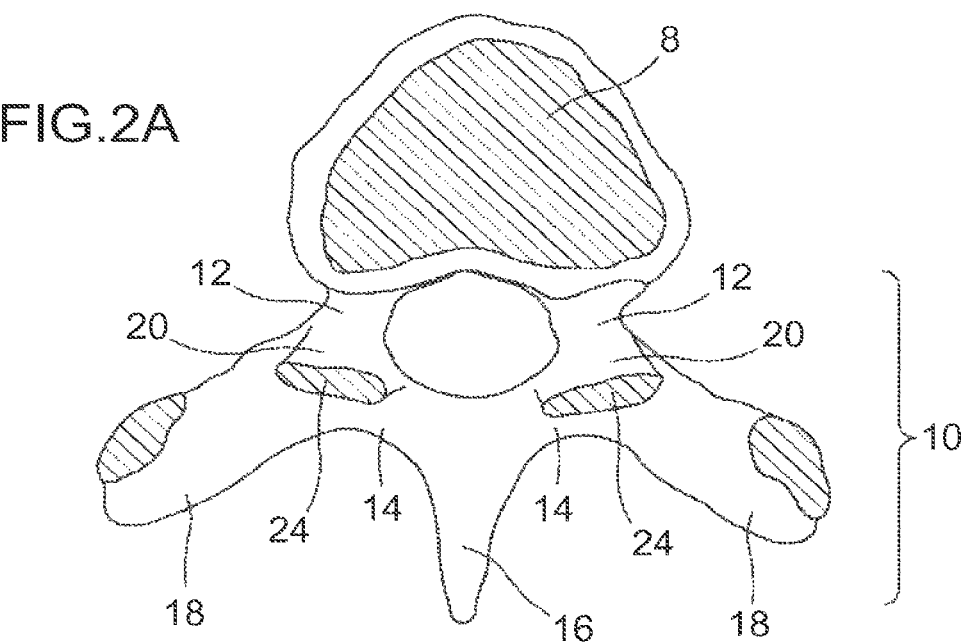
FIG. 2A is a schematic superior view of an isolated thoracic vertebra.
Figure 2B:
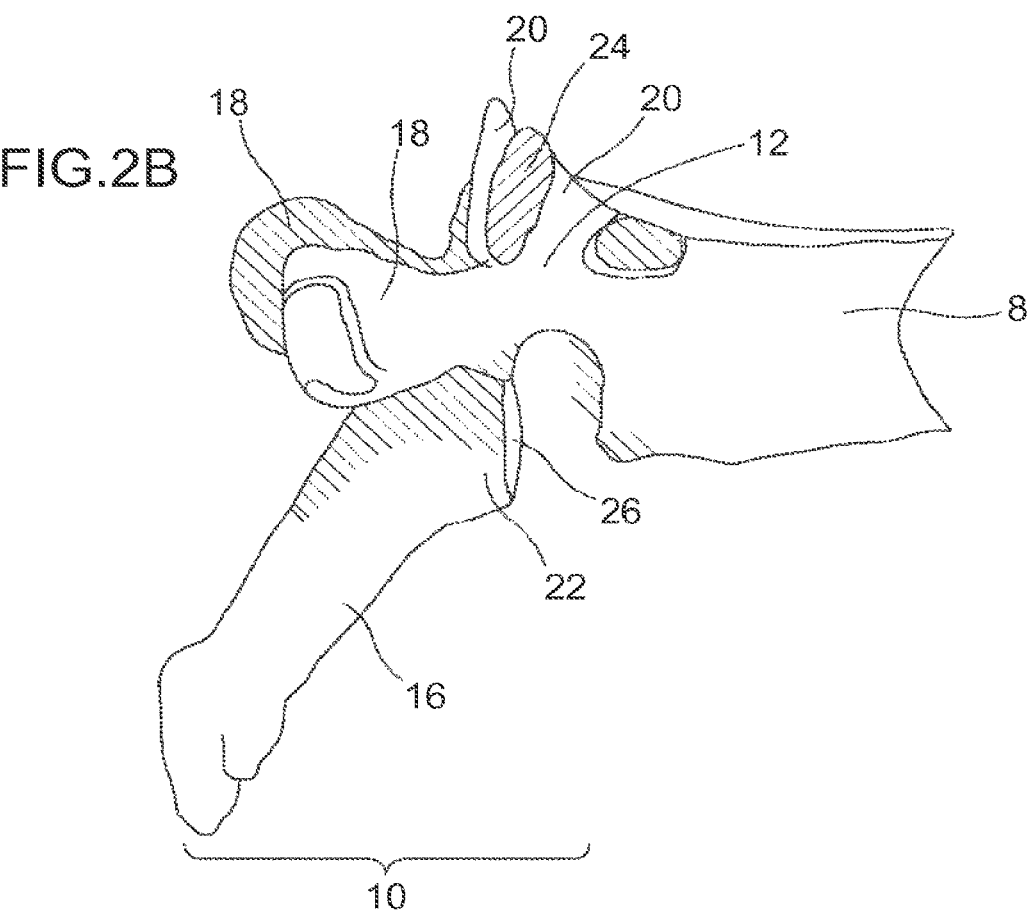
FIG. 2B are schematic side view of an isolated thoracic vertebra.
Figure 3A:
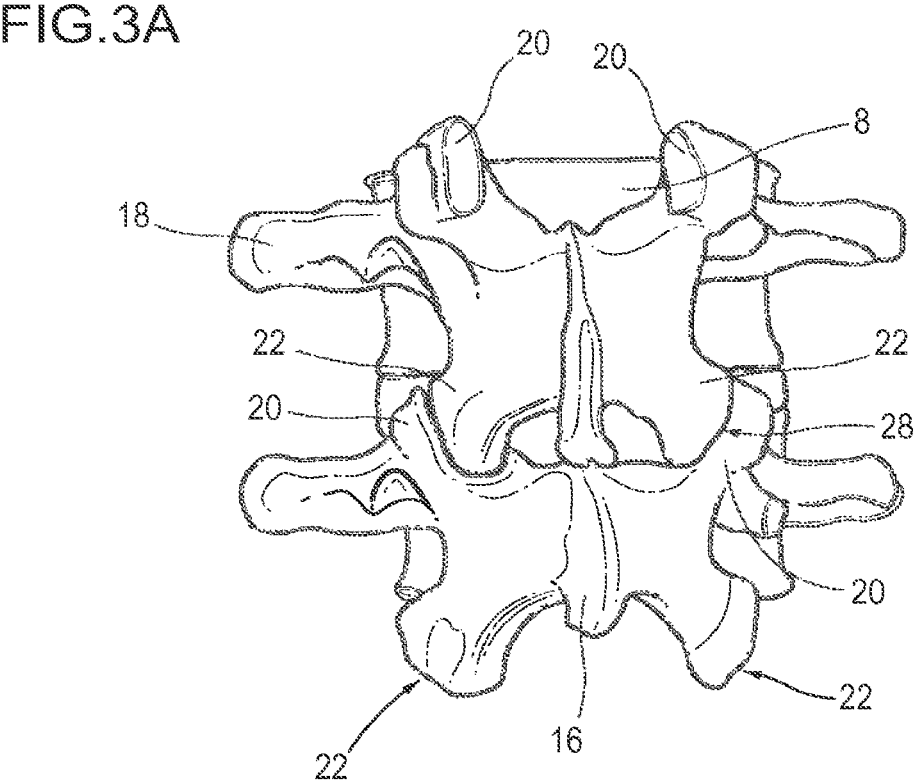
FIG. 3A is a schematic posterior elevational view of a portion of the vertebral column.
Figure 3B:
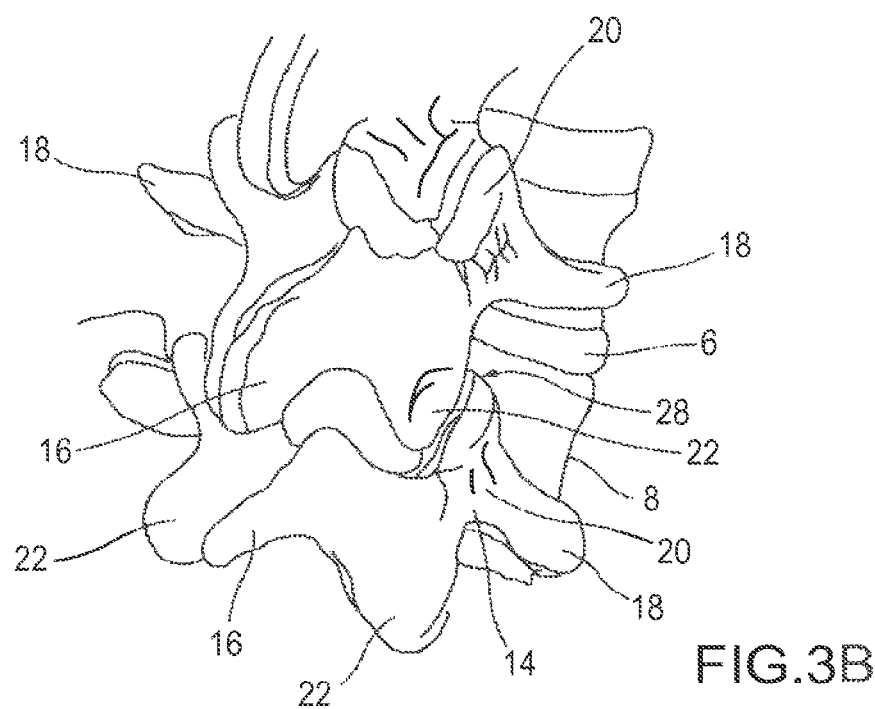
FIG. 3B is a posterior-oblique elevational view of a portion of the vertebral column.
Figure 4A:
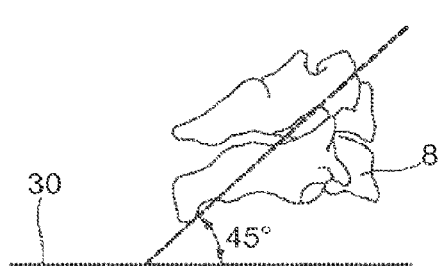
FIG. 4A is a schematic side view of a facet joint in the cervical vertebrae.
Figure 4B:
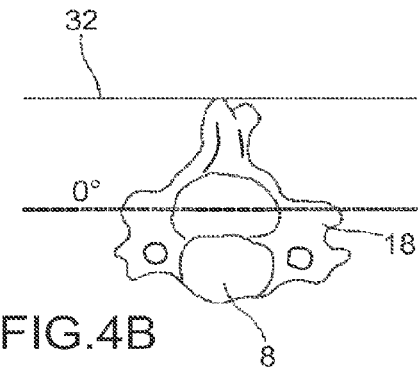
FIG. 4B is a schematic superior view of a facet joint in the cervical vertebrae.

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae (see FIGS. 3A and 3B). The facet joints are true synovial joints with cartilaginous surfaces and a joint capsule.

Figure 5A:
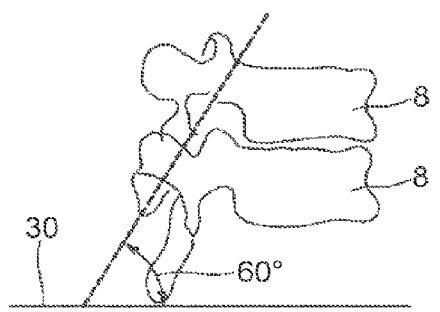
FIG. 5A is a schematic side view of a facet joint in the thoracic vertebrae.
Figure 5B:
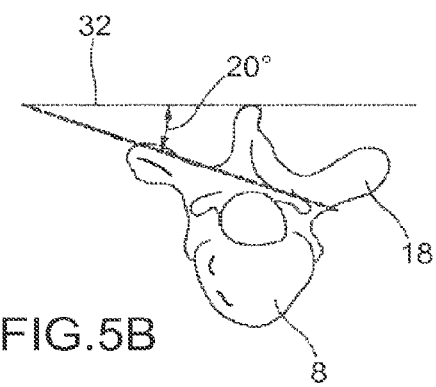
FIG. 5B is a schematic superior view of a facet joint in the thoracic vertebrae.
Figure 6A:
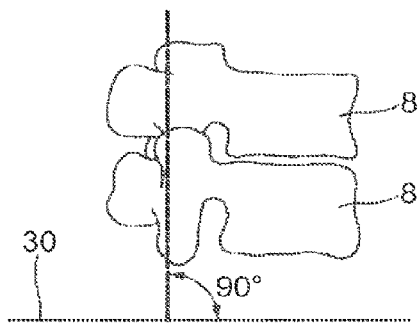
FIG. 6A is a schematic side view of a facet joint in the lumbar vertebrae.
Figure 6B:
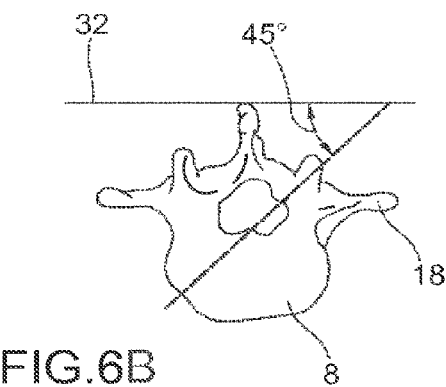
FIG. 6B is a schematic superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

Figure 7:
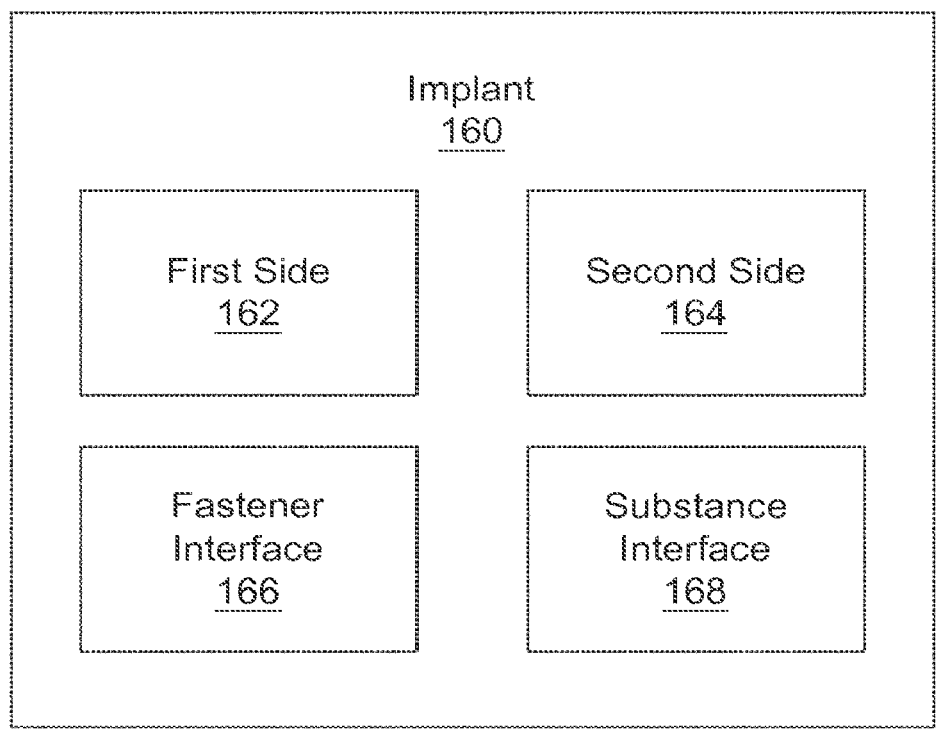
FIG. 7 is a block diagram of an implant according to an embodiment.

In some embodiments described herein, a vertebral facet joint implant can be used to stabilize, fixate, and/or fuse a first vertebra to a second vertebra to reduce pain, to reduce further degradation of a spine, or of a specific vertebra of a spine, and/or until the first vertebra and the second vertebra have fused. In some embodiments, the vertebral facet joint implant can be implanted and deployed to restore the space between facets of a superior articular process of a first vertebra and an inferior articular process of an adjacent vertebra. In some embodiments, the vertebral facet joint implant can be implanted and deployed to help stabilize adjacent vertebrae with adhesives, and/or can be implanted and deployed to deliver a medication. FIG. 7 depicts a block diagram of a vertebral facet joint implant ("implant") 160. Implant 160 includes a first side 162, a second side 164, a fastener interface 166, and a substance interface 168. FIGS. 8A-47B depict implants and fasteners according to different embodiments.

As shown in FIG. 7, implant 160 can be, for example, substantially disc shaped. In other embodiments, the spacer can be other shapes, e.g., square, elliptical, or any other shape. First side 162 and/or second side 164 can be, for example, convex, concave, or flat. Said another way, first side 162 can be concave, convex, or flat, and second side 164 can be concave, convex, or flat; for example, first side 162 can be concave and second side 164 can be concave, first side 162 can be concave and second side 164 can be convex, etc. In such embodiments, the shape can be determined based on a shape of a bone portion that the first side 162 and/or the second side 164 is configured to contact. Said another way, the first side 162 and/or the second side 164 can be shaped to substantially compliment the shape of a bone portion. On other words, the first side 162 or the second side 164 need not exactly match the shape of the corresponding bone portion, but instead can have a concave shape for a bone portion with a generally convex shape where the contact with the implant is to occur or can have a convex shape for a bone portion with a generally concave shape where the contact with the implant is to occur. Implant 160 can include any biocompatible material, e.g., stainless steel, titanium, PEEK, nylon, etc.

Implant 160 includes fastener interface 166. Fastener interface 166 can be configured to retain implant 160 in substantially the same position. Specifically, fastener interface 166 can be configured to accept a fastener member (not shown) to substantially prevent movement of implant 160. Fastener interface 166 can include an aperture and/or other opening. Fastener interface 166 can extend through implant 160, e.g. can extend from first side 162 and through to second side 164. In some embodiments, fastener interface 166 can extend through only a portion of implant 160, e.g. can extend from first side 162 and through less than half of a width (not shown) of implant 160. Fastener interface 166 can be disposed on and/or through first side 162, second side 164, and/or both first side 162 and second side 164. Fastener interface 166 can be disposed through a center (not shown) of implant 160. In other embodiments, fastener interface 166 can be disposed anywhere on and/or through implant 160, e.g., offset from center. Fastener interface 166 can be substantially circular (cylindrical). In other embodiments, fastener interface 166 can be other shapes and/or can be shaped based on a shape of the fastener member, for example, rectangular (cuboid). In some embodiments, fastener interface 166 can be a irregular shape, based at least in part in the location of fastener interface 166, see, e.g., FIG. 48, and/or partial shapes, see, e.g., FIG. 23B. Fastener interface 166 can include a substantially smooth inner surface (not shown) to allow the fastener member to easily pass through and/or into fastener interface 166, and/or can include a threaded inner surface to allow the fastener member to thread into fastener interface 166. While depicted in FIG. 7 as including one fastener interface, implant 160 can include more than one fastener interface 160.

Implant 160 includes substance interface 168. Substance interface can be configured to retain, carry and/or otherwise deliver a substance to aid in fusion, such as, for example, medicines, adhesives, bone graft, and/or combinations of substances. Substance interface 168 can include an aperture and/or other opening. Substance interface 168 can extend through implant 160, e.g. can extend from first side 162 and through to second side 164. In some embodiments, fastener interface can extend through only a portion of implant 160, e.g. can extend from first side 162 and through less than half of a width (not shown) of implant 160. Substance interface 168 can be disposed on and/or through first side 162, second side 164, and/or both first side 162 and second side 164. Substance interface 168 can be disposed through a center (not shown) of implant 160. In other embodiments, substance interface 168 can be disposed anywhere on and/or through implant 160, e.g., offset from center. Substance interface 168 can be substantially circular (cylindrical). In other embodiments, substance interface 168 can be other shapes and/or can be shaped based on a shape of the fastener member, for example, rectangular (cuboid). In some embodiments, substance interface 168 can be an irregular shape, based at least in part in the location of substance interface 168. While depicted in FIG. 7 as including one substance interface, implant 160 can include more than one substance interface 160. The location, size, shape, and/or number of substance interface(s) 168 can be determined based on the location, size, shape, and/or number of fastener interface(s) 166.

Figure 9A:
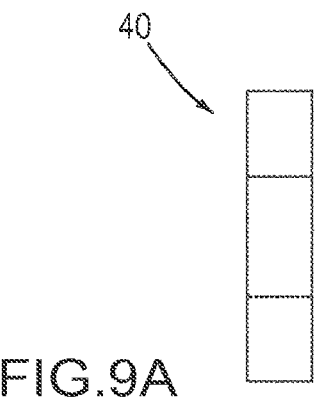
FIGS. 9A and 9B are schematic views of one embodiment of a facet joint implant comprising an octagonal disc.
Figure 9B:
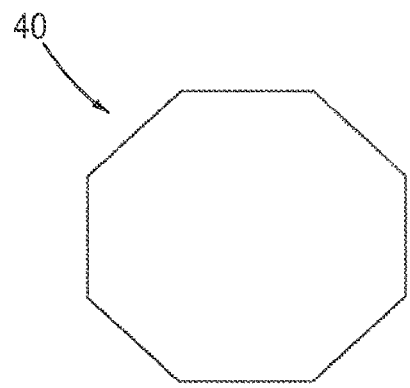
Figure 10A:
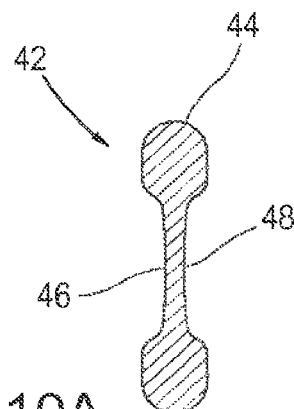
FIGS. 10A and 10B are schematic views of one embodiment of a facet joint implant comprising a biconcave disc.
Figure 10B:
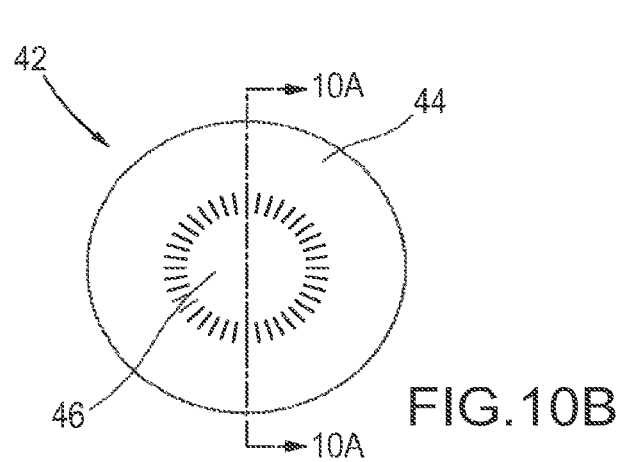

In one embodiment, a device for restoring the spacing between two facets of a facet joint is provided. As shown in FIGS. 8A and 8B, the device comprises a implant 34 with a least two faces, a first face 36 adapted to contact the articular surface of one facet of the facet joint and a second face 38 adapted to contact the articular surface of the other facet. In one embodiment, the implant 34 has a generally circular profile and is sized to fit generally within the joint capsule of the facet joint 28. FIG. 8C illustrates the implant 34 of FIGS. 8A and 8B positioned in a facet joint. In other embodiments, the implant can have any of a variety of profiles, including but not limited to square, rectangle, oval, star, polygon or combination thereof. An octagonal implant is shown in FIGS. 9A and 9B. In one embodiment, a implant having the desired shape is selected from an array of prostheses after radiographic visualization of the articular processes and/or by radio-contrast injection into the facet joint to visualize the joint capsule. In one embodiment, the implant has a diameter of about 4 mm to about 30 mm. In another embodiment, the implant has a diameter of about 5 mm to about 25 mm. In still another embodiment, the implant has a diameter of about 10 mm to about 20 mm. In one embodiment, the implant has a cross-sectional area of about 10 $mm^2$ to about 700 $mm^2$. In another embodiment, the implant has a cross-sectional area of about 25 $mm^2$ to about 500 $mm^2$. In still another embodiment, the implant has a cross-sectional area of about 20 $mm^2$ to about 400 $mm^2$, or about 25 $mm^2$ to about 100 $mm^2$.

Figure 11A:
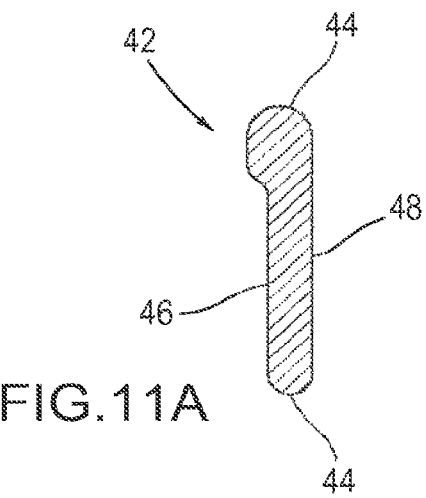
FIGS. 11A and 11B are schematic views of one embodiment of a facet joint implant comprising a single-face variable thickness disc.
Figure 11B:
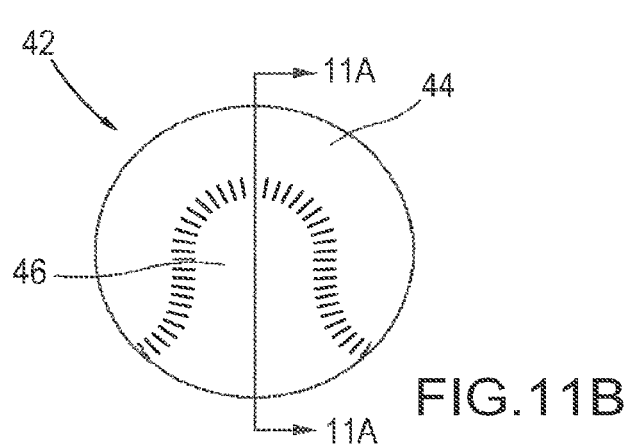

The implant has a thickness generally equal to about the anatomic spacing between two facets of a facet joint. The implant generally has a thickness within the range of about 0.5 mm to about 3.0 mm. In certain embodiments, the implant has a thickness of about 1 mm to about 2 mm. In one preferred embodiment, the implant has a thickness of about 0.5 mm to about 1.5 mm. In one embodiment, the thickness of the implant is nonuniform within the same implant. For example, in FIGS. 10A and 10B, the thickness of the implant 42 is increased around the entire outer edge 44, along at least one and, as illustrated, both faces 46, 48. In FIGS. 11A and 11B, only a portion of the edge 44 on one face 46 of the implant 42 has a thickness that is greater than the thickness of a central region, and, optionally, also thicker than the typical anatomic spacing between two facets of a facet joint. An increased edge thickness may resist lateral displacement of the implant out of the facet joint.

In some embodiments, the implant is configured to provide an improved fit with the articular process and/or joint capsule. For example, in FIGS. 12A and 12B, the implant 49 has a bend, angle or curve 50 to generally match the natural shape of an articular facet. FIG. 13 depicts the implant of FIGS. 12A and 12B positioned in a facet joint. The implant may be rigid with a preformed bend. Alternatively, the implant may be sufficiently malleable that it will conform post implantation to the unique configuration of the adjacent facet face. Certain embodiments, such as those depicted in FIG. 8C and FIG. 13, the implant is configured to be implanted between the articular processes and/or within the joint capsule of the facet joint, without securing of the implant to any bony structures. Such embodiments can thus be used without invasion or disruption of the vertebral bone and/or structure, thereby maintaining the integrity of the vertebral bone and/or structure.

In one embodiment, at least a portion of one surface of the implant is highly polished. A highly polished portion of the implant may reduce the surface friction and/or wear in that portion of the implant as it contacts bone, cartilage or another surface of the implant. A highly polished surface on the implant may also decrease the risk of the implant wedging between the articular surfaces of the facet joint, which can cause pain and locking of the facet joint.

In one embodiment, shown in FIGS. 14A and 14B, at least a portion of one surface of the implant 50 has a roughened surface 52. A roughened surface may be advantageous when in contact with a bone or tissue surface because it may prevent slippage of the implant 50 against the bone and aid in maintaining the implant 50 in the joint. In one embodiment, shown in FIGS. 15A and 15B, at least a portion of one surface of the implant 50 has a porous surface 54. A porous surface 54 can be created in any a variety of ways known in the art, such as by applying sintered beads or spraying plasma onto the implant surface. A porous surface 54 can allow bone to grow into or attach to the surface of the implant 50, thus securing the implant 50 to the bone. In one embodiment, an adhesive or sealant, such as a cyanoacrylate, polymethylmethacrylate, or other adhesive known in the art, is used to bond one face of the implant to an articular surface.

In one embodiment, one surface of the implant is roughened or porous and a second surface that is highly polished. The first surface contacts or engages one facet of the facet joint and aids in maintaining the implant between the articular surfaces. The second surface of the implant is highly polished and contacts the other facet of the facet joint to provide movement at that facet joint. FIGS. 16A and 16B represent one embodiment of the implant comprising a curved or bent disc 56 with a roughened surface 52 on the greater face 58 of the disc and a highly polished surface 60 on the lesser face 62. FIG. 17 depicts the implant of FIGS. 16A and 16B positioned in a facet joint. The implant generally maintains a fixed position relative to the facet contacting the roughened surface while the movement of the facet joint is preserved between the other facet and the highly polished lesser face of the implant.

Figure 18A:
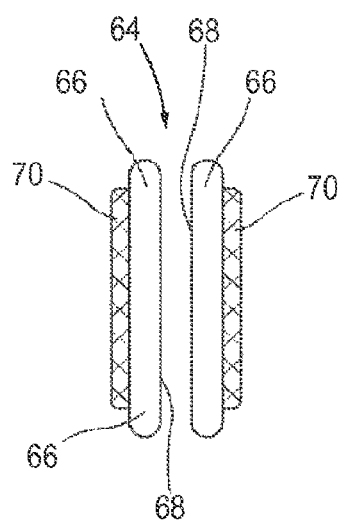
FIGS. 18A and 18B are schematic views of one embodiment of a facet joint implant comprising two discs, each with a roughened surface on one face.
Figure 18B:
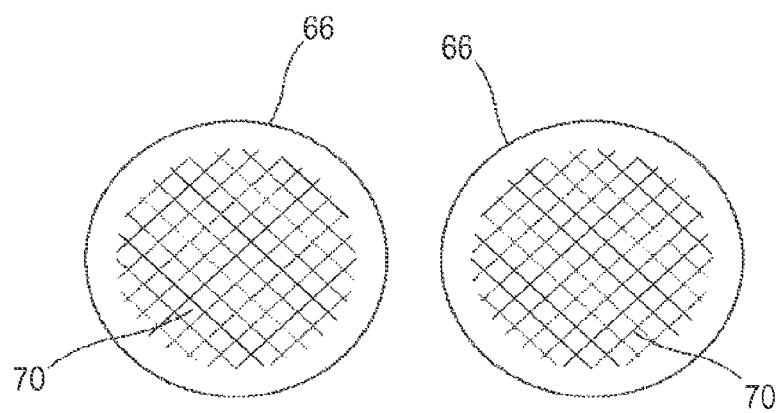
Figure 19:
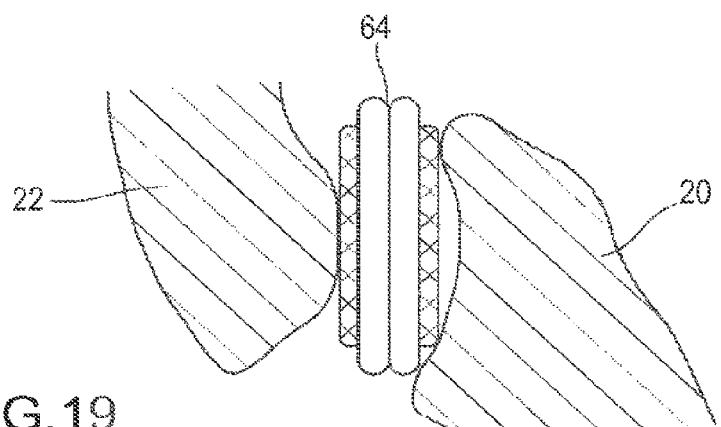
FIG. 19 is a schematic view of the implant from FIG. 18A implanted in a facet joint.

FIGS. 18A and 18B show one embodiment, where the implant 64 comprises two separate discs 66, each disc comprising a first face 68 that articulates with the complementary first face 68 of the other disc, and a second face 70 adapted to secure the disc to the adjacent bone or cartilage of one facet of the facet joint 28. In one embodiment, the thickness of one disc will generally be about half of the anatomic spacing between two facets of the facet joint. In other embodiments, the implant comprises three or more discs. In one embodiment the total thickness of all the discs is generally about 25% to about 300% of the anatomic spacing between the two facets. In another embodiment, the total thickness of the discs is generally about 50% to about 150% of the anatomic spacing. In still another embodiment, the total thickness of the discs is about 75% to about 125% of the anatomic spacing. Each disc of the two-part implant can otherwise also have features similar to those of a single-disc implant, including but not limited to curved or bent configurations, highly polished or roughened surfaces, and other feature mentioned below. The two discs need not have the same size, thickness, configuration or features. FIG. 19 depicts one embodiment of a two-part implant 64 positioned within a facet joint 28.

The implant can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials.

In one embodiment, the implant is maintained between the two facets of the facet joint by taking advantage of the joint capsule and/or other body tissue surrounding the facet joint to limit the migration of the implant out of the facet joint. In some embodiments, the shape of the implant itself is capable of resisting displacement of the implant from its position generally between the facet joint surfaces. In one embodiment, a concave or biconcave configuration resists displacement of the implant by providing an increased thickness at the periphery of the implant that requires a larger force and/or greater distraction of facet joint surfaces in order to cause displacement. In other embodiments, surface treatments or texturing are used to maintain the implant against a facet of the facet joint, as described previously. In some embodiments, a combination of disc configuration, surface texturing and existing body tissue or structures are used to maintain the position of the implant.

Bone growth facilitators, electrical current, or other known techniques may be used to accelerate osteoincorporation of textured or microporous anchoring surfaces.

The implant may be configured with a fastener interface to engage ("secure") a fastener member that facilitates retention of the implant within the joint capsule of the facet joint. Use of a fastener member may be advantageous for preventing migration of the implant over time use or with the extreme ranges of vertebral movement that may distract the articular surfaces sufficiently to allow the implant to slip out.

Figure 20:
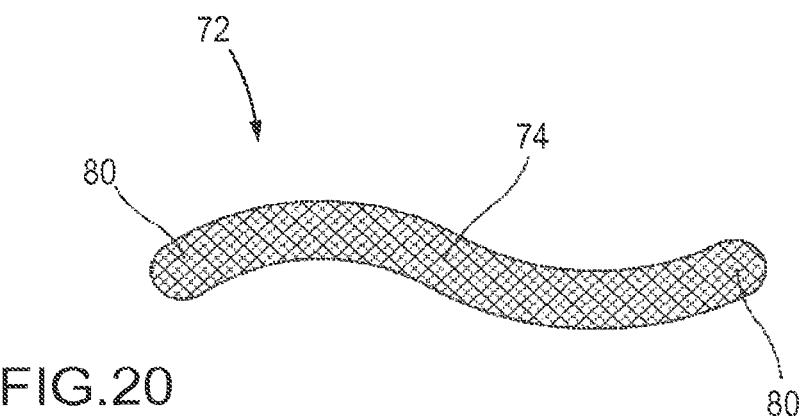
FIG. 20 is a schematic view of a fastener member comprising a braided cable.
Figures 21A, 21B:
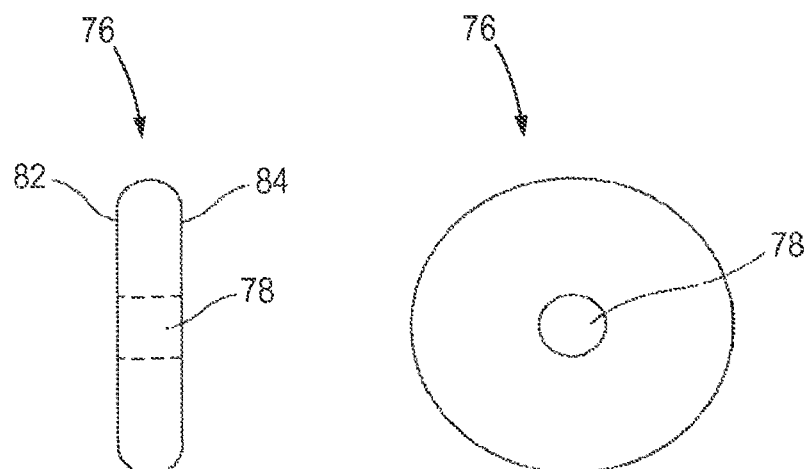
FIGS. 21A and 21B are schematic views of one embodiment of a facet joint implant with a fastener interface comprising a centrally located hole.

In one embodiment, shown in FIGS. 20 to 21B, the fastener member comprises a wire or cable 72 with a portion 74 that engages the implant 76 at a fastener interface 78, and at least one other portion 80 that engages or anchors to the bone or soft tissue surrounding the facet joint. The wire or cable may be solid, braided or multi-filamented. The fastener member in this embodiment will be described primarily as a cable or wire, but it is to be understood that any of a variety of elongate structures capable of extending through a central aperture will also work, including pins, screws, and single strand or multistrand polymeric strings or weaves, polymeric meshes and fabric and other structures that will be apparent to those of skill in the art in view of the disclosure herein.

The cross-sectional shape of the fastener member can be any of a variety of shapes, including but not limited to circles, ovals, squares, rectangles, other polygons or any other shape. The wire or cable generally has a diameter of about 0.5 mm to about 2 mm and a length of about 5 mm to about 60 mm. In other embodiments, wire or cable has a diameter of about 0.25 mm to about 1 mm, or about 0.75 mm to about 1.25 mm. The diameter of the wire or cable may vary along the length of the wire or cable. In one embodiment, the wire or cable has a length of about 10 mm to about 40 mm. In another embodiment, the wire or cable has a length of about 20 mm to about 30 mm.

In one embodiment, shown in FIGS. 21A and 21B, the fastener interface 78 of the implant 76 is a conduit between the two faces 82, 84 of the implant 76, forming an aperture 78. In one embodiment, the aperture 78 has a diameter larger than the diameter of the wire or cable 72, to provide the implant 76 with a range of motion as the facet joint moves. The aperture 78 inside diameter may be at least about 110%, often at least about 150% and in certain embodiments at least about 200% or 300% or greater of the outside diameter or corresponding dimension of the fastener member in the vicinity of the engagement portion 78. The cross-sectional shape of the aperture 78 can match or not match the cross sectional shape of the wire or cable used.

Figures 22A, 22B:
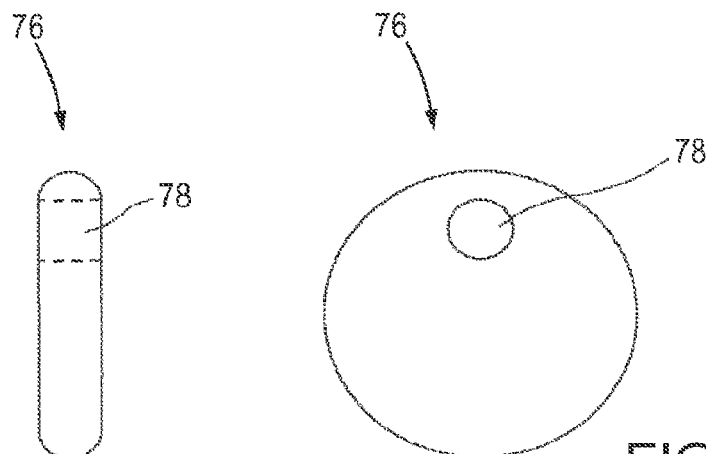
FIGS. 22A and 22B are schematic views of one embodiment of a facet joint implant with a fastener interface comprising an eccentrically located hole.
Figures 23A, 23B:
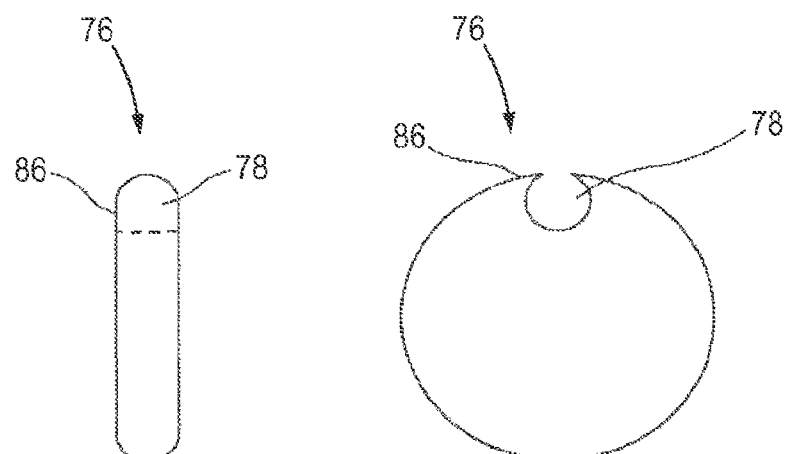
FIGS. 23A and 23B are schematic views of one embodiment of a facet joint implant with a fastener interface comprising an edge contiguous hole.
Figure 24A:
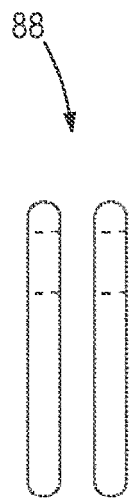
FIGS. 24A and 24B are schematic views of one embodiment of a facet joint implant comprising two discs, each with an eccentrically located hole.
Figure 24B:
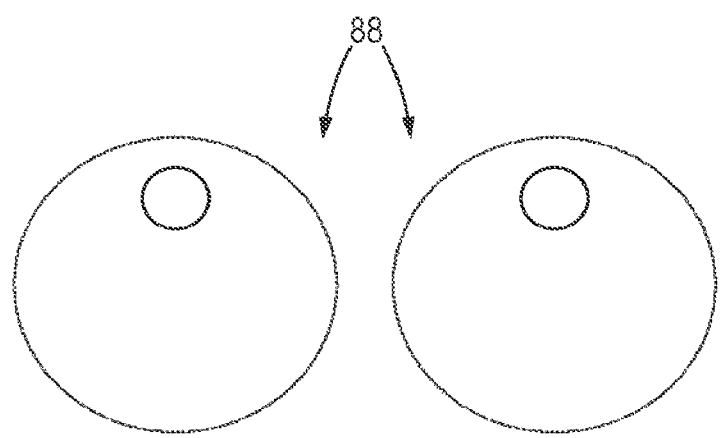

In another embodiment, the fastener interface 78 extends only partially through the implant 72. The fastener interface 78 may be located generally in the center of the implant, or it may be located eccentrically, as depicted in FIGS. 22A and 22B. In one embodiment, shown in FIGS. 23A and 23B, the fastener interface 78 is located at the edge 86 of the implant 76 such that the interior surface of the hole 78 is contiguous with the outer edge of the implant. This configuration of the fastener interface 78 does not require the cable 72 to be threaded through the fastener interface 78 and may facilitate engagement of the fastener member with the implant. FIGS. 24A and 24B depict an embodiment comprising a two-part implant 88. Either a single cable or two separate cables may be used retain both discs within the facet joint. FIGS. 25A and 25B depict another embodiment comprising a curved implant 90 with a fastener interface 78 adapted to accept a cable.

Figure 27A:
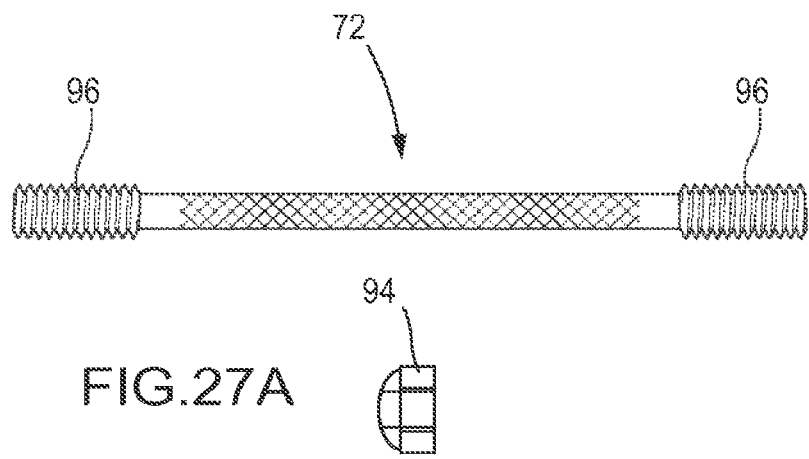
FIGS. 27A and 27B depict another embodiment of the fastener member comprising a braided cable with threaded ends adapted to accept threaded nuts.
Figure 27B:
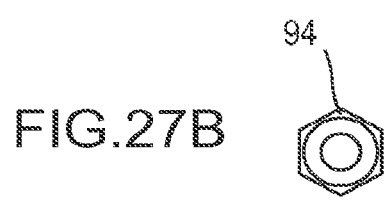
Figure 28:
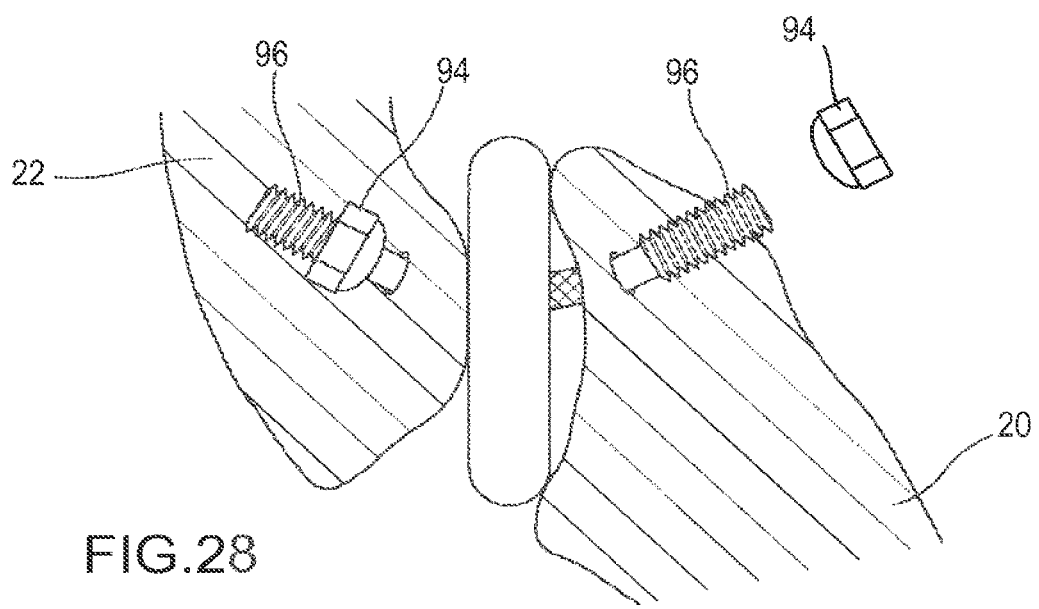
FIG. 28 depicts one embodiment where a cable is engaged to the articular processes using nuts threaded onto the cable.

In FIG. 26, the wire or cable 72 is secured to the articular processes 20, 22 by tying one or more knots 92 in the cable 72 that can resist pulling of the wire or cable through the articular process. In another embodiment, one or both ends of the wire or cable are provided with an anchor to resist migration of the implants. As shown in FIGS. 27A and 27B, one or both ends of the wire or cable 72 may be threaded such that a nut 94 can be tightened on the wire or cable 72 to secure the wire or cable to the articular processes 20, 22. FIG. 28 depicts the attachment of a nut onto a threaded end of a cable. The threaded portion 96 of the wire or cable can be secured to the cable by pressing, crimping or twisting the threaded 96 portion onto the cable 72. In one embodiment, the threaded portion 96 is made from titanium, titanium alloy, cobalt chromium, stainless steel, or any combination thereof.

In one embodiment, the wire or cable has two threaded ends 96 for engaging the bony or cartilaginous tissue, one portion for each facet of the facet joint.

Figure 29:
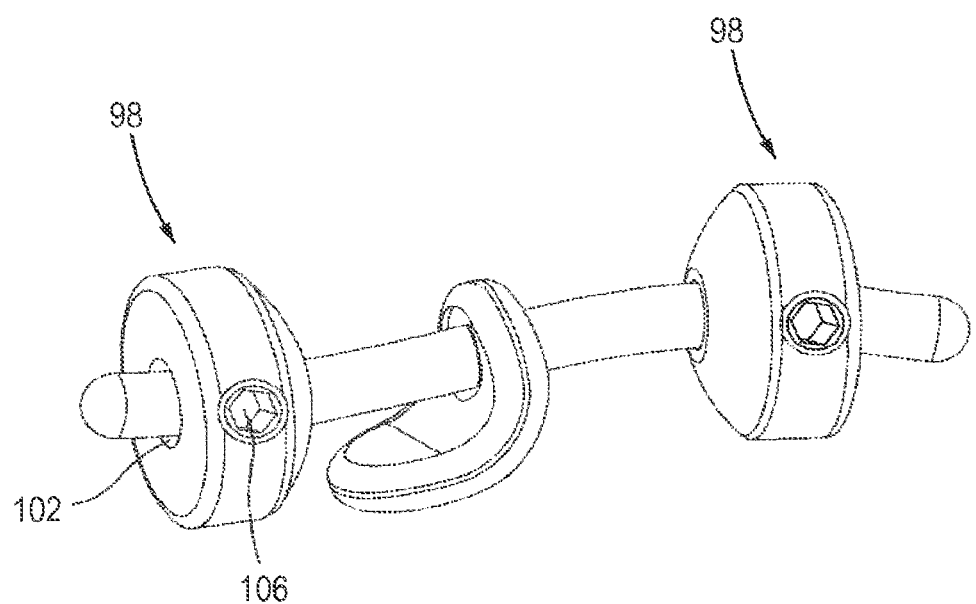
FIG. 29 depicts a preferred embodiment comprising a curved implant, cable and two set-screw fastener rings.

In another embodiment, shown in FIG. 29, the wire or cable is secured to the articular process with fastener rings 98. As depicted in FIGS. 30A and 30B, the fastener rings 98 comprise a ring 100 with a central lumen 102 and a locking element to facilitate locking the ring 100 to a fastener member. The central lumen 102 is adapted to accept insertion of a wire or cable through it. The illustrated locking element is in the form of a side lumen 104 which is threaded and configured to accept a rotatable screw 106 with a proximal end 108, a threaded body 110 and a distal end 112. The threaded body 110 is complementary to the threads of the side lumen 104 so that when the screw 106 is rotated at its distal end 112, the proximal end 108 of the screw 106 moves further into the central lumen 102 and is capable of applying increasing force to a wire or cable inserted through the central lumen 102. In one embodiment, the force on the wire or cable is capable of creating a friction fit or a mechanical interfit to resist movement between the wire or cable and the fastener ring 98, thereby securing the wire or cable to the articular process 20 or 22. As shown in FIGS. 31 to 33, the distal end 112 of the screw 106 can be configured to engage the wire or cable in any of a variety designs, including but no limited to a blunt tip 114, curved tip 116 and piercing tip 118.

In another embodiment, depicted in FIGS. 34A and 34B, the wire or cable is securable to the articular process with a fastener ring 120 have radially inward biased projections 122 defining a central lumen 124. The central lumen has a cross-sectional shape smaller than that of the wire or cable but is capable of enlargement when the inward projections 122 are bent away, as shown in FIGS. 35A and 35B. The inward projections 122 apply increasing force to the wire or cable within the central lumen 124 as the projections 122 are bent, thereby creating a friction fit.

In one embodiment, one end of the wire or cable fastener member is preformed with a retainer for engaging the articular process. The retainer may be a preformed ring, bulb, flared end, T-bar end, or any of a variety of shapes having a greater cross sectional area than the other portions of the wire or cable fastener member. This configuration of the wire or cable fastener member is adapted to engage an articular process by passing the free end of a wire or cable fastener member through an articular process such that the end with the preformed retainer can engage the articular process.

In one embodiment, the wire or cable fastener member is secured to the articular processes with sufficient laxity or length between the secured ends or between the implant and one secured end so that the two articular processes are not fixed in position relative to each other and remain capable of performing movements such as flexion, extension, lateral flexion and/or rotation. In one embodiment, the fastener member comprises a cable of braided polymer, including but not limited to a braided polymer such as PEEK or PEKK, or a braided metal, such as braided cobalt chromium or titanium. The cable can be selected with different degrees of flexibility to provide different degrees of movement at that facet joint. The cable has a first segment capable of engaging the implant at its fastener interface to limit the movement.

Figure 36A:
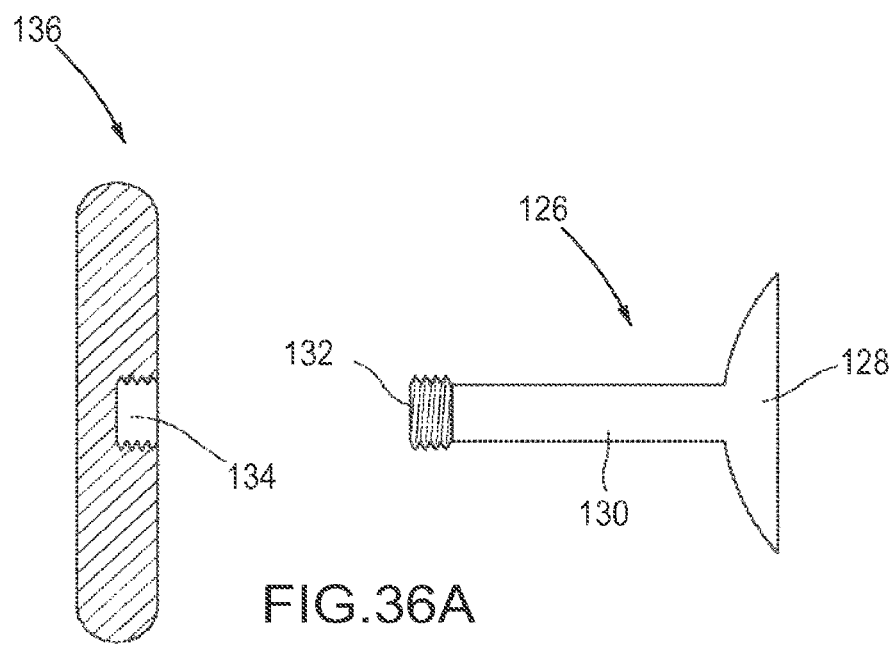
FIGS. 36A to 36C illustrate embodiments comprising a implant with a close-ended threaded fastener interface and a threaded fastener member.
Figure 36B:
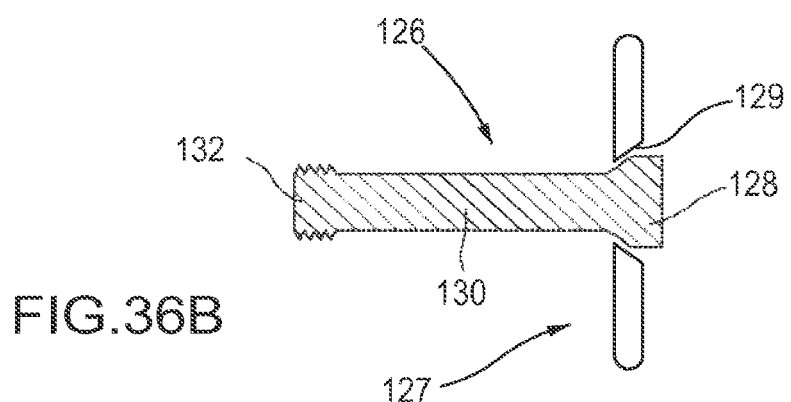
Figure 36C:
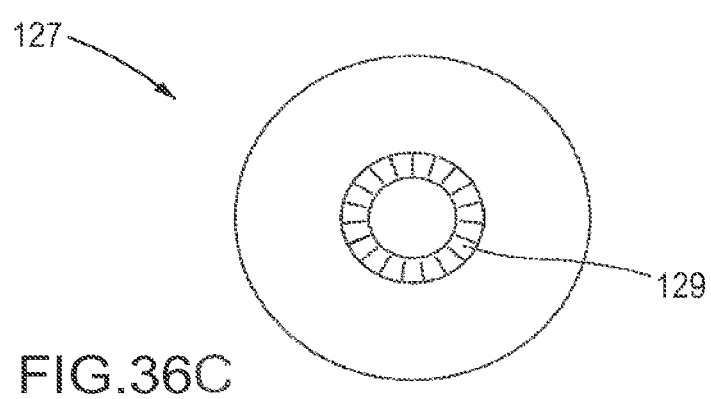

In one embodiment, shown in FIG. 36A, the fastener member comprises a screw or bolt 126 with a proximal end 128, body 130 and distal end 132. The distal end 132 of the screw or bolt is capable of forming a mechanical interfit with a complementary fastener interface 134 on the implant or spacer 136. The distal end 132 typically comprises threads, but other configurations may be used to form a mechanical interfit. The complementary fastener interface 134 on the implant 136 could be a threaded through hole or, a close-ended hole. The proximal end 128 of the screw or bolt 126 has a hex or other type of interface known in the art, capable of engaging a rotating tool to manipulate the screw or bolt 126. The body of the screw or bolt 126 has a length sufficient to at least span the length of the hole or conduit created through the articular process for securing the implant. In FIG. 36B, the fastener member further comprises a pivotable washer 127 with a pivot surface 129 that articulates with the proximal end 128 of the screw 126. In one embodiment, the pivotable washer 127 is capable of a range of positions relative to the screw 126 and provides the screw 126 with a better surface area contact with the bone.

Figure 37A:
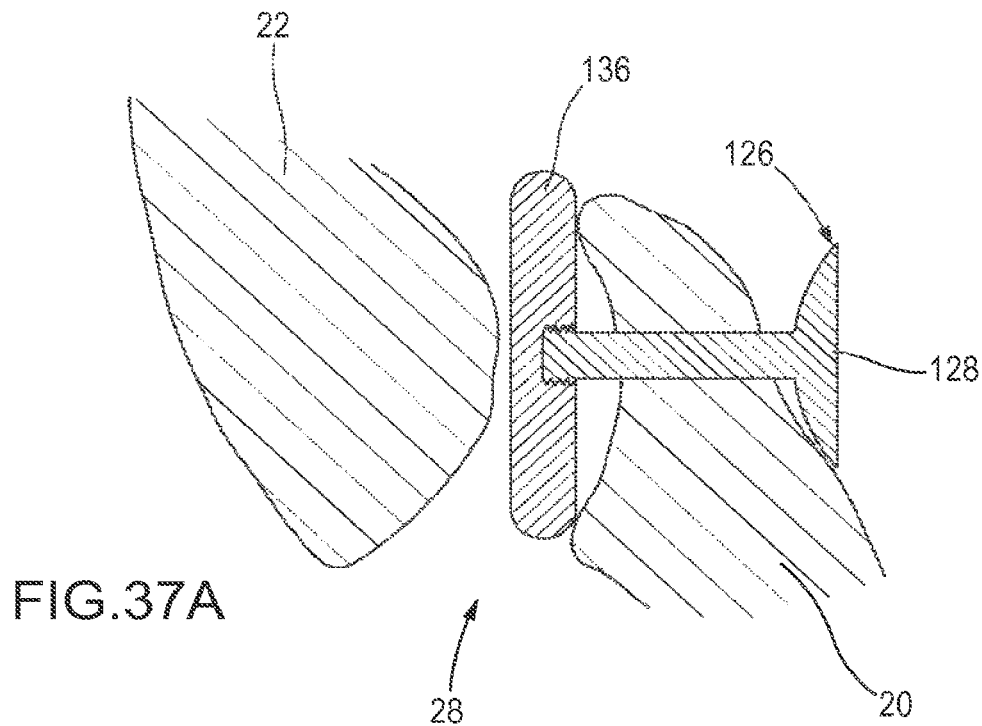
FIG. 37A is a cross sectional view of the implant in FIG. 36A implanted in a facet joint.
Figure 37B:
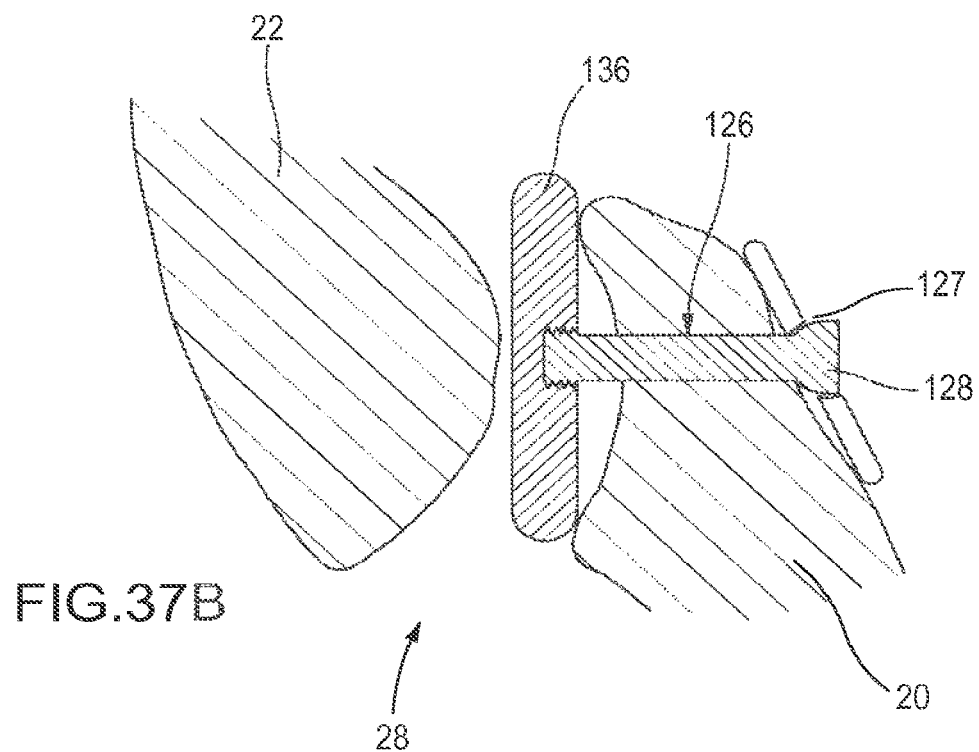
FIG. 37B is a cross sectional view of the implant in FIG. 36B implanted in a facet joint.
Figure 38:
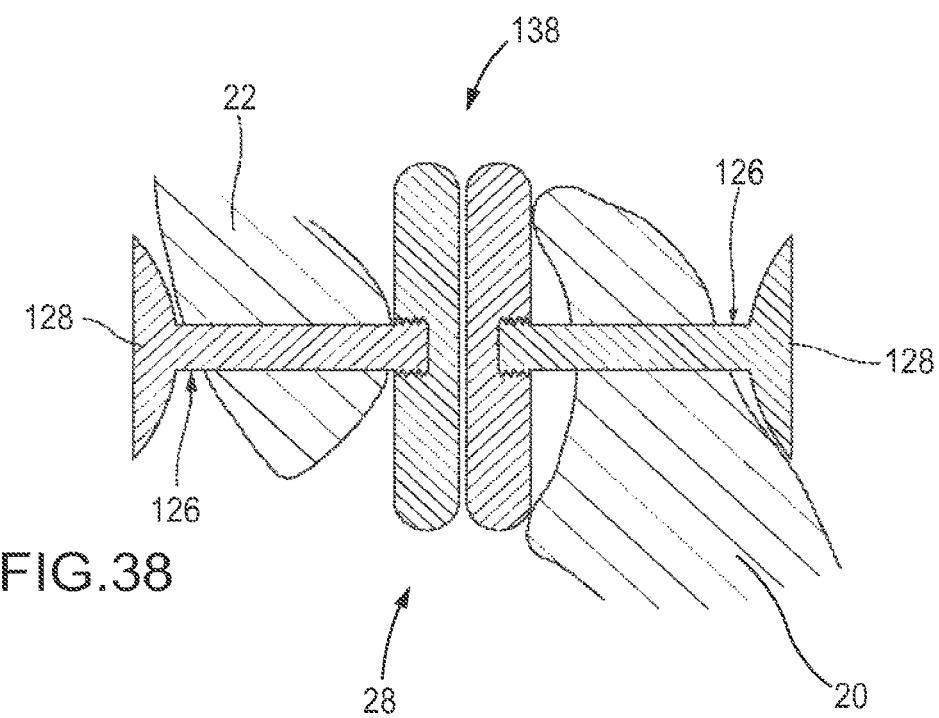
FIG. 38 is a cross sectional view of a two-part implant comprising flat discs implanted into a facet joint.
Figure 39:
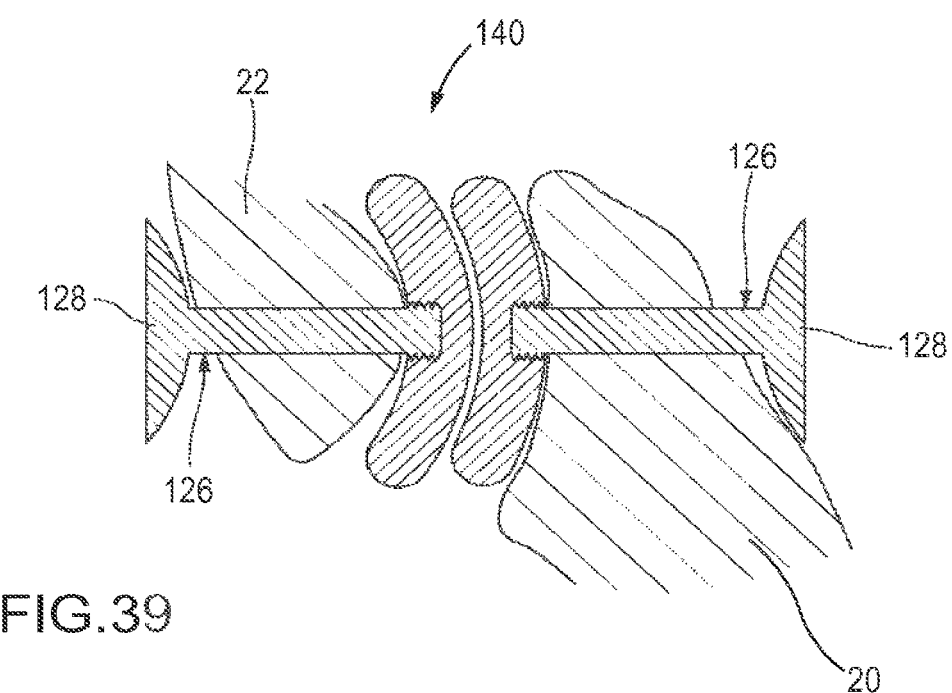
FIG. 39 is a cross sectional view of a two-part implant comprising curved discs implanted into a facet joint.
Figure 40A:
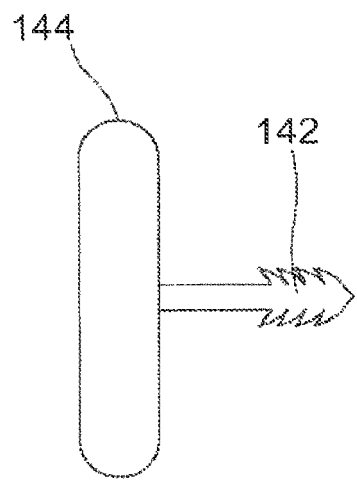
FIGS. 40A and 40B are schematic views of one embodiment of a facet joint implant with an integral fastener member comprising a centrally located barbed spike.
Figure 40B:
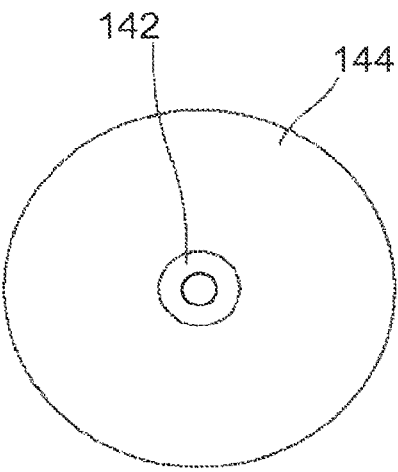
Figure 41A:
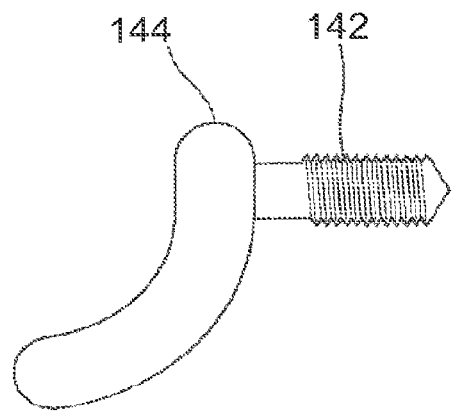
FIGS. 41A and 41B are schematic views of one embodiment of a facet joint implant with an integral fastener member comprising an eccentrically located barbed spike.
Figure 41B:
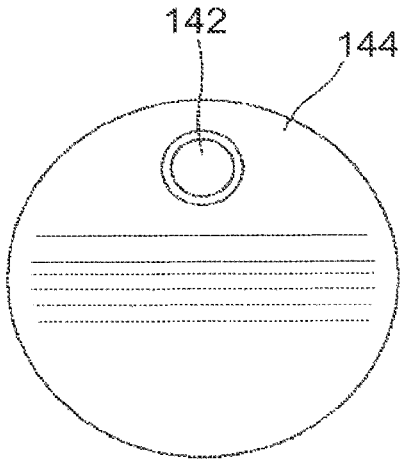

FIG. 37 is a cross-sectional view of a facet joint 28 with a spacer 136 bolted to one articular process 20 of a facet joint 28. The spacer 136 position is fixed relative to one facet 24 of the joint 28, but provides for spacing and movement of the other facet 26 with respect to the spacer 136. In embodiments comprising a two-part implant, shown in FIGS. 38 and 39, each disc may have its own screw or bolt fastener member. FIG. 38 depicts a flat two-part implant 138 and FIG. 39 depicts a curved two-part implant 140.

Figure 42:
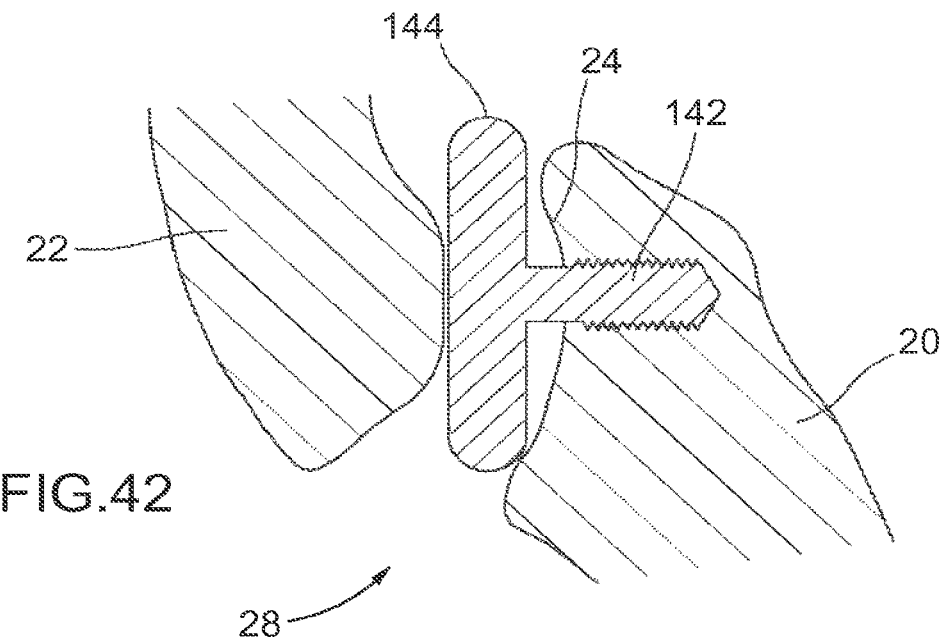
FIG. 42 depicts the implant of FIG. 41A implanted into a facet joint.
Figure 43:
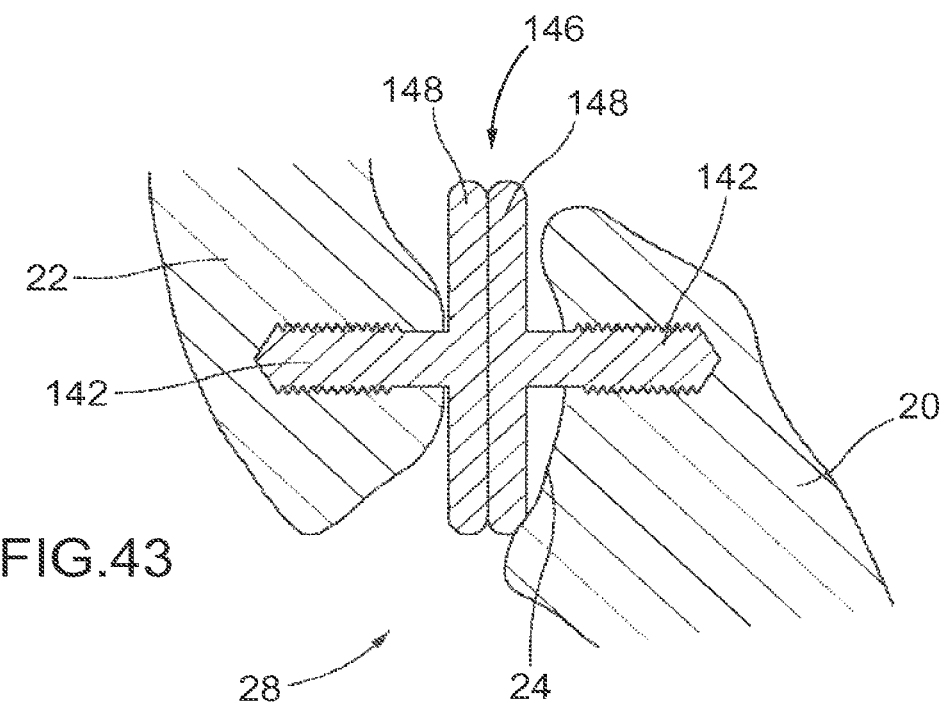
FIG. 43 illustrates a two-part implant implanted into a facet joint.
Figure 44:
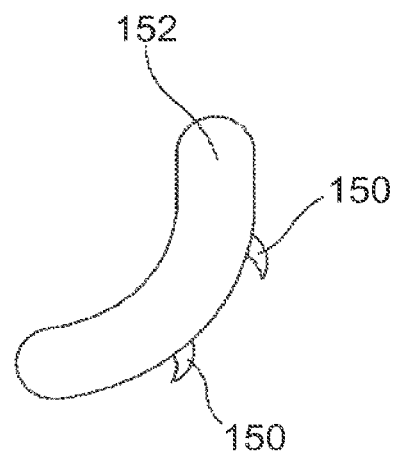
FIG. 44 shows one embodiment comprising a implant with multiple anchoring projections.
Figure 45:
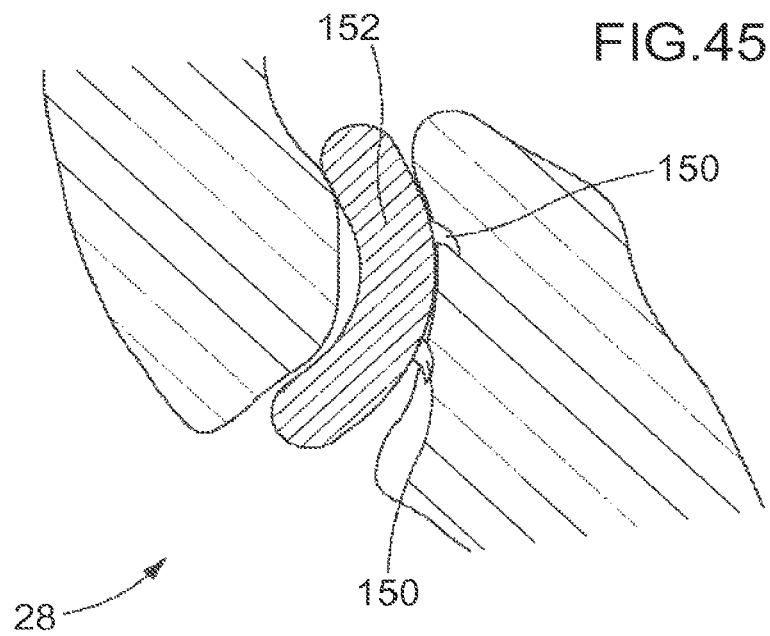
FIG. 45 shows the implant of FIG. 44 implanted into a facet joint.
Figure 46A:
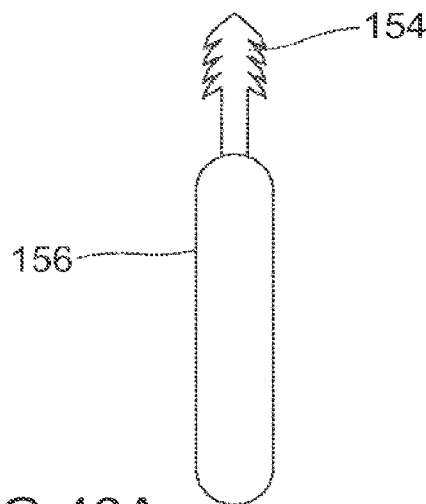
FIGS. 46A and 46B depict one embodiment comprising a implant with a rigid soft tissue side anchor.
Figure 46B:
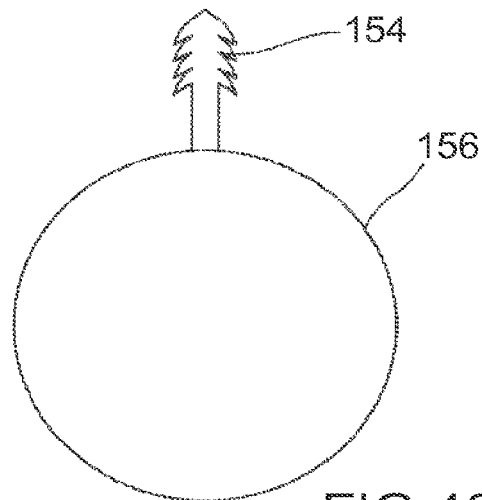

In some embodiments, shown in FIGS. 40A through 41B, the fastener member is integral with or attached to the implant and comprises a projection 142 from the implant 144 that is adapted to engage the adjacent articular process or surrounding tissue. In one embodiment, the projection comprises at least one spike 142 or hook projecting from one face of the implant 144. In one embodiment, the spike 142 or hook can be ribbed, barbed or threaded to resist separation after insertion into bone or tissue. FIG. 42 depicts the implant 144 of FIG. 40A engaged to a facet 24 of the facet joint 28. In one embodiment comprising a two-part implant 146, shown in FIG. 43, each disc 148 may have its own projection-fastener member 142. In some embodiments, as depicted in FIG. 44, more than one projection 150 is provided on the implant 152. FIG. 45 illustrates the implant of FIG. 44 placed in a facet joint 28. The projections 150 may be angled with respect to the implant 152 to resist dislodgement by the movement at the joint.

Figure 47A:
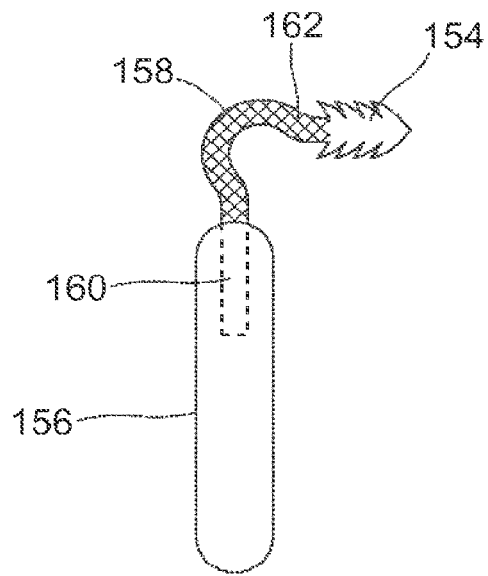
FIGS. 47A and 47B depict one embodiment comprising a implant with an embedded flexible soft tissue side anchor.
Figure 47B:
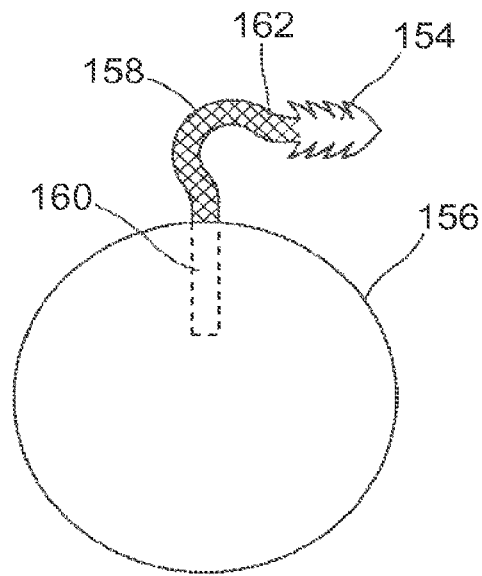

FIGS. 46A to 47B illustrate embodiments where the fastener member comprises a projection 154 extending laterally such as from the side of the implant 156, and adapted to engage the soft tissue surrounding the facet joint, rather than a bony or cartilaginous articular process. In one example, the implant of FIG. 46 could be inserted into a facet joint through an incision made in the joint capsule, but the integrity of the joint capsule opposite the incision site is maintained and used as an anchoring site for the implant. The orientation of the projection can be fixed as in FIG. 44, or flexible. FIG. 47 depicts a flexible tether such as a wire 158 with its proximal end 160 embedded in or otherwise attached to the implant and one or more barbs which may be attached to its distal end 162. A flexible projection may provide greater selection of soft tissue anchoring sites for the implant.

In one embodiment, the joint capsule is closed after placement of the implant. Closure may be performed using adhesives, suturing, stapling or any of a variety of closure mechanisms known in the art.

Figure 48A:
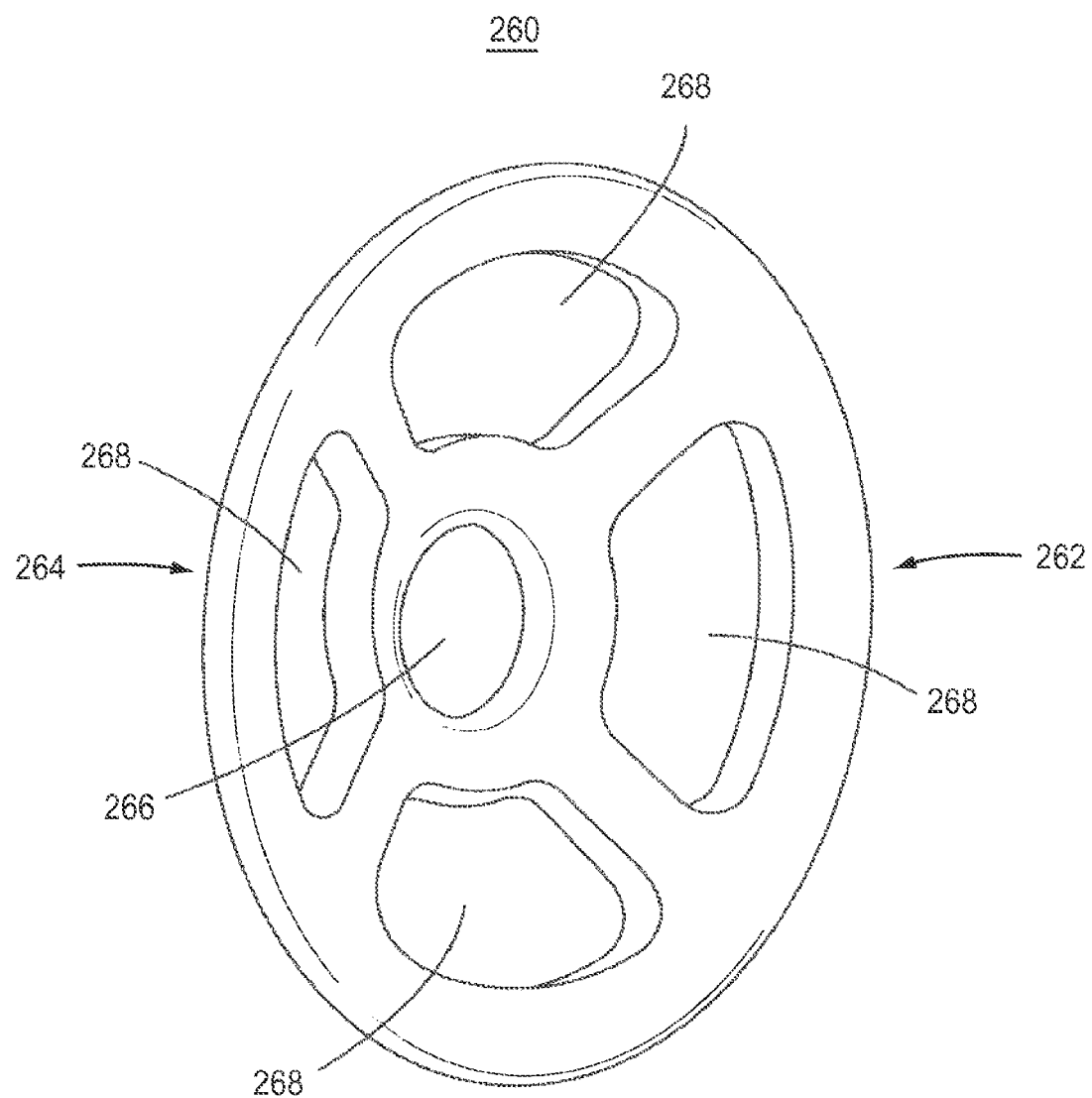
FIG. 48A is a perspective view of an implant according to an embodiment.
Figure 48B:
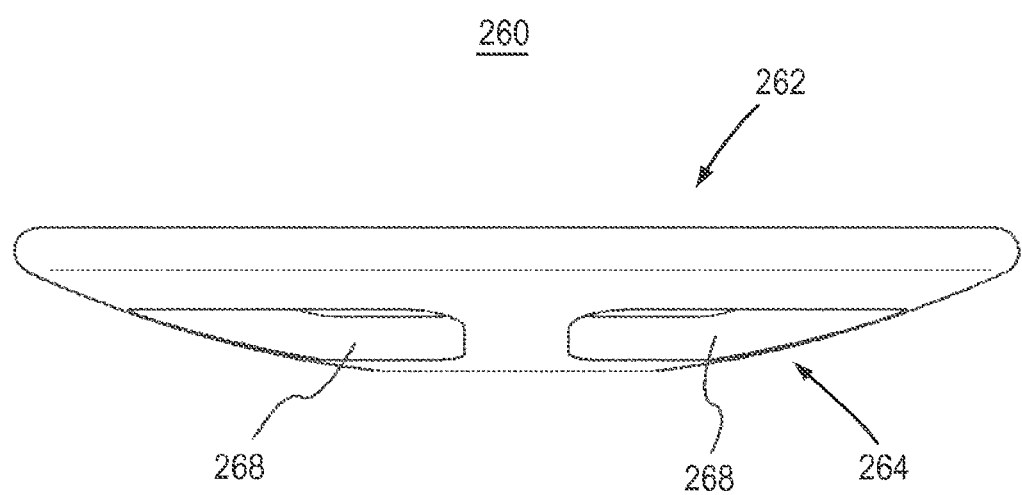
FIG. 48B is a side view of the implant of FIG. 48A.
Figure 48C:
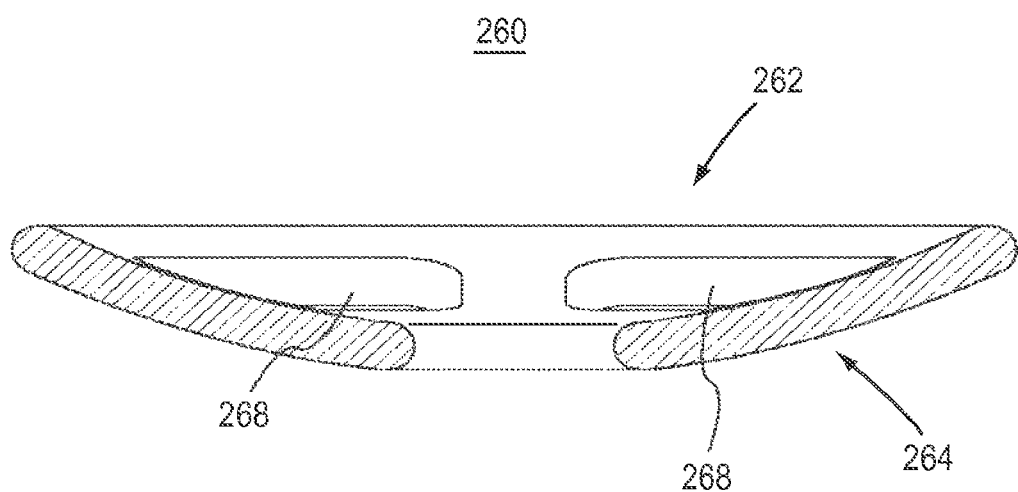
FIG. 48C is a cross-sectional side view of the implant of FIG. 48A.

FIGS. 48A-48C depict an implant 260 according to an embodiment. Specifically, FIG. 48A is a front perspective view of implant 260, FIG. 48B is a side view of implant 260, and FIG. 48C is a cross-sectional side view of implant 260. Implant 260 can be similar to, and have similar elements and uses as implant 160 described above. By way of example, a fastener interface 266 of implant 260 can be similar to fastener interface 166 of implant 160. Implant 260 includes a concave first face 262, a convex second face 264, a centrally disposed circular fastener interface 266, and four irregular shaped substance interfaces 268.

Figure 49:
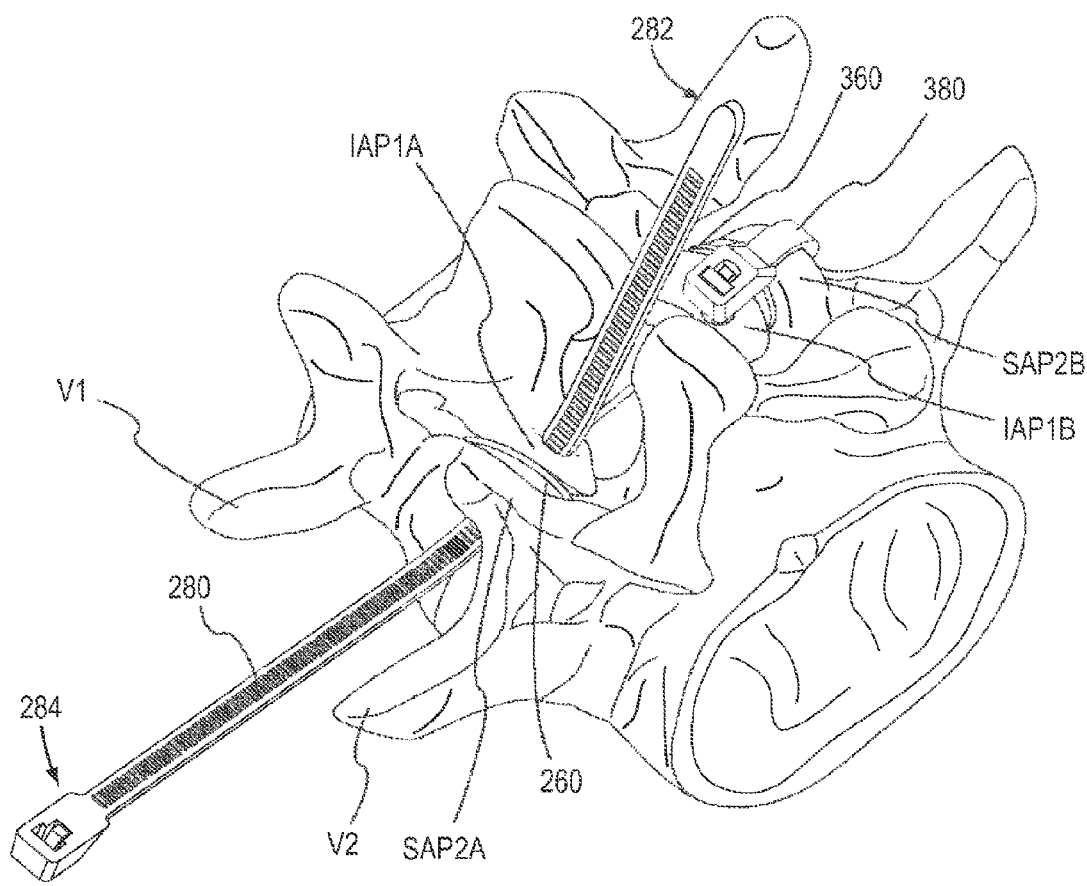
FIGS. 49-51 are posterior perspective views of a portion of the vertebral column depicting a method of stabilizing a vertebra using an implant and fastener member according to an embodiment.
Figure 50:
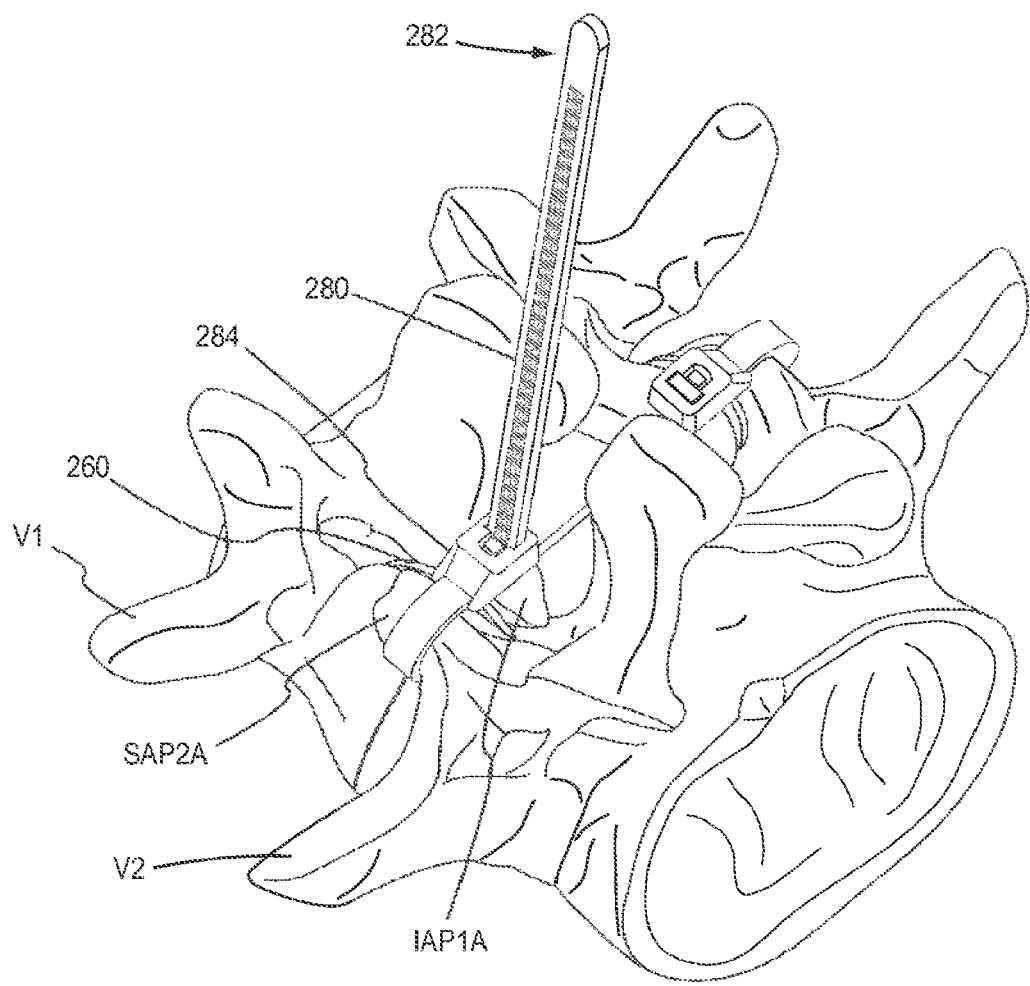
Figure 51:
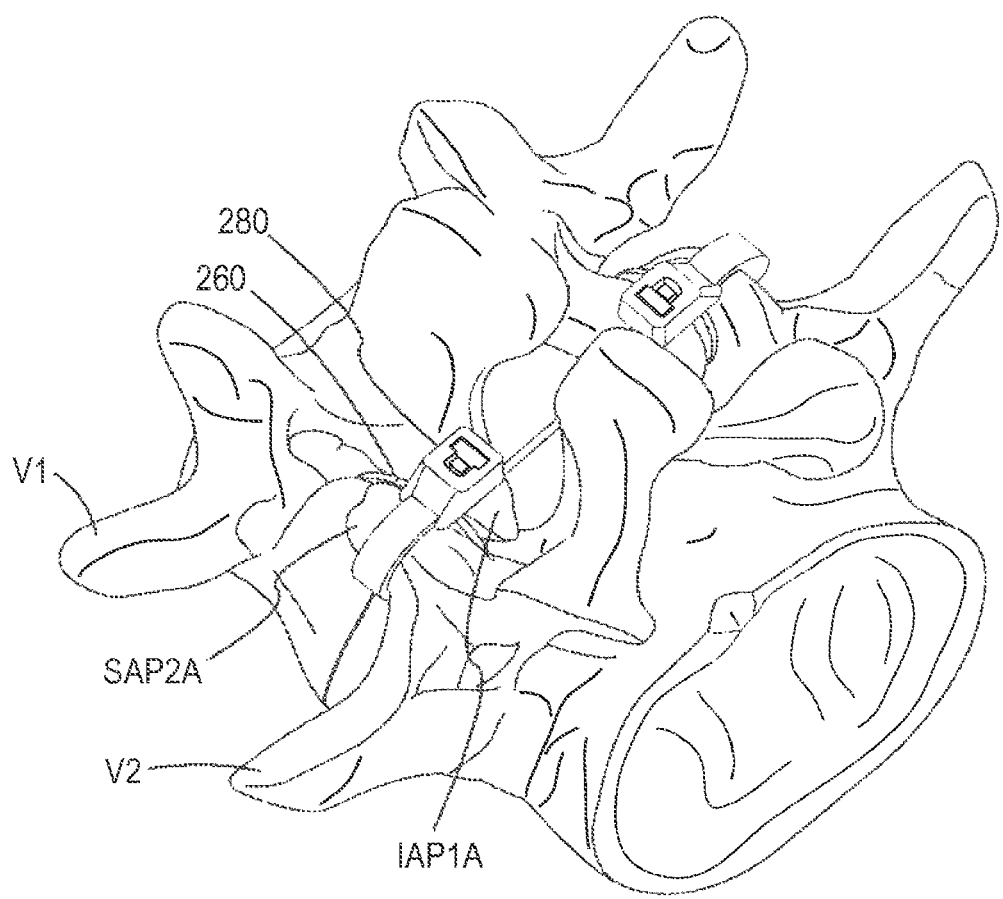

FIGS. 49-51 show posterior perspective views of a portion of the vertebral column during a method for fusing adjacent vertebrae using an implant 260 according to an embodiment. As shown in FIG. 49, implant 260 and a fastener member 280 can be used to fuse a vertebra V1 and vertebra V2 via the inferior articular process IAP of vertebra V1 and the superior articular process SAP2A of vertebra V2. Any fastener member can include any biocompatible material, e.g., stainless steel, titanium, PEEK, nylon, etc. Also as shown in FIG. 49, an implant 360 and a fastener member 380 are used to fuse a vertebra V1 and vertebra V2 via the inferior articular process IAP1B of vertebra V1 and the superior articular process SAP2B of vertebra V2. In some embodiments, vertebra V1 and/or vertebra V2 are fused using only one of implant 260 or implant 360. In some such embodiments, one of implant 260 and fastener member 280 or implant 360 and fastener member 380 can be used to stabilize vertebra V1 and/or vertebra V2 via one of via the inferior articular process IAP of vertebra V1 and the superior articular process SAP2A of vertebra V2, or, via the inferior articular process IAP1B of vertebra V1 and the superior articular process SAP2B of vertebra V2. In other such embodiments, one of fastener member 280 or fastener member 380 can be used to stabilize vertebra V1 and/or vertebra V2 via both of the inferior articular process IAP of vertebra V1 and the superior articular process SAP2A of vertebra V2 (for example, in combination with implant 260), and, the inferior articular process IAP1B of vertebra V1 and the superior articular process SAP2B of vertebra V2 (for example, in combination with implant 360).

Figure 52:
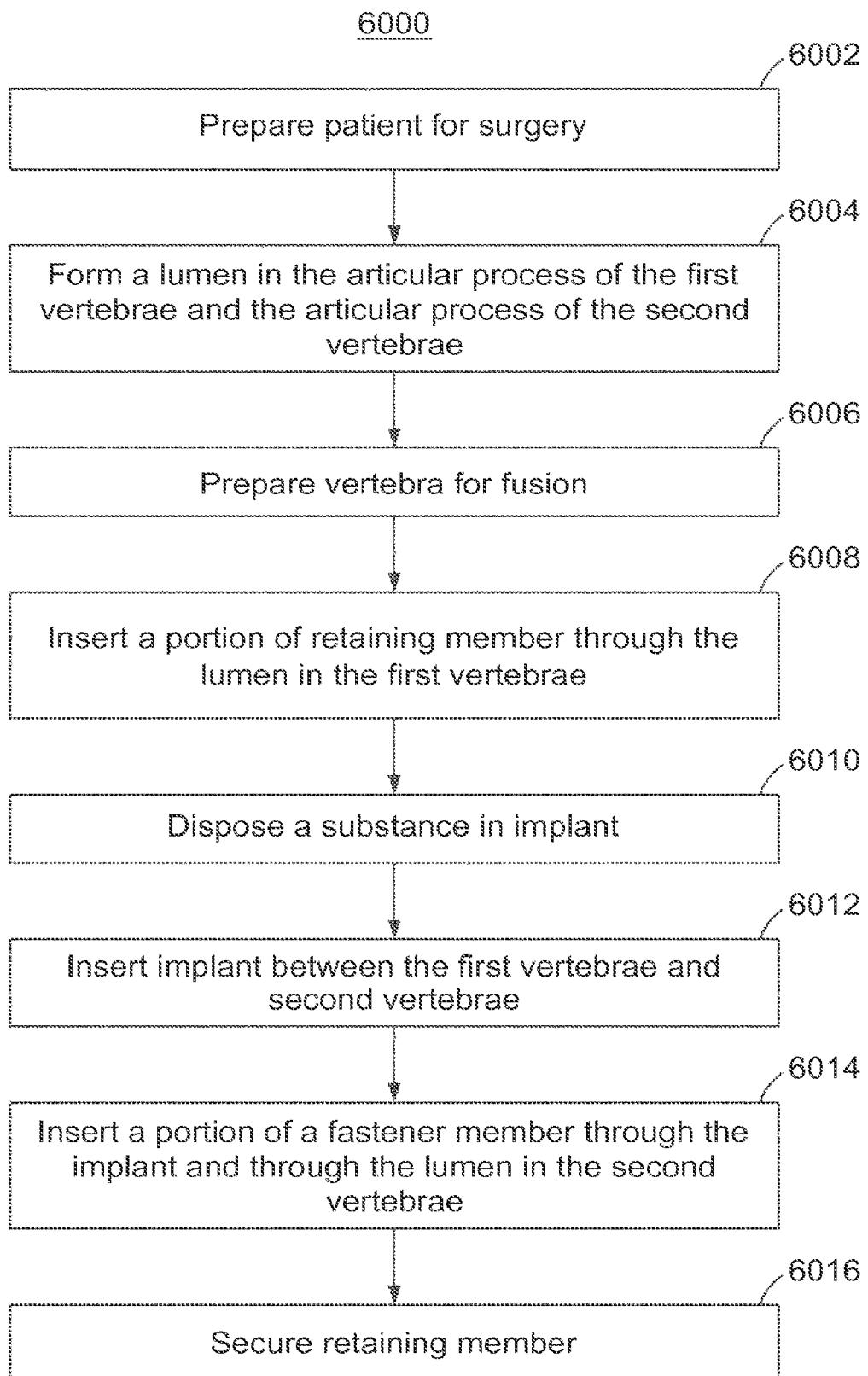
FIG. 52 is a flow chart illustrating a method of using the implant and fastener member depicted FIGS. 49-51.

FIG. 52 depicts a flow chart illustrating a method 6000 of using implant 260 with fastener member 280 and/or implant 360 with fastener member 380. Prior to use of implant 260 and/or implant 360, a patient can be prepared for surgery, at 6002. Some examples of preparations for surgery are described in U.S. patent application Ser. No. 12/859,009;

filed Aug. 18, 2010, and titled "Vertebral Facet Joint Drill and Method of Use" (referred to as "the '009 application"), and is incorporated herein by reference in its entirety. In addition to those procedures described in the '009 application, in some embodiments, the surgical procedure can include direct visualization of the vertebra(e) to be stabilized. Said another way, the medical practitioner can perform the operation without the use of fluoroscopy. This direct visualization can be possible due to the small incision necessary for implantation of the implant, for example, less than about 25 mm, and due to the ease of implanting and deploying the implant. In some embodiments, the surgical procedure used can include forming an opening in body tissue substantially equidistant between a first articular process of the first vertebra and a second articular process of the first vertebra. A cannula (not shown) can be inserted through the opening and a proximal end of the cannula can be positioned near the superior articular process SAP2A of vertebra V2. In some embodiments, the surgical procedure can include preparing the area near and/or around the vertebra V2 by, for example, removing all or a portion of ligaments, cartilage, and/or other tissue. For example, the area near and/or around a facet joint can be prepared by removing all or a portion of the facet joint capsule.

A drill or other device can be used to form a lumen in superior articular process SAP2A of vertebra V2 and inferior articular process IAP1A of vertebra V1, at 6004. Specifically, the drill can be used to form the lumen in a facet of superior articular process SAP2A of vertebra V2 and to form the lumen in a facet of inferior articular process IAP1A of vertebra V1. Methods and devices for forming lumens in vertebra are described in the '009 application. A portion of the surface of the facet of SAP2A and IAP1A can be prepared for fusion, at 6006. Specifically, a portion of the surface of the facet can be ground, scored, roughened, sanded, etc., such that the surface of the facet can better adhere to any substances to aid in fusion and/or otherwise fuse more readily to the implant. The fastener member 280 can be positioned within the cannula and can be advanced through the cannula until a proximal end portion 282 of fastener member 280 is positioned near the lumen of superior articular process SAP2A of vertebra V2. In some embodiments, the proximal end of the cannula can have a bend to direct the proximal end portion 282 of fastener member 280 into the lumen of superior articular process SAP2A of vertebra V2. The proximal end portion 282 of fastener member 280 is inserted into the lumen of superior articular process SAP2A of vertebra V2, at 6008. A substance can be disposed in a substance interface 268 of implant 260, at 6010. In some embodiments, implant 260 can have a substance disposed in substance interface 268 prior to a surgical procedure, for example, during manufacturing of implant 260, post-manufacturing, and/or as part of a kit. Implant 260 is inserted between the superior articular process SAP2A of vertebra V2 and inferior articular process IAP1A of vertebra V1, at 6012.

The proximal end portion 282 of fastener member 280 is inserted into the lumen of inferior articular process IAP1A of vertebra V1, at 6014. The fastener member can be secured, at 6016. Securing the fastener member 280 can be based on the type of fastener member used. By way of example, securing a fastener member similar to a flexible fastener band as depicted in FIGS. 49-51, can include inserting the proximal end portion 282 into a fastening mechanism of a distal end portion 284 of the fastener member 280, and advancing the proximal end portion 282 through the fastening mechanism to secure the fastening mechanism. In other embodiments, fastener member can be secured by tying a first portion the fastener member to a second portion of the fastener member, by screwing the fastener member into a threaded fastener interface, threading a fastener onto a threaded end of a fastener member disposed through a fastener interface, combinations of above, etc. In some embodiments, implant 260 can be disposed prior to inserting the proximal end portion of the fastener member 280 into the lumen of superior articular process SAP2A of vertebra V2. The cannula can be removed and/or reinserted at various points during the method 6000, including, for example, after the proximal end portion 282 of fastener member 280 is inserted into the lumen formed within the superior articular process SAP2A of vertebra V2, after vertebra V1 and/or Vertebra V2 has been stabilized, or at other points during method 6000.

After the fastener member is secured, superior articular process SAP2A of vertebra V2 can fuse to inferior articular process IAP of vertebra V1. Fusing can include one or more of bone material from superior articular process SAP2A of vertebra V2, bone material from inferior articular process IAP1A of vertebra V1, and the substance that fuses articular process SAP2A of vertebra V2 to inferior articular process IAP of vertebra V1 through substance interface 268. In some embodiments, after superior articular process SAP2A of vertebra V2 is fused to inferior articular process IAP1A of vertebra V1, the fastener member 280 is not removed. In some other embodiments, after superior articular process SAP2A of vertebra V2 is fused to inferior articular process IAP1A of vertebra V1, all or a portion of the fastener member 280 can be removed. In other embodiments, fastener member 280 can be removed after fusion of superior articular process SAP2A of vertebra V2 to inferior articular process IAP1A of vertebra V1 has started, but has not finished.

In addition to the fastener members shown above, such as, for example, fastener member 260, FIGS. 53-65 show fastener members according to other embodiments.

Figure 53:
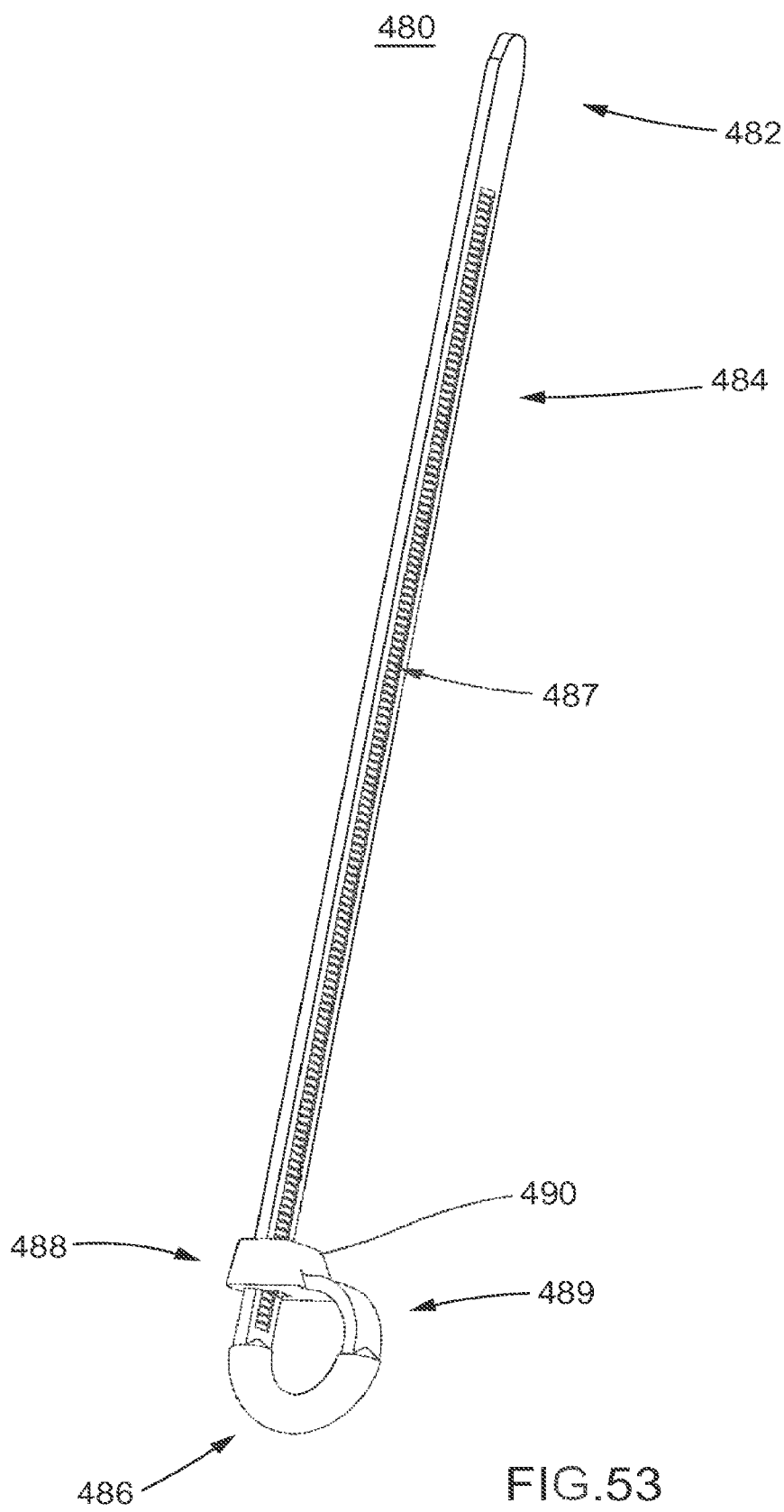
FIG. 53 is a perspective view of a flexible fastening band according to an embodiment.
Figure 54:
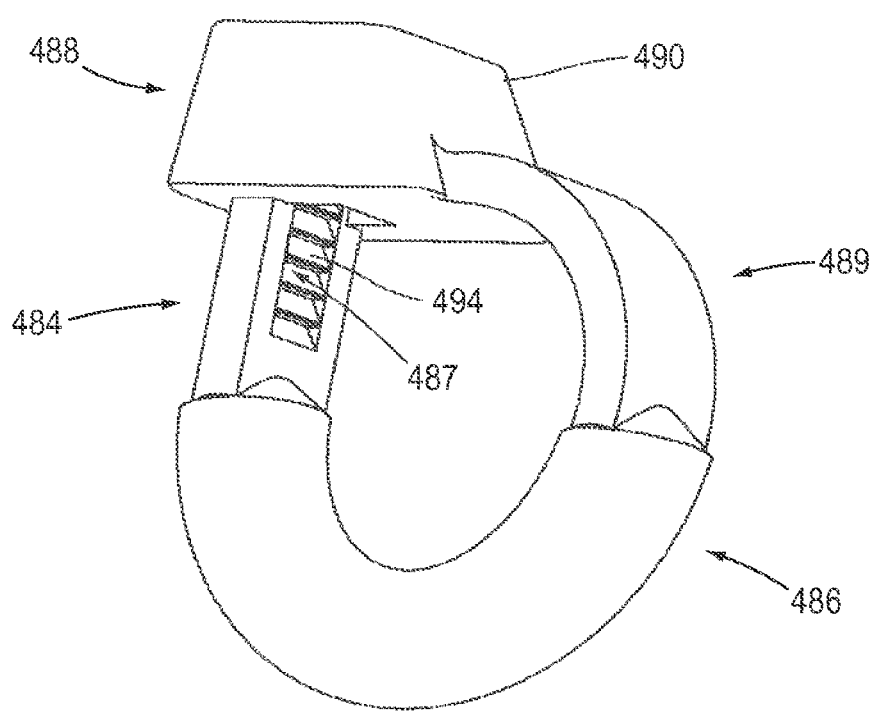
FIG. 54 is a perspective view of a portion of the flexible fastening band depicted in FIG. 53.

FIG. 53 depicts views of a fastener member 480. Fastener member 480 can be a flexible fastening band ("band") 480, FIG. 54 depicts a view of a portion of band 480 can be similar to band 280 described above and can include similar components. By way of example, band 480 includes a proximal end portion 482, a first portion 484, a second portion 486, and a distal end portion 488 including a fastening mechanism 490. In contrast to band 280, band 480 includes a cylindrical second portion 486 and each includes a third portion 489. As depicted in FIGS. 53-54, third portion 489 is substantially the same shape as first portion 482. As shown in FIGS. 53 and 54, band 480 includes a gear rack 487 and gears 494. Each of gears 494 can be wedge shaped to allow each of gears 494 to displace the ratchet of fastening mechanism 490 in only one direction. In some embodiments, gears 494 can be other shapes, such as blocks, etc.

Figure 55:
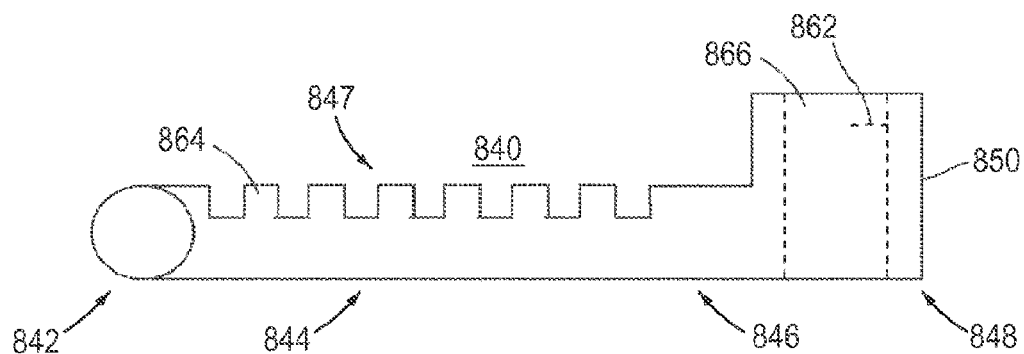
FIG. 55 is a side view of a flexible fastening band according to an embodiment.
Figure 56:
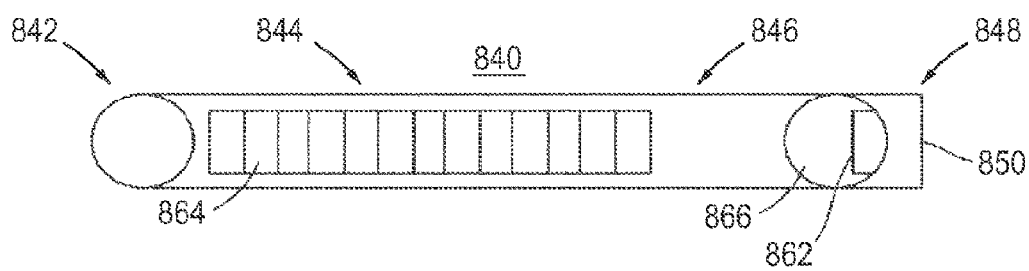
FIG. 56 is a top view the flexible fastening band depicted in FIG. 55.

FIG. 55 is a side view and FIG. 56 is a top view of a fastener member 840. Fastener member 840 can be a flexible fastening band ("band") 580 according to another embodiment. Band 840 can be similar to band 280 and band 480 described above and can include similar components. By way of example, band 840 includes a proximal end portion 842, a first portion 844 including a gear rack 847, a second portion 846, and a distal end portion 848 including a fastening mechanism 850 and a ratchet 862. In contrast to gear rack 487, a cross sectional area of each gear 864 of gear rack 847 is rectangular in shape instead of wedge shaped. Furthermore, in contrast to first portion 282, first portion 844 is cylindrical in shape instead of cuboidal in shape. In this manner, the lumen 866 of the fastening mechanism 850 is cylindrical in shape. A band according to this embodiment may be particularly useful in deployments where a single band in used to stabilize adjacent vertebrae. In this manner, the second portion can be disposed within the lumen of the first articular process of the first vertebra and a portion of the first portion can be disposed within the lumen of the second articular process of the first vertebra. In these embodiments the portion of the band within the first articular process of the first vertebra and the portion of the band within in the second articular process of the first vertebra can both have substantially the same shape as the lumen in the first articular process of the first vertebra and the lumen in the second articular process of the first vertebra. In this manner, and as described above regarding band 480, the amount of open space within the lumens can be minimized, the amount of surface area of the first portion and/or second portion of the band in contact with the lumens can increase, and subsequently the movement of the first vertebra and/or the second vertebra can be reduced or minimized. Furthermore, when movement of the first vertebra and/or the second vertebra does occur, forces acting against the band can be more equally distributed throughout the first portion and/or the second portion, due at least to the increased surface area of the band in contact with the lumens.

Figure 57:
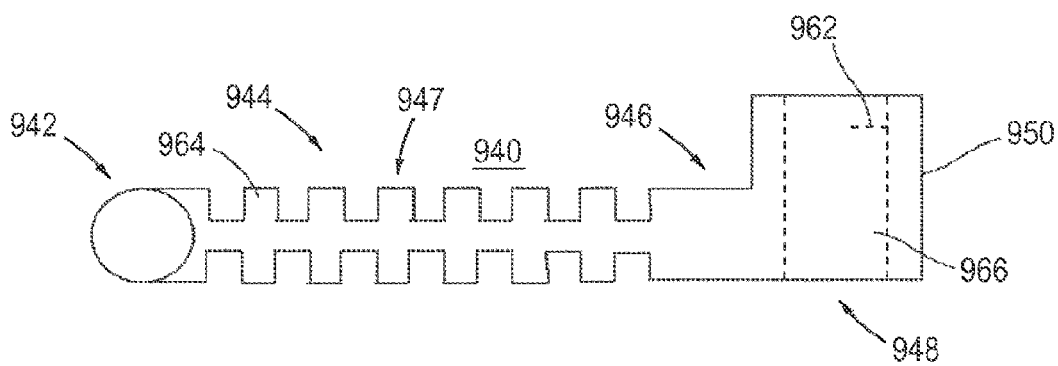
FIG. 57 is a side view of a flexible fastening band according to an embodiment.

FIG. 57 is a side view a fastener member 940. Fastener member 940 can be a flexible fastening band ("band") 940 according to an embodiment. Band 940 can be similar to band 280, band 480, and band 840 described above and can include similar components. By way of example, band 840 includes a proximal end portion 942, a first portion 944 including a gear rack 947, a second portion 946, and a distal end portion 948 including a fastening mechanism 950. Similar to gear rack 847, a cross sectional area of each gear 964 of gear rack 947 is rectangular in shape. In contrast to gear rack 847, each of gears 964 extend the entire circumference of first portion 944 instead of only a portion of the circumference of first portion 944. Furthermore, in contrast to first portion 282, but similar to first portion 844, first portion 944 is cylindrical in shape instead of cuboidal in shape. In this manner, the lumen 966 of the fastening mechanism 950 is cylindrical in shape. A band according to this embodiment may be particularly useful in deployments where the movement and repositioning of the band after implantation may be difficult. In this manner, because each of the gears can be the entire circumference of the first portion and/or the second portion, the first portion and/or the second portion can enter the fastening mechanism in any radial orientation and still engage the ratchet.

Figure 58:
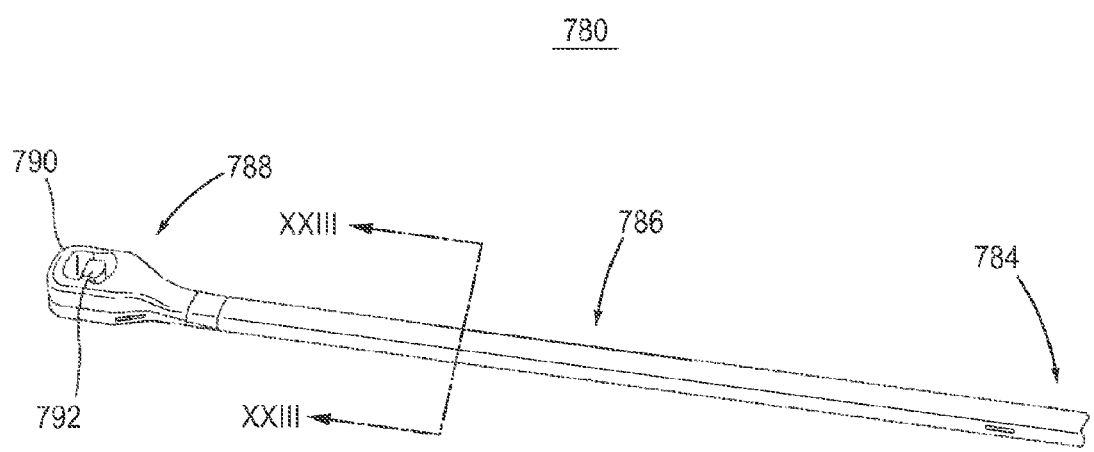
FIG. 58 is a perspective view of a flexible fastening band according to an embodiment.
Figure 59:
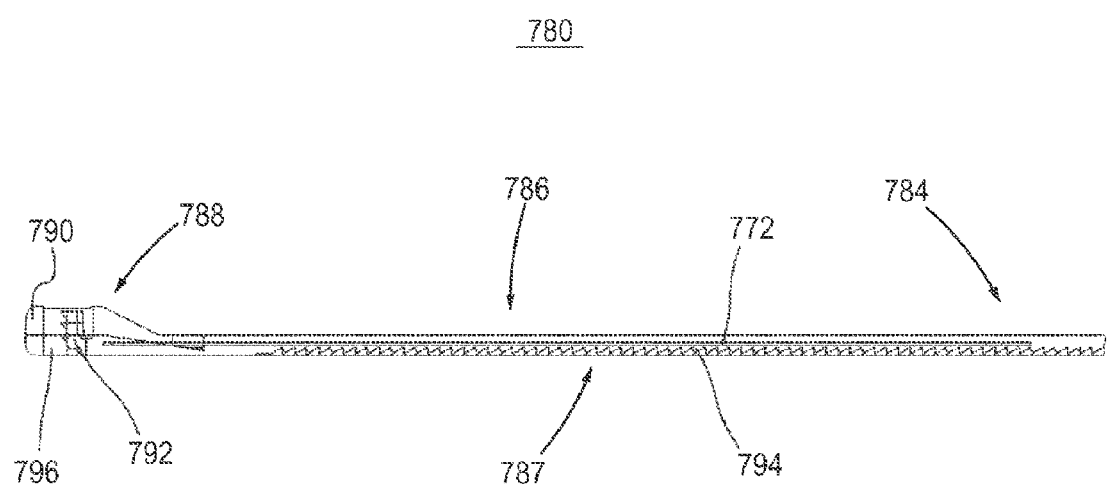
FIG. 59 is a cross-sectional side view of the flexible fastening band depicted in FIG. 58.
Figure 60:
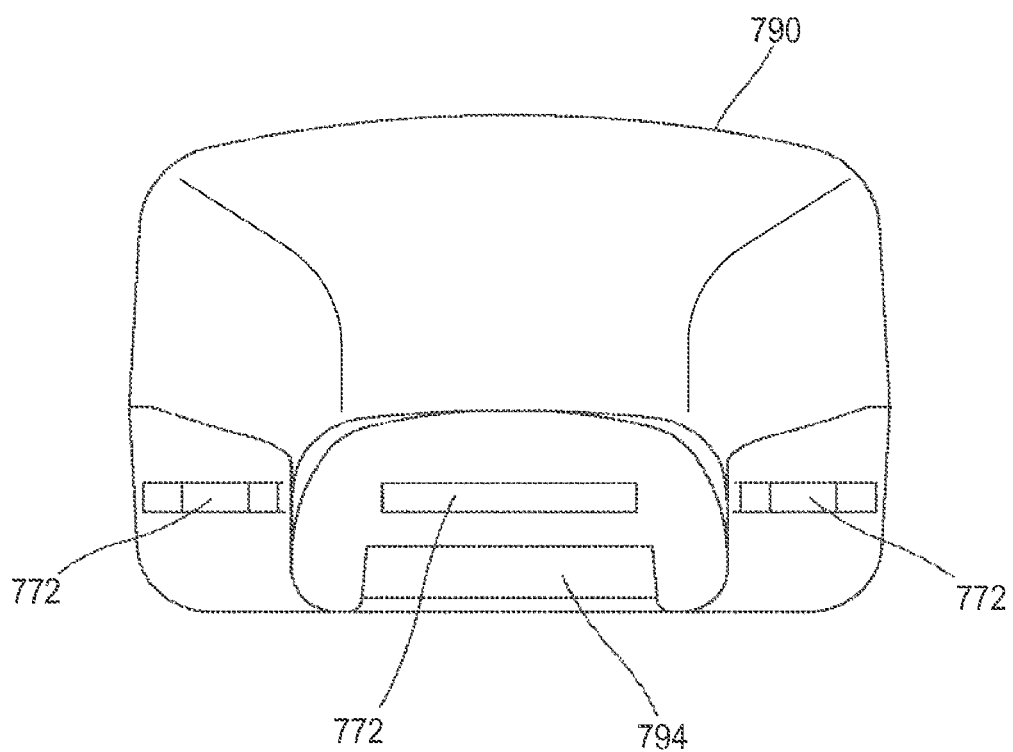
FIG. 60 is a cross-sectional view taken along line XXIII of the flexible fastening band depicted in FIG. 58.
Figure 61:
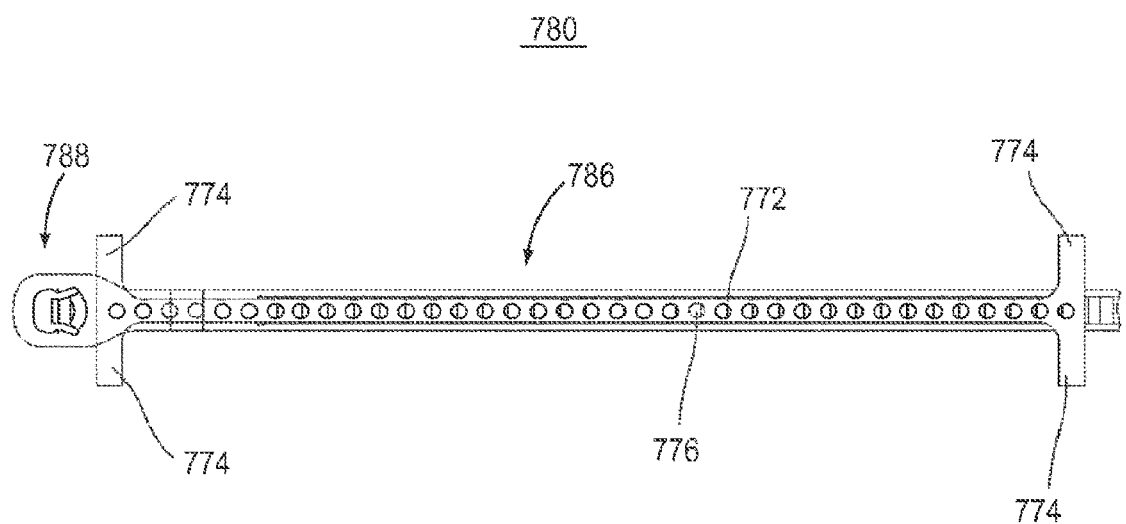
FIG. 61 is a cross-sectional top view of the flexible fastening band depicted in FIG. 58 in a first configuration.
Figure 62:
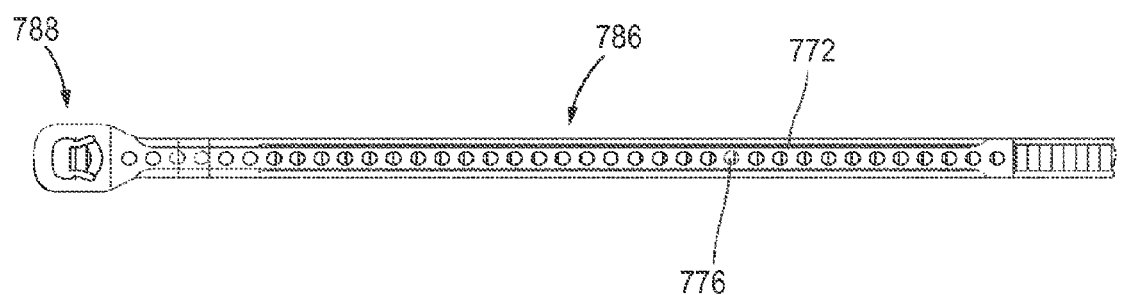
FIG. 62 is a cross-sectional top view of the flexible fastening band depicted in FIG. 58 in a second configuration.

FIGS. 58-62 are views of a fastener member 780. Fastener member 780 can be a flexible fastening band ("band") 780 according to another embodiment. FIG. 58 is a perspective view and FIG. 59 is a cross-sectional side view of band 780. FIG. 60 is a cross-sectional view of band 780 taken along line XXIII FIG. 61 is a cross-sectional top view of band 780 in a first configuration and FIG. 62 is a cross-sectional top view of band 780 in a second configuration. Band 780 can be similar to band 280 and band 480 described above and can include similar components. By way of example, band 780 includes a proximal end portion (not shown), a first portion 784 including a gear rack 787 (see FIG. 59), a second portion 786, and a distal end portion 788 including a fastening mechanism 790 and a ratchet 792. In contrast to band 280 and band 480, band 780 includes a reinforcement piece 772.

Reinforcement piece 772 can include any of the materials described above for a fastener member. In some embodiments, reinforcement piece 772 can include a material stronger than second portion 786 and/or first portion 784, for example, first portion 784 and second portion 786 can include PEEK and reinforcement piece 772 can include titanium. As shown in FIG. 59, reinforcement piece 772 can be disposed within band 780 approximately along the entire length of second portion 786, and a portion of reinforcement piece 772 can be disposed within the distal end portion 788. In some embodiments, reinforcement piece can include a length along at least a portion of the length of second portion 786 and/or first portion 784 but not the distal end portion. In some embodiments, reinforcement piece 772 can be disposed only within second portion 786. Reinforcement piece 772 can have a length in first dimension (length), a length in a second dimension (width), and a length in a third dimension (height). As described herein, a reinforcement piece be different shapes that can include more or fewer dimensions.

The reinforcement piece can be molded within the band. Said another way, in embodiments where the first portion, the second portion, and or the distal end portion are moldable materials, the reinforcement piece can be placed in the mold and the moldable materials can be injected or otherwise put in the mold around the reinforcement piece. In other embodiments, each portion of the band (for example, the proximal end portion, the first portion, the second portion, the third portion, and/or the distal end portion) around the reinforcement piece can have a top half and a bottom half, and each of the top half and the bottom half can be placed around the reinforcement piece, and sealed. As shown in FIG. 61, reinforcement piece 772 includes support members 774. While FIG. 61 shows reinforcement piece 772 including four support members 774, in some embodiments, more or fewer support members 774 can be used. Support members 774 can maintain the position of reinforcement piece 772 during the molding and/or assembly process of band 780. As shown in FIG. 62, support members 774 are removed before band 780 is used.

As shown in FIG. 60, reinforcement piece 772 can has a substantially uniform cuboidal shape. In other embodiments, reinforcement piece 772 can have other shapes. The shape of the reinforcement piece can be selected depending on the desired bending and/or torsion characteristics of the material chosen. By way of example, a substantially planar cuboidal shape can provide a greater increase in bending strength while providing a lesser increase in torsion strength, a cylindrical shape can provide an increase in bending strength while providing very little increase in torsion strength, a substantially square and/or tubular cuboidal shape can provide similar bending and torsion increases. Any shape can be selected to achieve the desired bending and torsion strength. Combinations of materials and shapes can also be considered. For example, a material having higher torsion strength may be combined with a shape having a lower torsion strength to combine for the desired torsion strength. As shown in FIGS. 61 and 62, reinforcement piece 772 includes holes 776 distributed along the length of the first dimension. While FIGS. 61 and 62 shows band 780 including many holes 776, in some embodiments, more or fewer holes 776 can be used. FIGS. 61 and 62 depict holes 776 distributed substantially equally along the length of the first dimension, in some embodiments, the holes can be distributed differently or along different dimensions depending on the shape and/or material chosen, and/or whether the reinforcement piece is solid or hollow. Holes 776 can be configured to reduce the weight of reinforcement piece 772 while still provided band 780 additional strength. Holes 776 can be round, oval, square, or any other shape.

Figure 63:
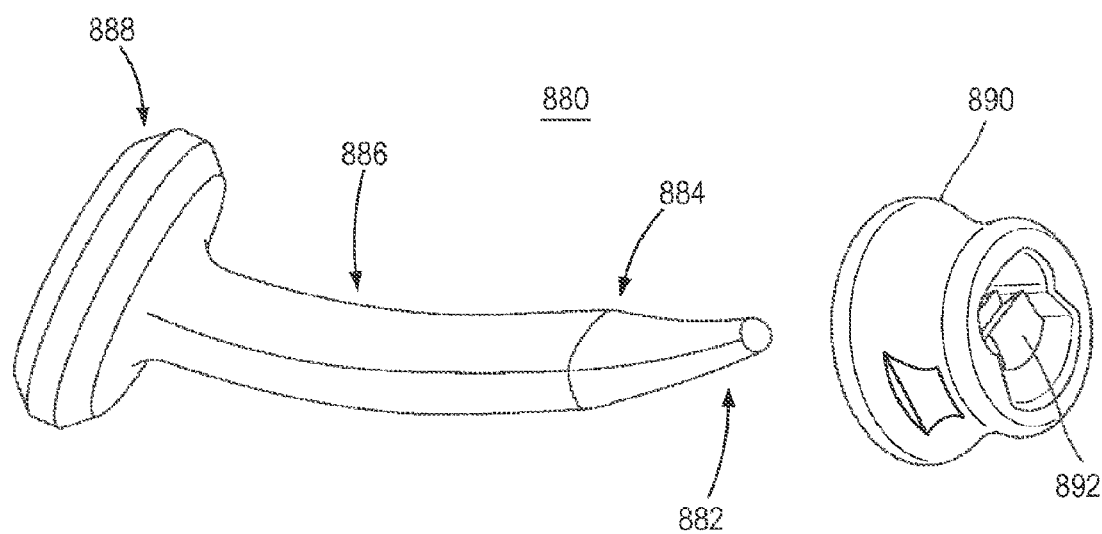
FIG. 63 is an exploded view of a flexible fastening band according to an embodiment.
Figure 64:
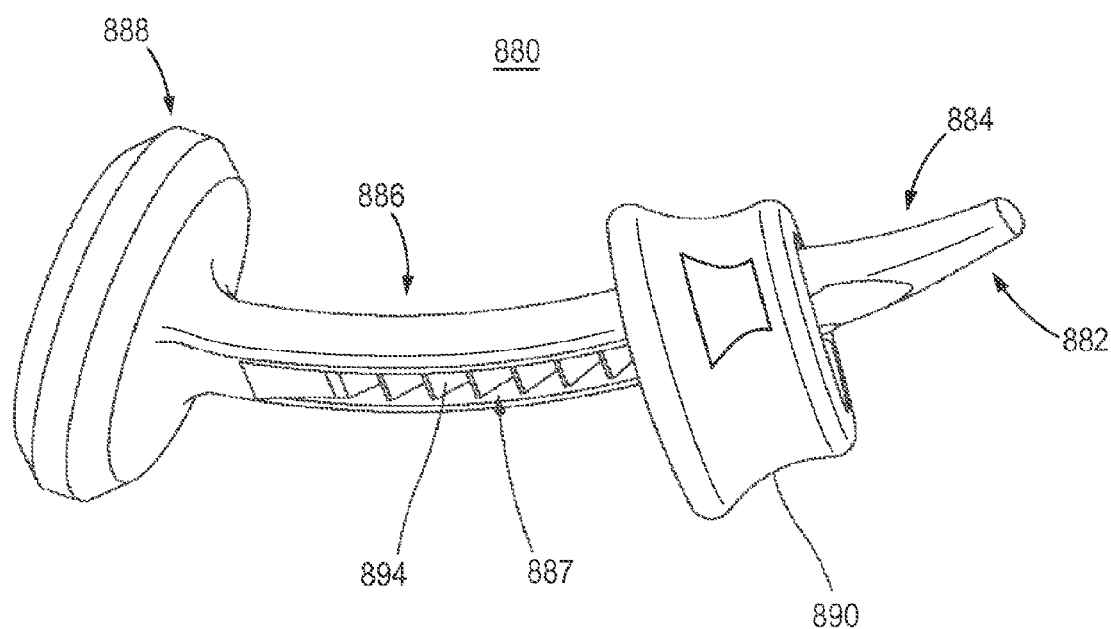
FIG. 64 is a perspective view of the flexible fastening band depicted in FIG. 63.
Figure 65:
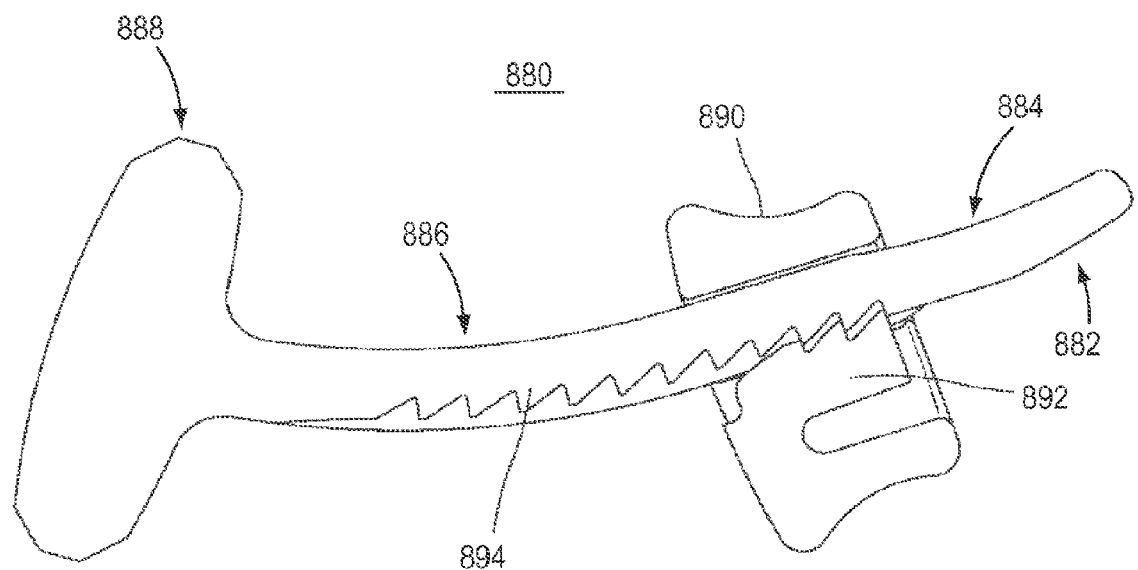
FIG. 65 is a cross-sectional view of the flexible fastening band depicted in FIG. 64.

FIG. 63 is an exploded view, FIG. 64 is a perspective view, and FIG. 65 is a cross-sectional view of a fastener member 880. Fastener member 880 can be a flexible fastening band ("band") 880 according to another embodiment. Band 880 can be similar to band 280 and band 480 described above and can include similar components. By way of example, band 880 includes a proximal end portion 882, a first portion 884, a second portion 886 including a gear rack 887, a distal end portion 888, a fastening mechanism 890 and a ratchet 892. In contrast to band 280 and band 480, the fastening mechanism 890 of band 880 is separately formed from distal portion 888 of band 880. While second portion 886 of band 880 is shown in FIGS. 63-65 as having a substantially cuboidal shape, in some embodiments, second portion 886 can be substantially cylindrical in shape or any other appropriate shape discussed herein. As shown in FIGS. 64 and 65, band 880 includes a gear rack 887 and gears 894. Each of gears 894 can be wedge shaped to allow each of gears 894 to displace a ratchet 892 of fastening mechanism 890 in only one direction. In some embodiments, gears 894 can be other shapes, such as blocks, or any other appropriate shape discussed herein. As shown in FIGS. 63-65, distal end portion 888 can be substantially circular in shape and can have a diameter greater than a width of second portion 886. In other embodiments, distal portion 888 can have other shapes, for example, oval, rectangular, square, etc.

In addition to the implants shown above, such as, for example, implant 160, FIGS. 66-81 show implants according to other embodiments.

Figure 66:
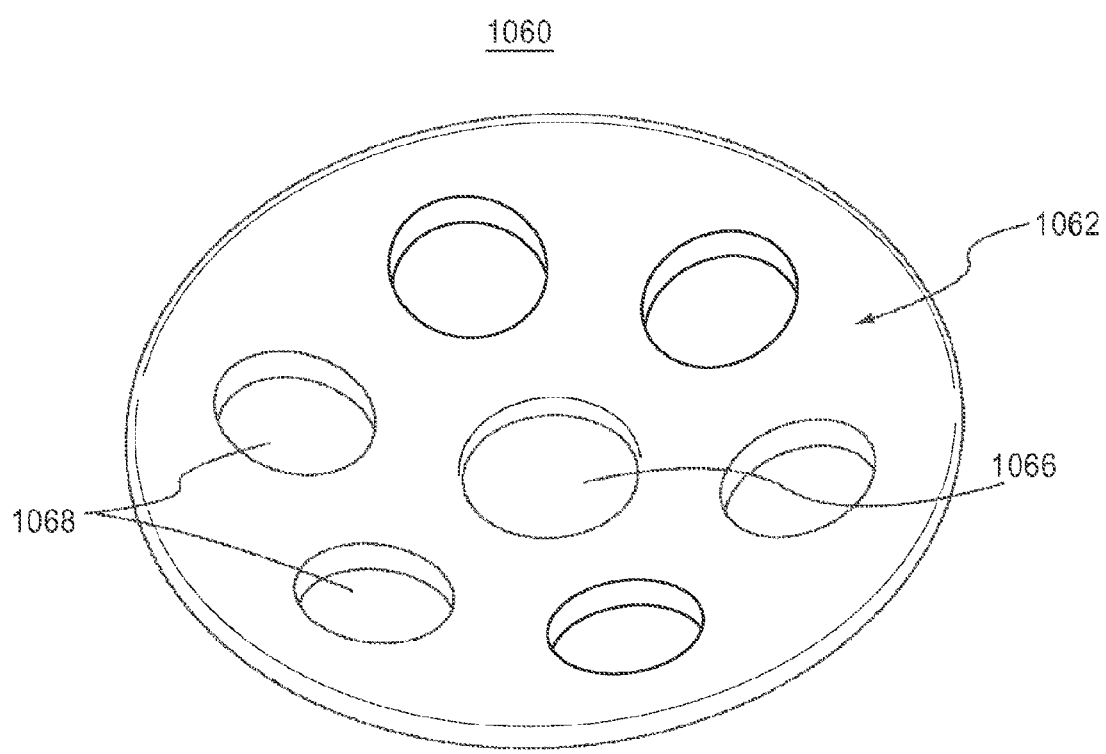
FIG. 66 is a front perspective view of implant according to an embodiment.
Figure 67:
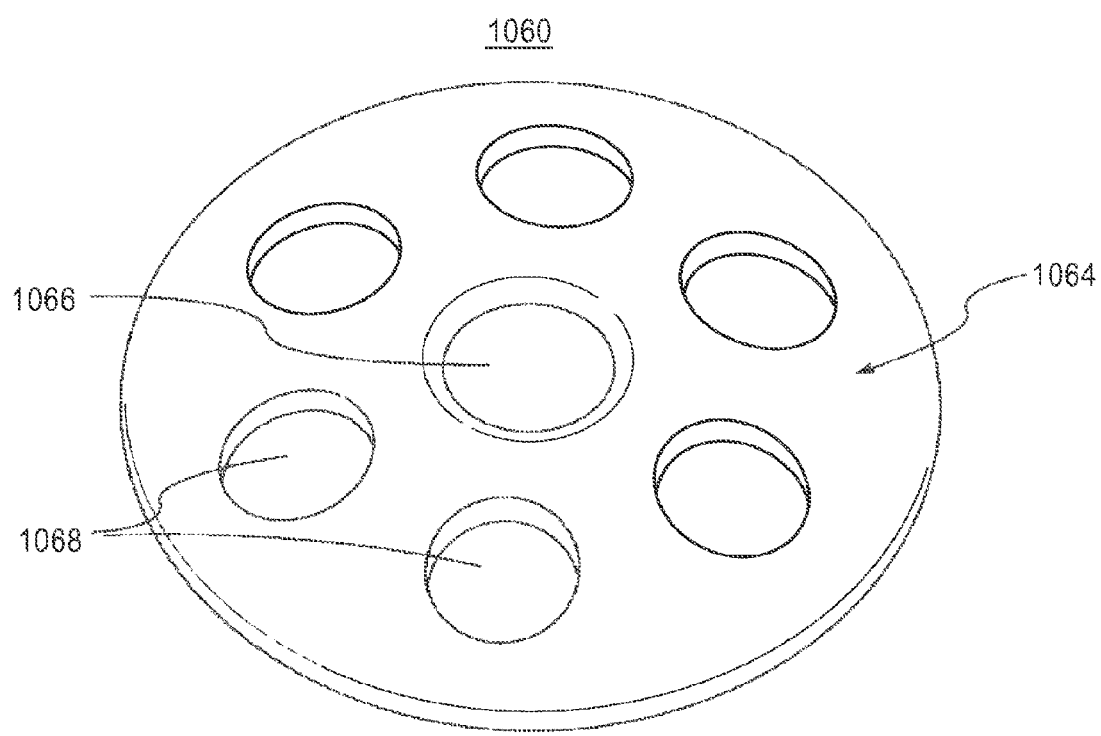
FIG. 67 is a rear perspective view of the implant of FIG. 66.
Figure 68:
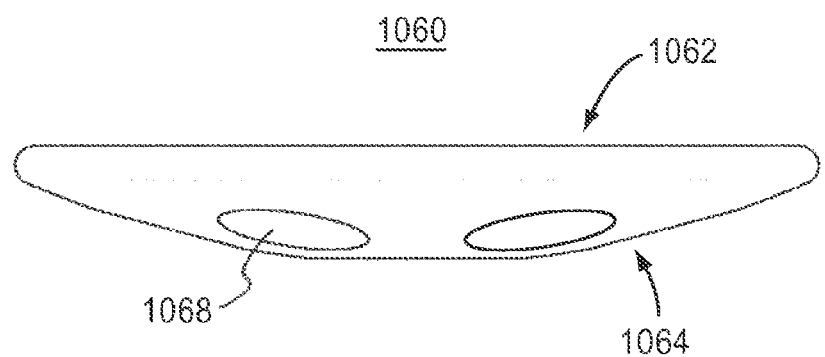
FIG. 68 is a side view of the implant of FIG. 66.
Figure 69:
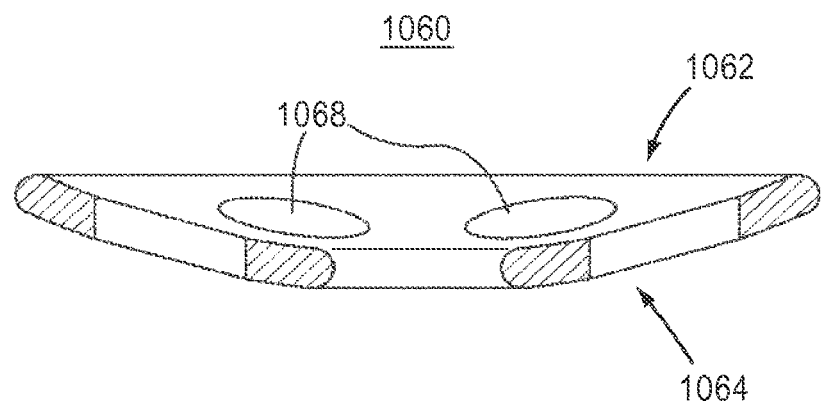
FIG. 69 is a cross-sectional side view of the implant of FIG. 66.

FIGS. 66-69 depict an implant 1060 according to an embodiment. Specifically, FIG. 66 is a front perspective view of implant 1060, FIG. 67 is a rear perspective view of implant 1060, FIG. 68 is a side view of implant 1060, and FIG. 69 is a cross-sectional side view of implant 1060. Implant 1060 can be similar to, and have similar elements and uses as implant 160 and implant 260 described above. By way of example, a fastener interface 1066 of implant 1060 can be similar to fastener interface 166 of implant 160, and similar to fastener interface 266 of implant 260 Implant 1060 includes a concave first face 1062, a convex second face 1064, a centrally-disposed substantially-circular fastener interface 1066, and six substantially-circular shaped substance interfaces 1068.

Figure 70:
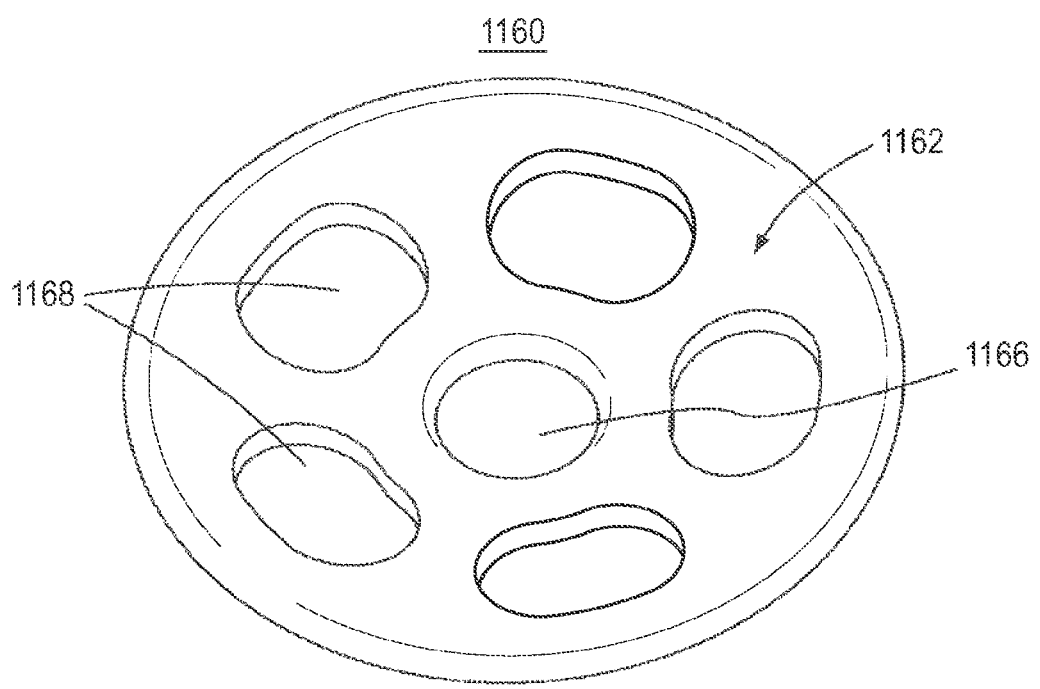
FIG. 70 is a front perspective view of implant according to an embodiment.
Figure 71:
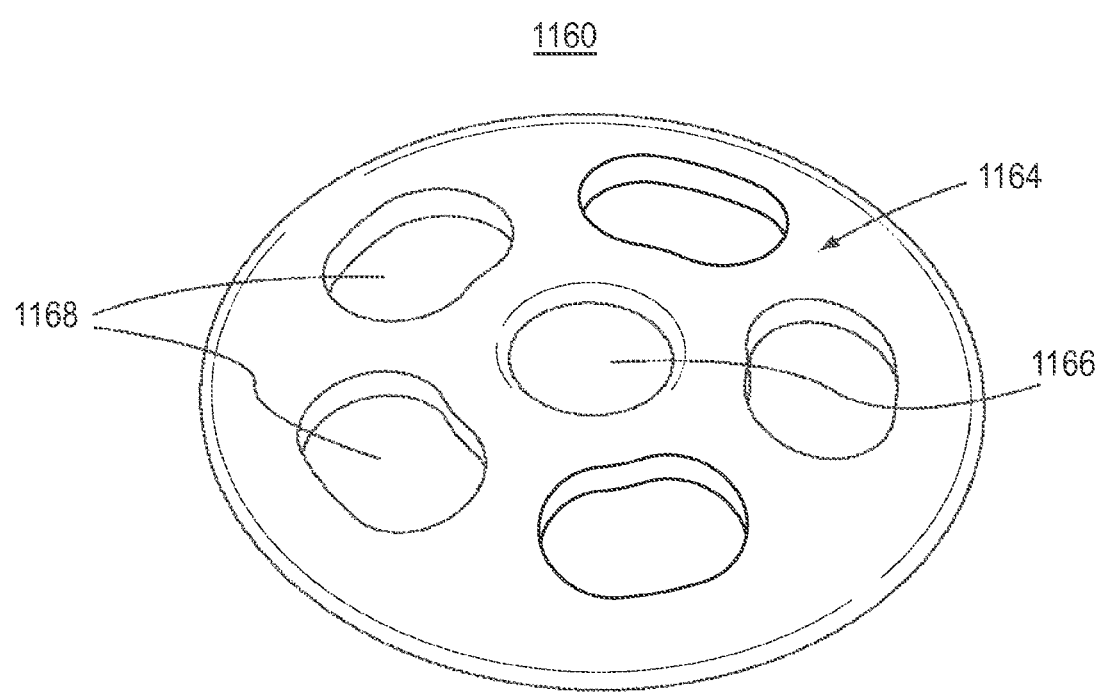
FIG. 71 is a rear perspective view of the implant of FIG. 70.
Figure 72:
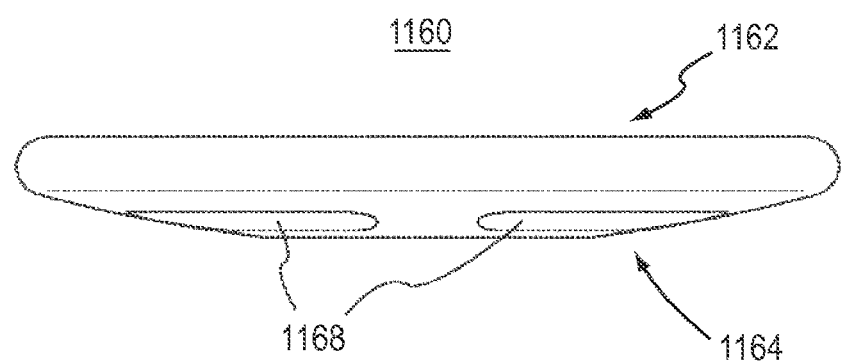
FIG. 72 is a side view of the implant of FIG. 70.
Figure 73:
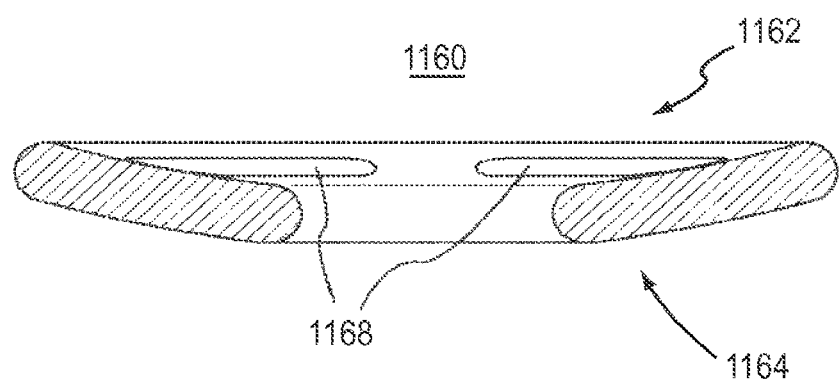
FIG. 73 is a cross-sectional side view of the implant of FIG. 70.

FIGS. 70-73 depict an implant 1160 according to an embodiment. Specifically, FIG. 70 is a front perspective view of implant 1160, FIG. 71 is a rear perspective view of implant 1160, FIG. 72 is a side view of implant 1160, and FIG. 73 is a cross-sectional side view of implant 1160. Implant 1160 can be similar to, and have similar elements and uses as implant 160 and implant 260 described above. By way of example, a fastener interface 1166 of implant 1160 can be similar to fastener interface 166 of implant 160, and similar to fastener interface 266 of implant 260. Implant 1160 includes a concave first face 1162, a convex second face 1164, a centrally-disposed substantially-circular fastener interface 1166, and five rounded rectangular shaped substance interfaces 1168.

Figure 74:
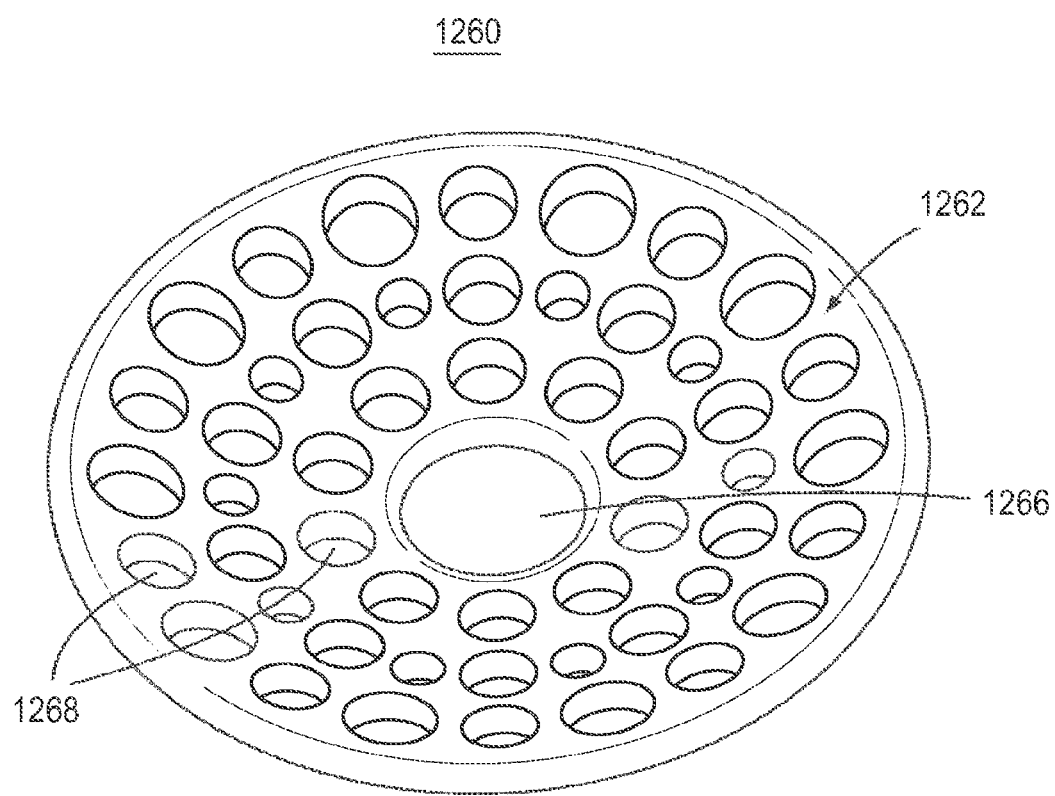
FIG. 74 is a front perspective view of implant according to an embodiment.
Figure 75:
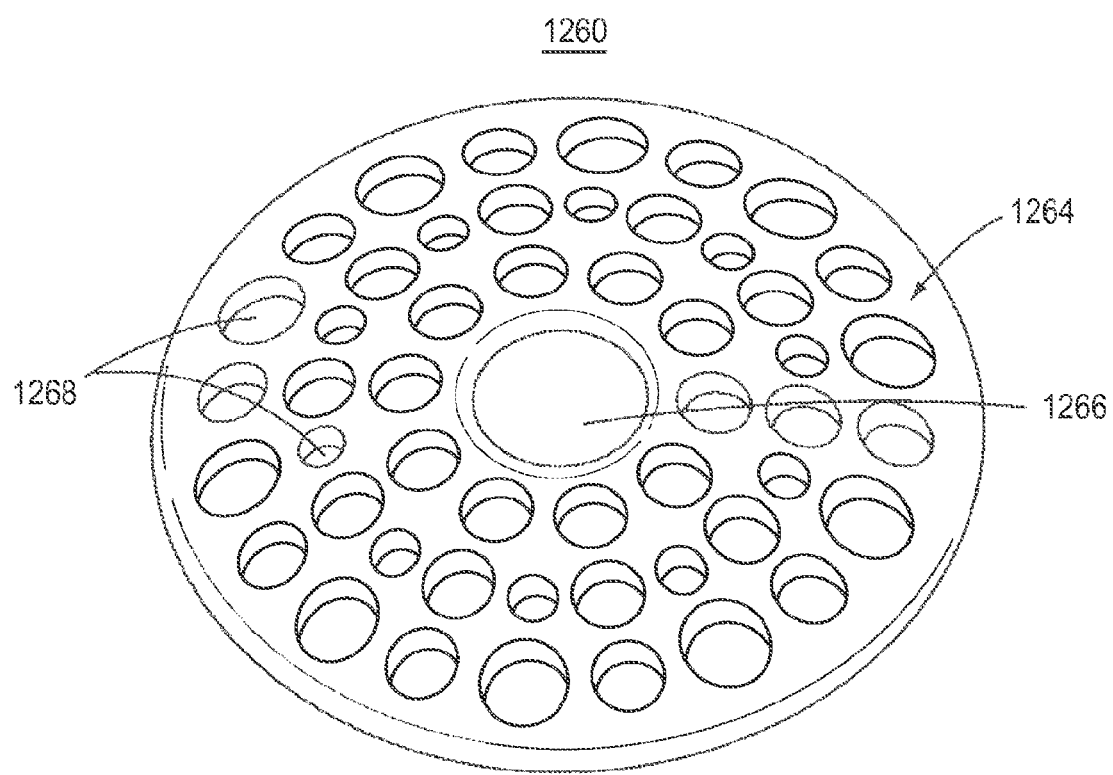
FIG. 75 is a rear perspective view of the implant of FIG. 74.
Figure 76:
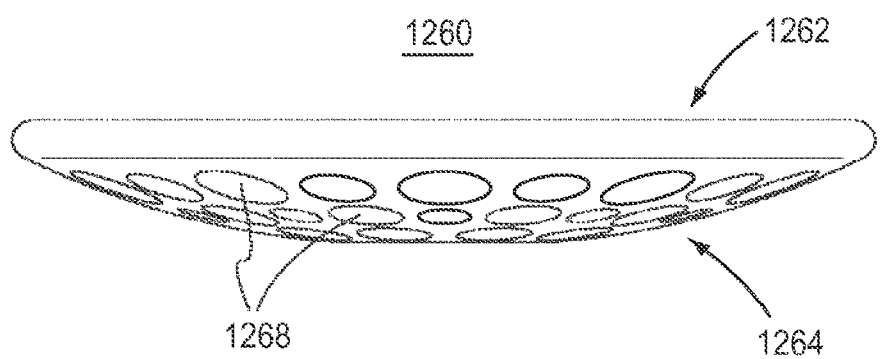
FIG. 76 is a side view of the implant of FIG. 74.
Figure 77:
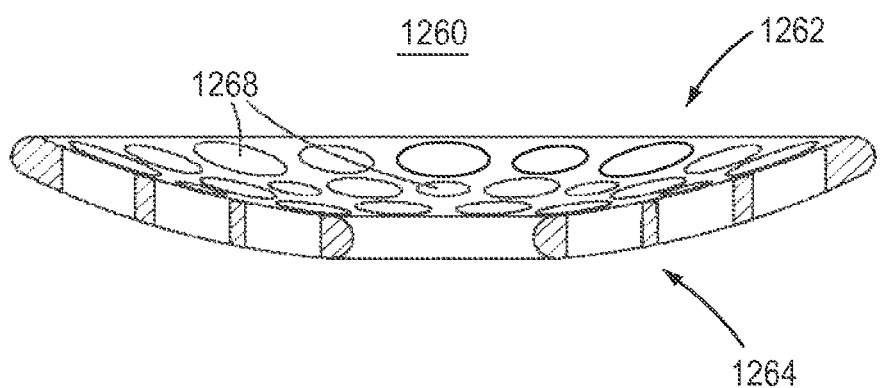
FIG. 77 is a cross-sectional side view of the implant of FIG. 74.

FIGS. 74-77 depict an implant 1260 according to an embodiment. Specifically, FIG. 74 is a front perspective view of implant 1260, FIG. 75 is a rear perspective view of implant 1260, FIG. 76 is a side view of implant 1260, and FIG. 77 is a cross-sectional side view of implant 1260. Implant 1260 can be similar to, and have similar elements and uses as implant 160 and implant 260 described above. By way of example, a fastener interface 1266 of implant 1260 can be similar to fastener interface 166 of implant 160, and similar to fastener interface 266 of implant 260. Implant 1260 includes a concave first face 1262, a convex second face 1264, a centrally-disposed substantially-circular fastener interface 1266, and several substantially-circular shaped and variably-sized substance interfaces 1268.

Figure 78:
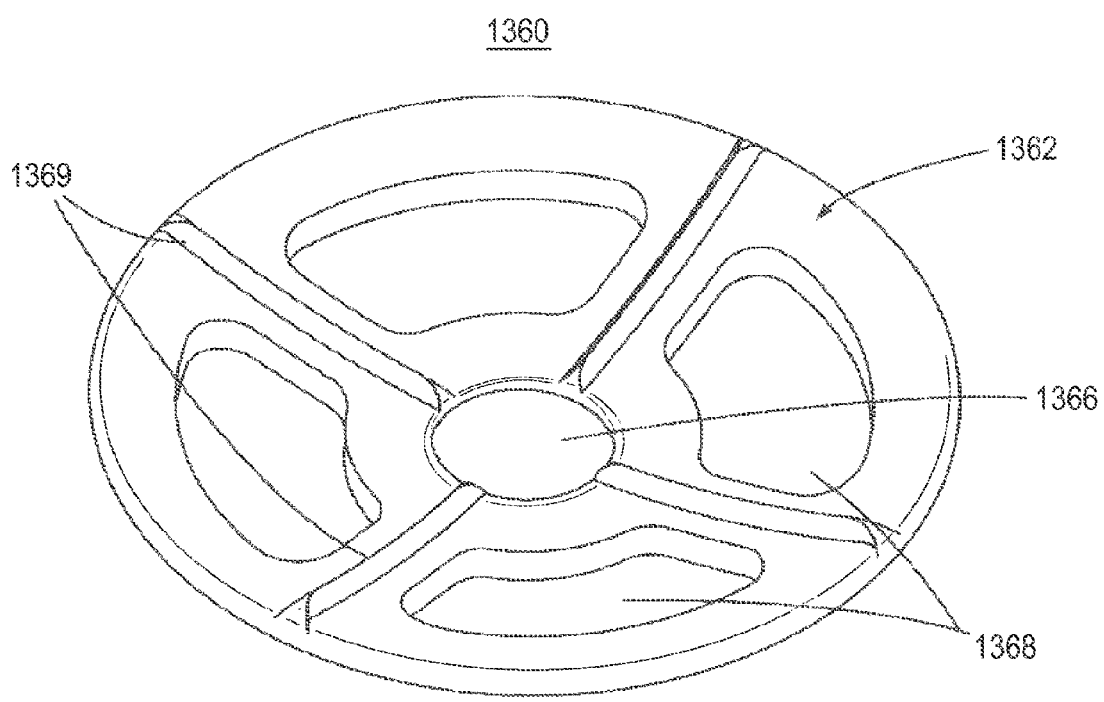
FIG. 78 is a front perspective view of implant according to an embodiment.
Figure 79:
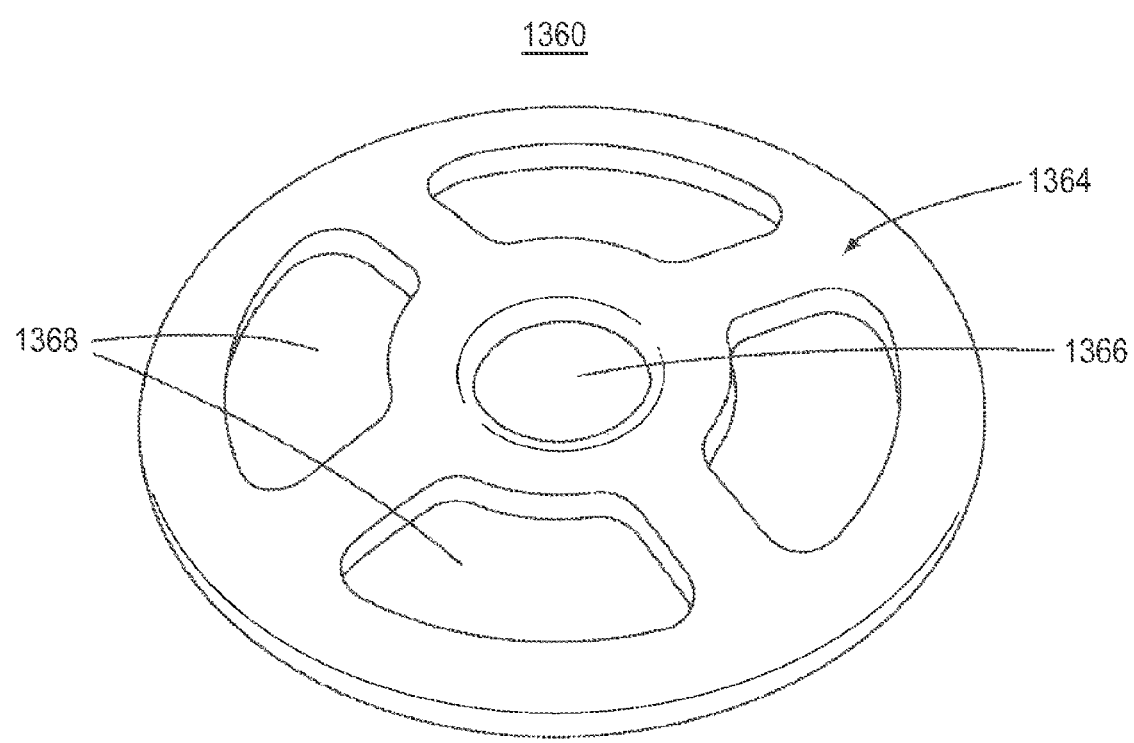
FIG. 79 is a rear perspective view of the implant of FIG. 78.
Figure 80:
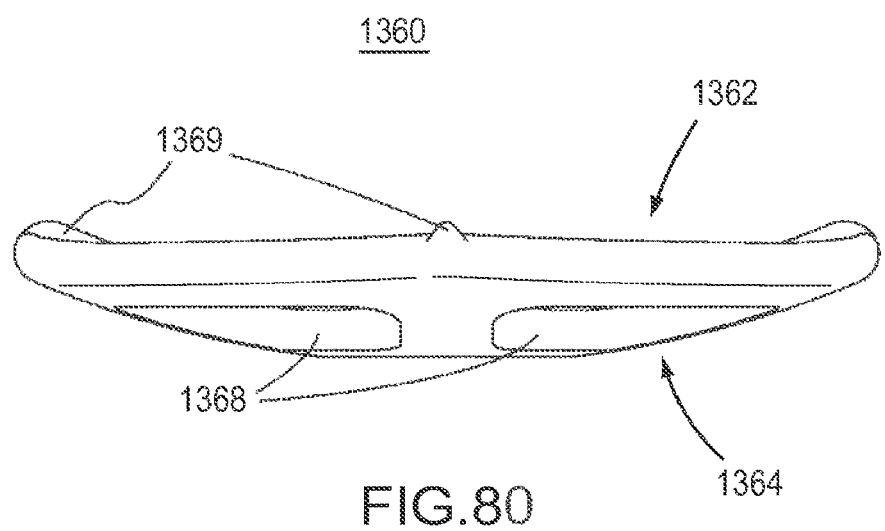
FIG. 80 is a side view of the implant of FIG. 78.
Figure 81:
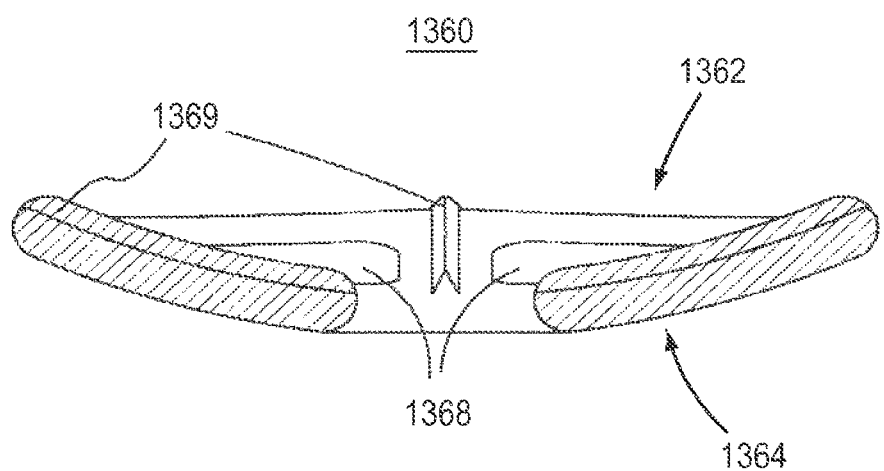
FIG. 81 is a cross-sectional side view of the implant of FIG. 78.

FIGS. 78-81 depict an implant 1360 according to an embodiment. Specifically, FIG. 78 is a front perspective view of implant 1360, FIG. 79 is a rear perspective view of implant 1360, FIG. 80 is a side view of implant 1360, and FIG. 81 is a cross-sectional side view of implant 1360. Implant 1360 can be similar to, and have similar elements and uses as implant 160 and implant 260 described above. By way of example, a fastener interface 1366 of implant 1360 can be similar to fastener interface 166 of implant 160, and similar to fastener interface 266 of implant 260. Implant 1360 includes a concave first face 1362, a convex second face 1364, a centrally-disposed substantially-circular fastener interface 1166, four irregular shaped substance interfaces 1368, and four projections 1369. Each of the four projections 1369 can engage, or other wise dig, latch, lock, or hook into or onto, a bone portion to prevent or reduce movement of the implant 1360, such as, for example, rotation of implant 1360, longitudinal movement of implant 1360, and/or lateral movement of implant 1360. In this manner, the projections 1369 can secure implant 1360 to a bone portion during a fusion procedure. In some embodiments, projections 1369 can substantially maintain a position of implant 1369 after a fastener member is removed.

While various embodiments have been described above, it should be understood that they have been presented by way of example only, not limitation, and various changes in form and details may be made. For example, while the descriptions given are with reference to stabilizing vertebra, another bone(s), such as, for example, a sternum and/or a rib(s) could be stabilized using the fastener members and implants described herein. In another example, a fastener member can be used to stabilize and/or fixate an intramedullary (IM) rod or nail. For example, the fastener member can be used at different longitudinal locations along an IM rod or nail, and used to couple adjacent bone portions to the IM rod or nail. In such situations, a given fastener member can fix a first bone portion, the IM rod or nail, and a second bone portion, all of which are positioned between the distal portion and the proximal portion of the fastener member. In yet another example, a fastener member can be used to stabilize and/or fixate a bone fragment. While various embodiments have been described above with regard to natural bone spaces, (e.g., the space between an inferior articulate process and a superior articulate process), in other embodiments, the bone spacing can be man-made (e.g., sternum split during a heart procedure), and/or due to an injury (e.g., broken bone).

Where methods described above indicate certain events occurring in certain order, the ordering of certain events can be modified. Additionally, certain of the events can be performed concurrently in a parallel process when possible, as well as performed sequentially as described above. Any portion of the apparatus and/or methods described herein may be combined in any combination, except mutually exclusive combinations. The embodiments described herein can include various combinations and/or sub-combinations of the functions, components and/or features of the different embodiments described. For example, FIGS. 54 and 56 depict band 580 including a single ratchet 592, and FIG. 57 depicts band 680 including a single ratchet 692, however, in some embodiments, any of the fastener members can include any number of ratchets. Similarly, any of fastener members can include a reinforcement piece and/or a implant. Furthermore, while one embodiment of an implant may be shown in use with one embodiment of a fastener member, in other embodiments, implants and fastener member can be used with other implants and fastener members. For example, while FIG. 28 depicts an implant being secured with a threaded wire, in some embodiments, a flexible fastening band can be used.

Facet Reinforcement Device

Although the flexible fastening band may be used alone or with an embodiment of facet implant as described above, in some applications it may be desirable to reinforce the fixation of the band as it exits the bone of the articular process. This may prevent cut out by relieving pressure on the surface of the articular process and hold in the bone from the fastener band and/or fastening mechanism. The facet reinforcement may also anchor the flexible facet band to the vertebra using a fastener. This may prevent migration of the band and restrict motion at the facet joint to improve fusion.

Figure 82:
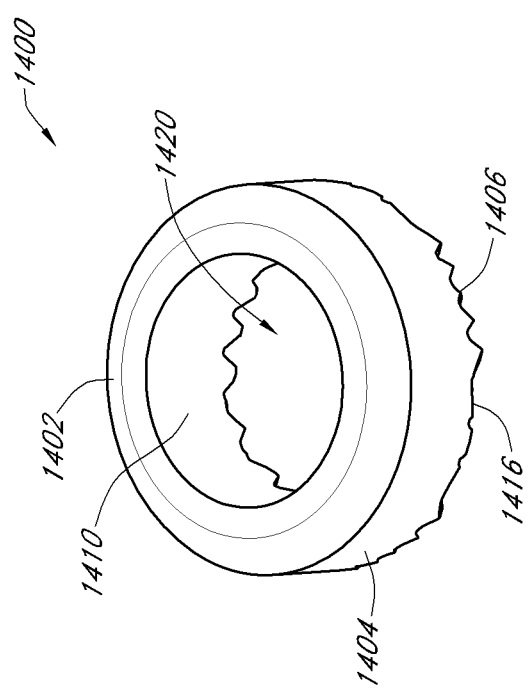
FIG. 82 is a front perspective view of a facet reinforcement device according to an embodiment.

FIG. 82 depicts one arrangement of facet reinforcement device 1400. The facet reinforcement device 1400 of the illustrated arrangement can include a proximal surface 1402, a distal surface 1406, an ablumenal surface 1404 extending from the proximal surface 1402 to the distal surface 1406. In certain arrangements, the proximal surface 1402 and/or distal surface 1406 can be curved and/or malleable to conform to the shape of the facet. The facet reinforcement device 1400 can include a luminal surface 1410 surrounding a central lumen 1420. The luminal surface 1410 can extend from the proximal surface 1402 to the distal surface 1406. The central lumen 1420 can be centrally disposed within the device 1400. As described below, the luminal surface 1410 can include a fastener interface (not illustrated) in certain embodiments.

As will be explained below, the facet reinforcement devices described herein can be used in combination with the implants depicted in FIGS. 8A-81A and/or other implants described herein. The facet reinforcement device 1400 can also be used in combination with the fastener members depicted in FIGS. 20-65, and/or other fastener members described herein. Accordingly, the fastener member 1480 depicted in FIG. 84 can refer to any fastener member described herein; and the fastener member 1580 depicted in FIG. 87 can refer to any fastener member described herein; and the fastener members 1680, 1680A depicted in FIG. 89 can refer to any fastener member described herein.

As shown in FIG. 82, at least a portion of one surface of the facet reinforcement device 1400 can include a roughened surface. A roughened surface may be advantageous when in contact with a bone or tissue surface because it may prevent slippage or migration of the facet reinforcement device 1400 against the bone. A roughened surface may aid in maintaining the facet reinforcement device 1400 and the fastener member 1480 (see Fig. 84) engaged with tissue or bone.

The roughened surface can include at least one projection 1416. As shown in FIG. 82, the facet reinforcement device 1400 can comprise a plurality of projections 1416. The projections 1416 can extend from the distal surface 1406 and can include a sharp edge or tip. The projections 1416 can also extend between the ablumenal surface 1404 and the luminal surface 1410 or in certain embodiments only extend along a portion of said area. In some embodiments, the projections 1416 comprise at least one spike, barb, wedge, or hook projecting from at least a portion of one surface of the facet reinforcement device 1400. In some embodiments, the projections 1416 can be ribbed, barbed, or threaded to resist separation after insertion into bone or tissue. The projections 1416 may have different shapes from one another or they may have a uniform shape. A portion of the surface of the projections 1416 can be porous. A porous surface can be created in any of a variety of ways known in the art, such as by applying sintered beads or spraying plasma onto the surface of the projection 1416. A porous surface can allow bone to grow into or attach to the surface of the projection 1416, thus securing the projection 1416 and the facet reinforcement device 1400 to the bone. In certain embodiments, other surfaces of the facet reinforcement device 1400 can be porous. In one embodiment, an adhesive or sealant, such as a cyanoacrylate, polymethylmethacrylate, or other adhesive known in the art, is used to bond at least one surface of the facet reinforcement device 1400 to a bone or tissue surface. In some embodiments, an adhesive or sealant is used to bond the distal surface 1406 of the facet reinforcement device 1400 to the surface of the facet.

The facet reinforcement device 1400 may include one row of projections 1416 or may include multiple rows of projections 1416. The facet reinforcement device 1400 may include projections 1416 arranged in a random order or orientation.

The ablumenal surface 1404 of the facet reinforcement device 1400 can include a substantially circular cross-section (cylindrical), as shown in FIG. 82. The ablumenal surface 1404 can have other cross-sectional shapes including, but not limited to, circular (cylindrical), hexagonal, rectangular (cuboid), square, elliptical, and/or have a combination of curved, flat surfaces and/or partial shapes. In certain embodiments, the ablumenal surface 1404 may conform to the shape of an insertion tool.

In the illustrated embodiment of FIG. 82, the central lumen 1420 and the luminal surface 1410 can be circular (cylindrical). The central lumen 1420 and the luminal surface 1410 can have other cross-sectional shapes including, but not limited to, hexagonal, rectangular (cuboid), square, elliptical, and/or have a combination of curved, flat surfaces and/or partial shapes. The central lumen 1420 and the luminal surface 1410 may conform to the shape of an insertion tool. In certain embodiments, the central lumen 1420 and the luminal surface 1410 can be shaped based on a shape of the fastener member (not shown) (e.g., the central lumen and luminal surface can have a similar cross-sectional shape as the fastener member extending through the central lumen). In certain embodiments, the central lumen 1420 and the luminal surface 1410 can include a substantially smooth inner surface to allow the fastener member 1480 to easily pass through. In other embodiments, the central lumen 1420 and the luminal surface 1410 can include a threaded inner surface to allow the fastener member 1480 to thread into central lumen 1420.

The central lumen 1420 and the luminal surface 1410 may be configured to match the shape of a lumen formed in the articular process, during a method of use. The central lumen 1420 and the luminal surface 1410 may be smaller than a lumen formed in the articular process, during a method of use. In this configuration, the facet reinforcement device 1400 may reduce stress at the outer aspect of the lumen in the bone. The central lumen 1420 and the luminal surface 1410 may be larger than a lumen formed in the articular process, during a method of use. In this configuration, the facet reinforcement device 1400 may be in contact with a larger surface area of the facet, thereby distributing the forces of the fastener member.

The proximal surface 1402 may have a feature to mechanically interfit with an insertion tool, including grooves and/or protrusions configured to mate with a corresponding groove and/or protrusion of the insertion tool. The proximal surface 1402 may have a feature (e.g., a groove or recess) to mechanically interfit with a portion of the fastener member 1480 (shown in FIG. 84). The feature to mechanically interfit with a portion of the fastener member may increase stability of the system and resistance to migration of components of the system.

The diameter of the facet reinforcement device 1400 may be in the range of 2 mm-20 mm or in the range of 4 mm-15 mm. The diameter of the central lumen 1420 may be in the range of 0.5 mm-10 mm or range of 1-7 mm.

Figure 83:
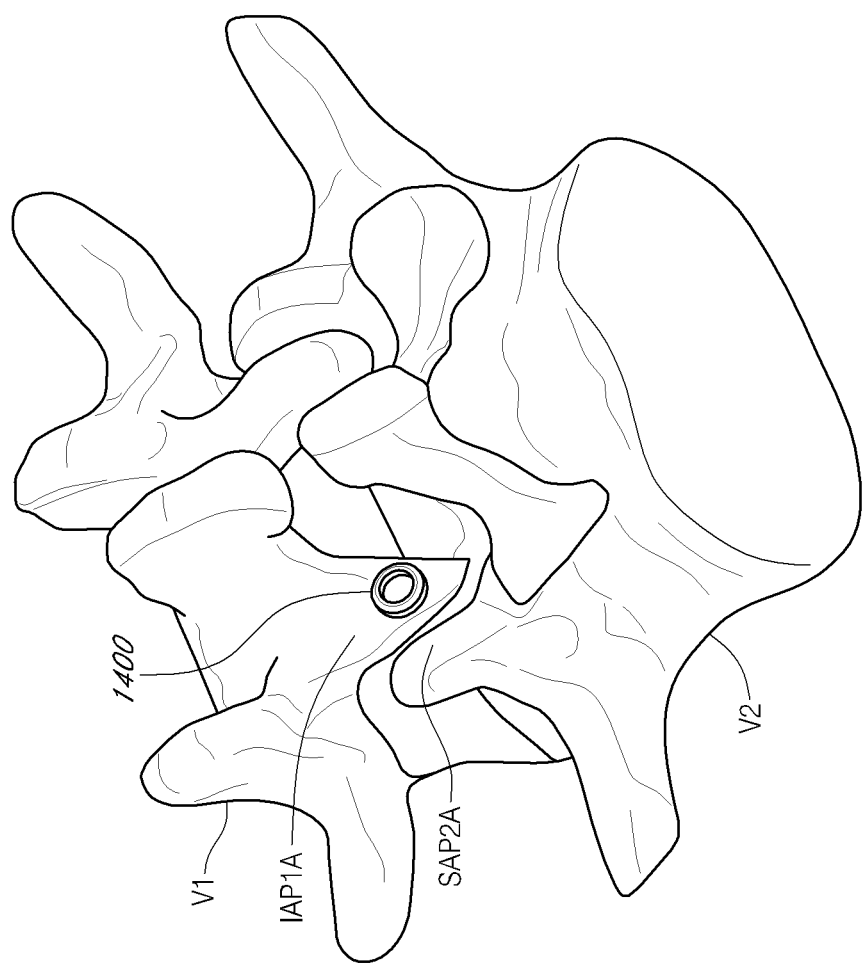
FIGS. 83-84 are posterior perspective views of a portion of the vertebral column depicting a method of stabilizing a vertebra using the facet reinforcement device of FIG. 82 and a fastener member according to an embodiment.
Figure 84:
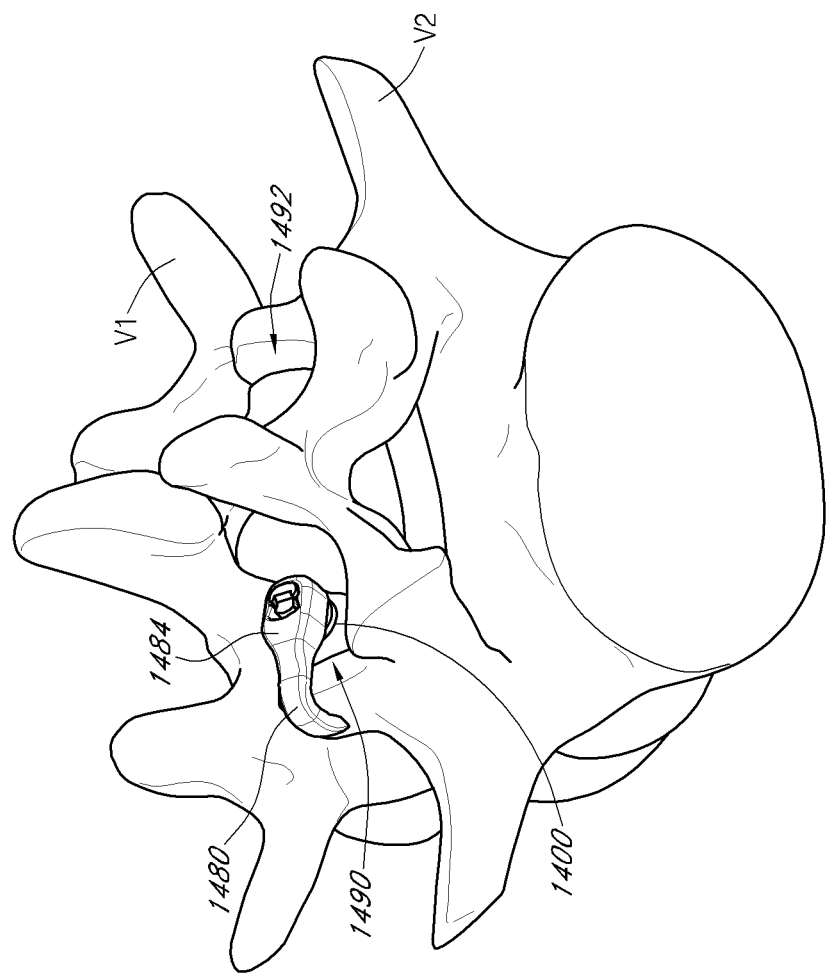

FIGS. 83-84 show posterior perspective views of a portion of the vertebral column during a method for fusing adjacent vertebrae using the embodiment of the facet reinforcement device 1400 shown in FIG. 82. The method can include using an implant deployed to restore the space between facets of a superior articular process of a first vertebra and an inferior articular process of an adjacent vertebra.

In one method of use, a drill or other device can be used to form a lumen in superior articular process SAP2A of vertebra V2 and inferior articular process IAP1A of vertebra V1. A portion of the surface of the facet of SAP2A and a portion of the surface of the facet of IAP1A can be prepared for fusion. For example, a portion of the surface of the facet can be ground, scored, roughened, sanded, etc., such that the surface of the facet can better adhere to any substances to aid in fusion and/or otherwise fuse more readily to an implant positioned within the facet joint.

FIG. 83 illustrates the facet reinforcement device 1400 placed on the outer, posterior facing surface of the left inferior articular process IAP1A of the superior vertebra V1. In other embodiments and/or in addition, the facet reinforcement device can be placed on the surface of the facet of SAP2A. A lumen is formed in the articular process. The facet reinforcement device 1400 can be placed after a lumen is formed in the articular process. In another arrangement, the facet reinforcement device 1400 can be placed prior to forming a lumen in the articular process. In this method, the facet reinforcement device 1400 may serve as a guide for drilling the lumen. The facet reinforcement device 1400 can be placed after or prior preparation for fusion. An insertion tool may remain on the facet reinforcement device 1400 during the steps of forming the lumen and/or during the step of preparing for fusion.

As shown in FIG. 84, a facet reinforcement device 1400 and a fastener member 1480 can be used to fuse a vertebra V1 and vertebra V2 via the inferior articular process IAP of vertebra V1 and the superior articular process SAP2A of vertebra V2. In some embodiments, at least one implant (not shown in FIG. 84) is used with the fastener member 1480 to fuse a vertebra V1 and vertebra V2. FIG. 84 depicts fusing the inferior articular process IAP of vertebra V1 and the superior articular process SAP2A of vertebra V2. However, the inferior articular process IAP1B of vertebra V1 can be fused to the superior articular process SAP2B of vertebra V2.

In one method of use, the fastener member 1480 can be positioned within a cannula and can be advanced through the cannula. The proximal end portion of fastener member 1480 can then be inserted into the central lumen 1420 of the facet reinforcement device 1400. The proximal end portion of the fastener member 1480 can be adjacent and/or abut the luminal surface 1410. The proximal end portion of fastener member 1480 can then be inserted into the lumen of inferior articular process IAP of vertebra V1. The proximal end portion of fastener member 1480 can be advanced until a proximal end portion of fastener member is positioned near the lumen of superior articular process SAP2A of vertebra V2. In some embodiments, the proximal end of the cannula can have a bend to direct the proximal end portion of fastener member 1480 into the lumen of superior articular process SAP2A of vertebra V2. The proximal end portion of fastener member 1480 can be inserted into the lumen of superior articular process SAP2A of vertebra V2. An implant can be inserted between the superior articular process SAP2A of vertebra V2 and inferior articular process IAP1A of vertebra V1. In some embodiments, the implant can be disposed prior to inserting the proximal end portion of the fastener member 1480 into the lumen of superior articular process SAP2A of vertebra V2. The cannula can be removed and/or reinserted at various points during the method, including, for example, after the proximal end portion of fastener member 1480 is inserted into the lumen formed within the superior articular process SAP2A of vertebra V2, after vertebra V1 and/or vertebra V2 have been stabilized, or at any other point during the method.

The fastener member 1480 can be secured. Securing the fastener member 1480 can be based on the type of fastener member used. By way of example, securing a fastener member 1480 having the characteristics of the fastener member depicted in FIGS. 49-51, can include the following steps: inserting the proximal end portion of the fastener member 1480 into a fastening mechanism 1484; the fastener mechanism located at a distal end portion of the fastener member 1480; securing an end of the fastener member 1480 to the opposite end of the fastener member 1480; securing the proximal end portion of the fastener member 1480 to the distal end portion of the fastener member 1480; and/or advancing the proximal end portion of the fastener member 1480 through the fastening mechanism 1484. In other embodiments, fastener member 1480 can be secured by tying a first portion the fastener member to a second portion of the fastener member, by forming a knot in a first end and second end; by screwing the fastener member into a threaded central lumen, by threading a fastener onto a threaded end of a fastener member disposed through a threaded central lumen, by including enlarged portion at the end of the fastener member, and/or combinations of above. The fastener member 1480 can be secured in order to retain the facet reinforcement device 1400. The facet reinforcement device 1400 is retained within a loop or other defined segment of the fastener member 1480. The reinforcement device 1400 can remain freely movable along a portion of the defined segment after the fastener member 1480 is secured. In some embodiments, the reinforcement device 1400 is immobile or otherwise secured along a portion of the defined segment after the fastener member 1480 is secured.

FIG. 84 illustrates the assembled system, including the facet reinforcement device 1400 and the fastener member 1480. The assembled system is implanted on the left facet joint 1490 between the superior vertebra V1 and the inferior vertebra V2. The left facet joint 1490 may be compressed by the assembled system, thereby bringing the two facet surfaces in close apposition. This compression is in contrast with the unsecured right facet joint 1492.

A second facet reinforcement device 1400, a second fastener member 1480 with or without a second implant may be implanted in the right facet joint 1492, according to the method described above with respect to the left facet joint 1490. The implantation of a second facet reinforcement device 1400 and a second fastener may improve stabilization. A second facet reinforcement device 1400 and a second fastener member 1480 with or without a second implant may be implanted on other levels of the spine. A plurality of reinforcement devices 1400 and a plurality of fastener members 1480 with or without a plurality of implants may be implanted on other levels of the spine, and at various locations on the spine. In some embodiments, the same and/or similar method of fixation, the same fastener members 1480, the same implants and/or the same facet reinforcement devices 1400 may be used at different locations. In other embodiments, a different method of fixation, different fastener members 1480, different implants and/or different facet reinforcement devices 1400 may be used at different locations.

Figure 85:
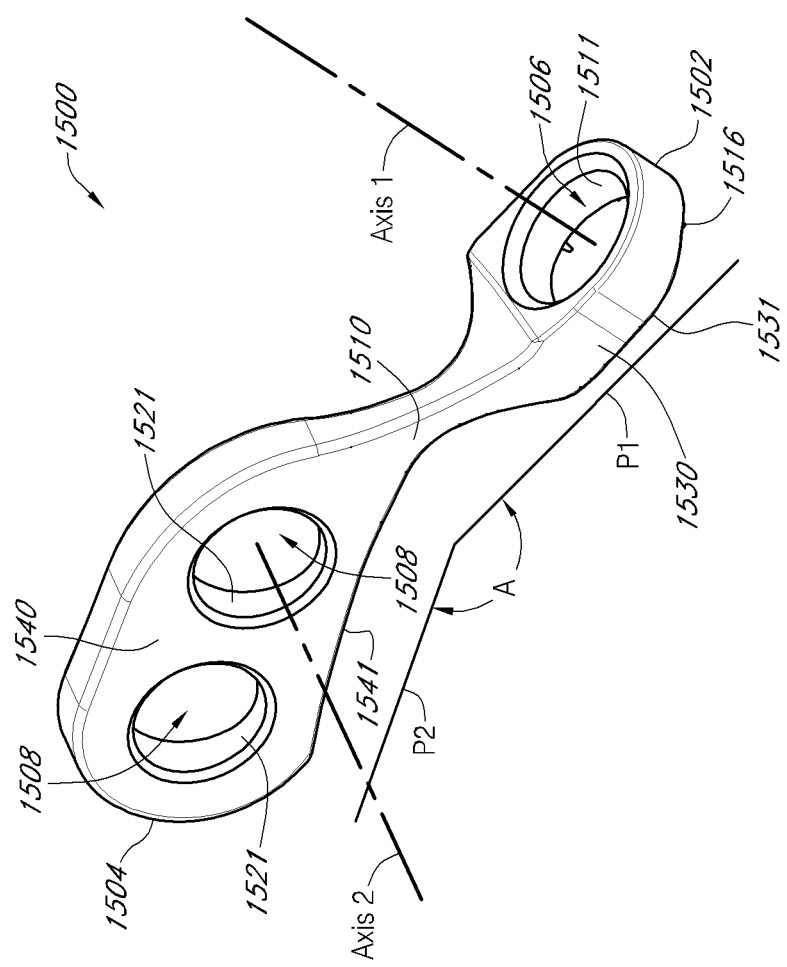
FIG. 85 is a front perspective view of a facet reinforcement device according to an embodiment.

FIG. 85 shows another embodiment of a facet reinforcement device 1500. In the illustrated arrangement, the facet reinforcement device 1500 has an inferior end 1502 and a superior end 1504. The facet reinforcement device 1500 has a first securing portion 1530 toward the inferior end 1502 and a second securing portion 1540 toward the superior end 1504. The first securing portion 1530 and second securing portion 1540 can be connected to each other by a central portion 1510.

The first securing portion 1530 can be configured for placement on an outer facet surface of a facet. The first securing portion 1530 can include a lumen 1506 surrounded by a luminal surface 1511. The lumen 1506 and the luminal surface 1511 can be substantially circular (cylindrical) as shown in the illustrated embodiment. The lumen 1506 can have other cross-sectional shapes including, but not limited to, circular (cylindrical), hexagonal, rectangular (cuboid), square, elliptical, and/or have a combination of curved, flat surfaces and/or partial shapes. The lumen 1506 and the luminal surface 1511 can be shaped based on a shape of a fastener member 1580 (e.g., having a shape complimentary or similar to the outer shape of the portion of the fastener member 1580 extending there-through). The lumen 1506 and the luminal surface 1511 may conform to the shape of an insertion tool. The lumen 1506 and the luminal surface 1511 can include a substantially smooth inner surface to allow the fastener member 1580 to easily pass through. In other embodiments, the lumen 1506 and the luminal surface 1511 can include a threaded surface to allow the fastener member to thread into the lumen 1506.

The first securing portion 1530 can include one (as illustrated), two, three or a plurality of lumens 1506. The one or more lumens 1506 can have the same shape or different shape. The first securing portion 1530 may include one row of lumen 1506, for example, the lumens 1506 can be aligned along an axis. In other arrangements, the first securing portion 1530 may include multiple rows of lumens 1506. The first securing portion 1530 may include lumens 1506 arranged in a random order or orientation. As will be described below, the one or more lumens 1506 can be configured to accept one or more fastener members 1580 and/or one or more fasteners 1590.

The second securing portion 1540 can be configured for placement on a vertebral structure. The vertebral structure can be remote or distanced from the outer facet surface of a facet. For example, in one arrangement, the second securing portion 1540 can be configured for placement on an outer surface or base of the spinous process 1570; a translaminar position, and/or for placement on an outer surface of the lamina (e.g., base of spinous process).

The second securing portion 1540 can include a lumen 1508 surrounded by a luminal surface 1521. The lumen 1508 and the luminal surface 1521 can be circular (cylindrical). The lumen 1508 can have other cross-sectional shapes including, but not limited to, hexagonal, rectangular (cuboid), square, elliptical, and/or have a combination of curved, flat surfaces and/or partial shapes. The lumen 1508 can be shaped based on a shape of the fastener member 1580 and/or the fastener 1590. The lumen 1508 and the luminal surface 1521 may be circular, hexagonal, rectangular (cuboid), square, elliptical, and/or have a combination of curved, flat surfaces and/or partial shapes. The lumen 1508 and the luminal surface 1521 may conform to the shape of an insertion tool. The lumen 1508 and the luminal surface 1521 can include a substantially smooth surface to allow the fastener member 1580 and/or the fastener 1590 to easily pass through, or the lumen 1508 can include a threaded surface to allow the fastener member 1580 and/or the fastener 1590 to thread into the lumen 1508.

The second securing portion 1540 can include one, two (as illustrated), three or a plurality of lumens 1508. Additional lumens 1508 may increase fixation security and reduce torsional forces.

The one or more lumens 1508 can have the same shape or different shape. The two lumens 1508 depicted in FIG. 85 have substantially the same shape. The second securing portion 1540 may include one row of lumens 1508, for example, the lumens 1508 can be aligned along an axis. The row of lumens 1508 may be aligned along a longitudinal axis of the second securing portion 1540. The second securing portion 1540 may include multiple rows of lumens 1508. The second securing portion 1540 may include lumens 1508 arranged in a random order or orientation. The one or more lumens 1508 can be configured to accept one or more fastener members 1580 and/or one or more fasteners 1590. The one or more lumens 1508 can be oriented in order to facilitate placement of the fastener members 1580 and/or the fasteners 1590. The fastener 1590 may be placed in a translaminar position. The fastener 1590 may be placed in the spinous process, or the base of the spinous process. The fastener 1590 may be placed across the spinous process of a vertebra.

At least one surface of the facet reinforcement device 1500 may have a feature to mechanically interfit with an insertion tool (not shown), including grooves and/or protrusions configured to mate with a corresponding groove and/or protrusion of the insertion tool. At least one surface of the facet reinforcement device 1500 can have a feature (e.g., a recess or groove) to mechanically interfit with the fastener member 1580 and/or fastener 1590. The feature to mechanically interfit with the fastener member 1580 and/or fastener 1590 member may increase stability of the system and resistance to migration of components of the system.

The diameter of the first securing portion 1530 may be in the range of 2 mm-20 mm or the diameter may be in the range of 4 mm-15 mm. The diameter of the lumen 1506 may be in the range of 0.5 mm-10 mm or in the range of 1-7 mm. The diameter of the lumen 1508 may be in the range of 0.5 mm-10 mm or 1-7 mm.

In some embodiments, at least a portion of one surface of the facet reinforcement device 1500 has a roughened surface and/or a porous surface, as described above with respect to FIG. 82. The roughened surface can comprise at least one projection 1516. In one embodiment, the projection 1516 can comprise at least one spike, barb, wedge, or hook projecting from one surface of the facet reinforcement device 1500. The first securing portion 1530, the second securing portion 1540, the central portion 1510, and/or any combination of these portions may include a roughened surface and/or a porous surface. In some embodiment, an adhesive or sealant, such as a cyanoacrylate, polymethylmethacrylate, or other adhesive known in the art, is used to bond one surface of the facet reinforcement device 1500 to a bone or tissue surface. In some embodiments, at least a portion of one surface of the facet reinforcement device 1500 may be curved or malleable. The portion of one surface of the facet reinforcement device 1500 may be shaped to conform to a shape of an anatomic structure, such as a facet or spinous process.

As shown the first securing portion 1530 and the second securing portion 1540 may lie on different planes as shown in FIG. 85. The first securing portion 1530 can lie on a plane P1, as shown in FIG. 85. The first securing portion 1530 can include the lumen 1506. The lumen 1506 has a central, longitudinal axis, Axis 1, extending through the lumen 1506. The plane P1 can lie perpendicular to the Axis 1 of the lumen 1506 of the first securing portion 1530. The plane P1 can lie adjacent to a distal surface 1531 of the first securing portion 1530. The plane P1 can lie adjacent to a surface of the first securing portion 1530 configured to engage a bone or tissue.

The second securing portion 1540 can lie on a plane P2. The second securing portion 1540 can include at least one lumen 1508. The lumen 1508 has a central, longitudinal axis, Axis 2, extending through the lumen 1508. The plane P2 can lie parallel to the Axis 2 of the lumen 1508 of the second securing portion 1540. The plane P2 can lie adjacent to a distal surface 1541 of the second securing portion 1540. The plane P2 can lie adjacent to a surface of the second securing portion 1540 configured to engage a bone or tissue.

The plane P1 may be angled relative to the plane P2 to form an angle A (see FIG. 85) between the plane P1 and the plane P2. The angle A may be between 30-150 degrees. The angle A may be 60-105 degrees in one arrangement. The Axis 1 and the Axis 2 may not be parallel in such arrangements. In one embodiment, the Axis 1 and the Axis 2 may be perpendicular. In other embodiments, the Axis 1 may be angled relative to the Axis 2.

In certain arrangements, the first securing portion 1530 may be offset in multiple dimensions from the second securing portion 1540. The first securing portion 1530 may be offset along a longitudinal axis of the facet replacement device 1500 from the second securing portion 1540. The longitudinal axis of the first securing portion 1530 may be offset, angled, or otherwise not aligned with the longitudinal axis of the second securing portion 1540.

Figure 86:
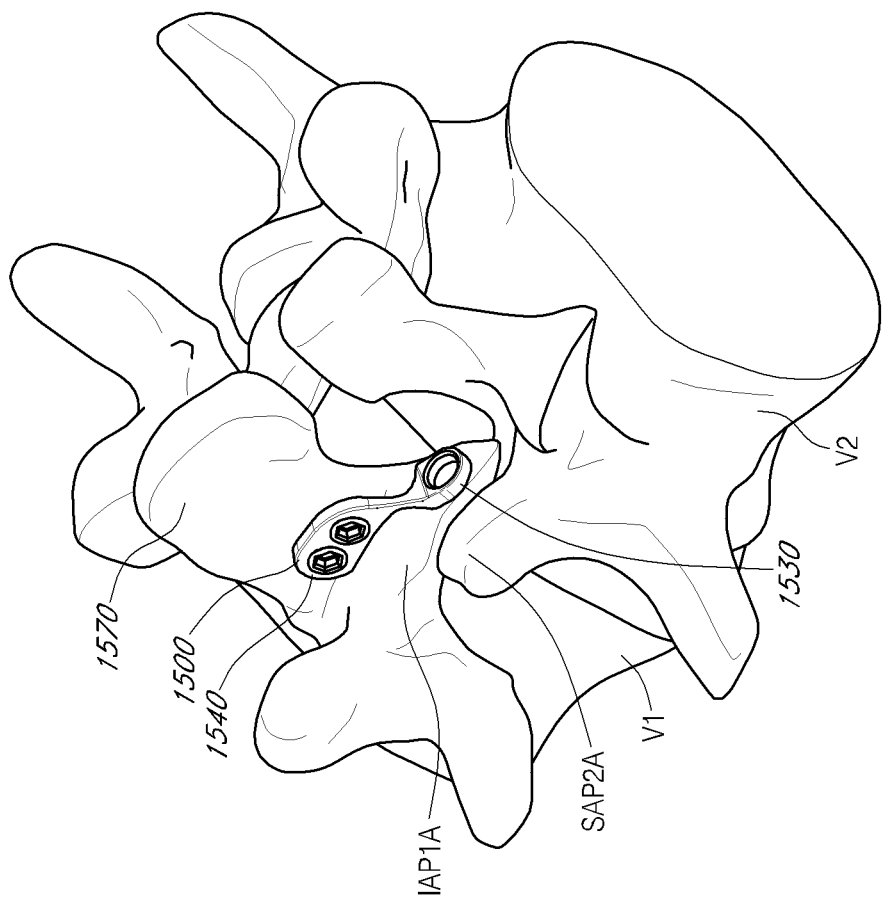
FIGS. 86-87 are posterior perspective views of a portion of the vertebral column depicting a method of stabilizing a vertebra using the facet reinforcement device of FIG. 85 and a fastener member according to an embodiment.

For example, as illustrated in FIG. 86, the second securing portion 1540 may lie medial and/or posterior to the first securing portion 1530. The second securing portion 1540 may lie superior to the first securing portion 1530. Proximal or posterior, as referred to here, refers to the part of the vertebra or the facet reinforcement device that is configured to be implanted in a vertebra toward the tip of the spinous process. Distal and anterior refer to the part of the vertebra or the facet reinforcement device that is configured to be implanted in a vertebra toward the vertebral body. Medial refers to toward the midline (center of spinous process), lateral refers to a direction away from the midline (toward the tip of the transverse processes). Superior refers to a direction toward the head, or to a part of the facet reinforcement device that configured to face toward the head on placement, and inferior to a structure or part of the facet reinforcement device which faces or is positioned toward the feet. The central portion 1510 may be bent and/or twisted to provide the offset and/or angulation of the first securing portion 1530 relative to the second securing portion 1540.

Figure 87:
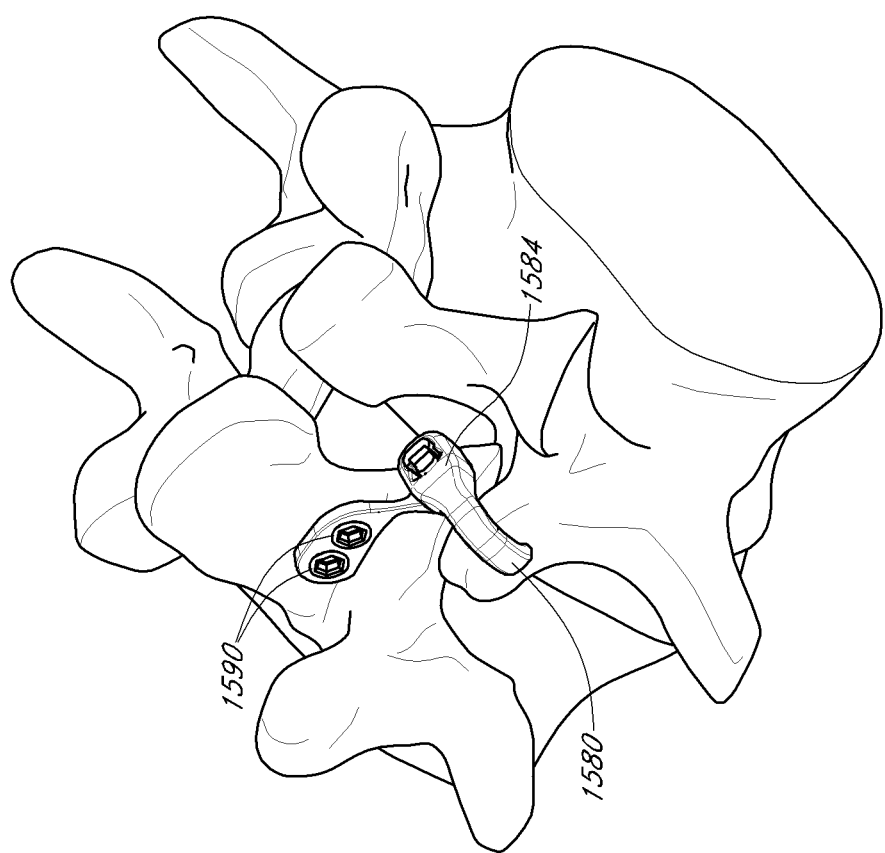

FIGS. 86-87 show perspective views of a portion of the vertebral column during a method for fusing adjacent vertebrae using the facet reinforcement device 1500. The method may include using an implant deployed to restore the space between facets of a superior articular process of a first vertebra and an inferior articular process of an adjacent vertebra.

In one method of use, a drill or other device can be used to form a lumen in superior articular process SAP2A of vertebra V2 and inferior articular process IAP1A of vertebra V1. A portion of the surface of the facet of SAP2A and a portion of the surface of the facet of IAP1A can be prepared for fusion. Specifically, a portion of the surface of the facet can be ground, scored, roughened, sanded, etc., such that the surface of the facet can better adhere to any substances to aid in fusion and/or otherwise fuse more readily to the implant if used.

FIG. 86 illustrates the facet reinforcement device 1500 placed on an outer surface of the superior vertebra V1. The first securing portion 1530 is placed on outer, posterior facing surface of the left inferior articular process IAP1A of the superior vertebra V1. The second securing portion 1540 is placed on outer surface of the spinous process, near the base of the spinous process of V1.

In one method of use, a lumen is formed in the articular process. The facet reinforcement device 1500 can be placed after a lumen is formed in the articular process. The facet reinforcement device 1500 can be placed prior to forming a lumen in the articular process. In this method, the facet reinforcement device 1500 may serve as a guide for drilling the lumen. The facet reinforcement device 1500 can be placed after preparation for fusion. The facet reinforcement device 1500 can be placed before preparation for fusion. An insertion tool may remain on the facet reinforcement device 1500 during the steps of forming the lumen and/or during the step of preparing for fusion.

As shown in FIG. 87, a facet reinforcement device 1500 and a fastener member 1580 can be used to fuse a vertebra V1 and vertebra V2 via the inferior articular process IAP of vertebra V1 and the superior articular process SAP2A of vertebra V2. In some embodiments, at least one implant is used with the fastener member 1580 to fuse a vertebra V1 and vertebra V2. FIG. 87 depicts fusing the inferior articular process IAP1A of vertebra V1 and the superior articular process SAP2A of vertebra V2. However, the inferior articular process IAP1B of vertebra V1 can be fused to the superior articular process SAP2B of vertebra V2.

The fastener member 1580 can be secured. Securing the fastener member 1580 can be based on the type of fastener member used. By way of example, securing a fastener member 1580 having the characteristics of the fastener member depicted in FIGS. 49-51, can include the following steps: inserting the proximal end portion of the fastener member 1580 into a fastening mechanism 1584; the fastener mechanism located at a distal end portion of the fastener member 1580; securing an end of the fastener member 1580 to the opposite end of the fastener member 1580; securing the proximal end portion of the fastener member 1580 to the distal end portion of the fastener member 1580; and/or advancing the proximal end portion of the fastener member 1580 through the fastening mechanism 1584. In other embodiments, fastener member 1580 can be secured by tying a first portion the fastener member to a second portion of the fastener member, by forming a knot in a first end and second end; by screwing the fastener member into a threaded central lumen, by threading a fastener onto a threaded end of a fastener member disposed through a threaded central lumen, by include at the end of the fastener member, and/or combinations of above. The fastener member 1580 can be secured in order to retain the facet reinforcement device 1500. The facet reinforcement device 1500 is retained within a loop or other defined segment of the fastener member 1580. The reinforcement device 1500 can remain freely movable along a portion of the defined segment after the fastener member 1580 is secured. In some embodiments, the reinforcement device 1500 is immobile or otherwise secured along a portion of the defined segment after the fastener member 1580 is secured. The fastener member 1580 can be secured in order to retain the first securing portion 1530.

A lumen is formed in the spinous process. The facet reinforcement device 1500 can be placed after a lumen is formed in the spinous process. The facet reinforcement device 1500 can be placed prior to forming a lumen in the spinous process. In this method, the facet reinforcement device 1500 may serve as a guide for drilling the lumen. The second securing portion 1540 can be secured to V1 using fastener member 1580 and/or other fastener 1590. The fastener 1590 may be a screw, a bolt, a dual headed screw, a pedicle screw, a transpedicular screw, a post, a plug, a tether, artificial ligament, a rod or any other device of securing a plate to bone, which would be known to one skilled in the art. The fasteners 1590 may pass translaminally or through the base of the spinous process 1570. In some embodiments, the fastener 1590 is threaded and the lumen 1508 is threaded. The corresponding threading between lumen 1508 and fastener 1590 may facilitate the securing and/or locking of the fastener 1590 to the facet reinforcement device 1500. FIG. 86 depicts two lumens 1508 in the second securing portion 1540. The fasteners 1590 associated with the lumens 1508 may be the same or different, or a combination of similar and different fasteners for three or more lumens 1508.

FIG. 87 illustrates the assembled system, including the facet reinforcement device 1500 and the fastener member 1580. The assembled system is implanted on the left facet joint between a superior vertebra V1 and an inferior vertebra V2. The left facet joint may be compressed by the assembled system, thereby bringing the two facet surfaces in close apposition. This compression is in contrasts with the unsecured right facet joint.

Figure 88:
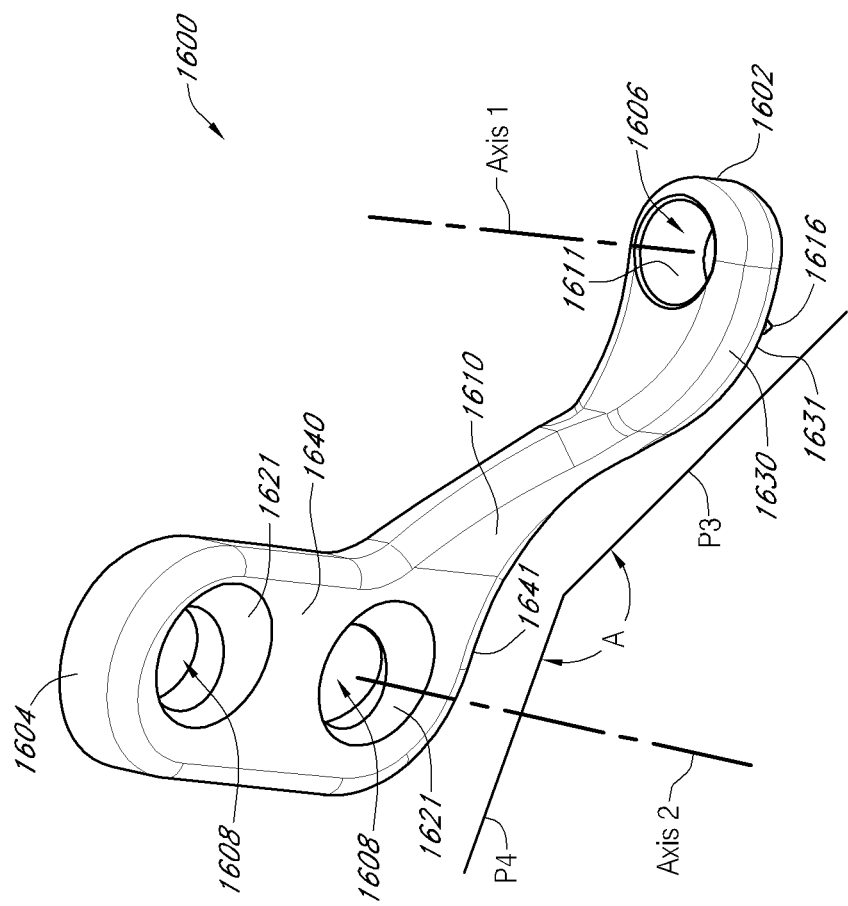
FIG. 88 is a front perspective view of a facet reinforcement device according to an embodiment.

FIG. 88 shows an embodiment of a facet reinforcement device 1600. The facet reinforcement device 1600 has similar features to the facet reinforcement device 1500, described herein. The facet reinforcement device 1600 includes a first securing portion 1630 toward an inferior end 1602 and a second securing portion 1640 toward a superior end 1604. A central portion 1610 connects the first securing portion 1630 and the second securing portion 1640. The first securing portion 1630 can include at least one lumen 1606 surrounded by a luminal surface 1611. The first securing portion 1630 can be configured for placement on an outer facet surface of a facet. In some embodiments, at least a portion of one surface of the facet reinforcement device 1600 has a roughened surface and/or a porous surface, which may include at least one projection 1616.

The second securing portion 1640 can be configured for placement on a vertebral structure. The vertebral structure can be remote from the outer facet surface of a facet. The second securing portion 1640 can be configured for placement on an outer surface of the spinous process 1670.

The second securing portion 1640 can include at least one lumen 1608 surrounded by a luminal surface 1621. The second securing portion 1640 can include two lumens 1608. The two lumens 1608 may be in a different configuration than lumens 1508, shown in FIG. 85. For example, the two lumens 1608 are oriented vertically along the spinous process in the second securing portion 1640. The two lumens 1508 are oriented horizontally along the base of the spinous process in the second securing portion 1540. The orientation of the two lumens 1608 of the facet reinforcement device 1600 is generally perpendicular to the lumens 1508 of the facet reinforcement device 1500. The orientation shown in FIG. 89 may be advantageous in countering forces on the facet reinforcement device 1600. The orientation shown in FIG. 89 may permit increased visualization of posterior vertebral structures such as the V1 lamina. The orientation of the lumens 1608 permits placement of fasteners 1690A across the spinous process 1670.

The first securing portion 1630 and the second securing portion 1640 may lie on different planes. The first securing portion 1630 lies on a plane P3, as shown in FIG. 88. The lumen 1606 has a central, longitudinal axis, Axis 1, extending through the lumen 1606. The plane P3 lies perpendicular to the Axis 1 of the lumen 1606 of the first securing portion 1630. The plane P3 can lie adjacent to a distal surface 1631 of the first securing portion 1630.

The second securing portion 1640 lies on a plane P4. The second securing portion 1640 can include at least one lumen 1608. The lumen 1608 has a central, longitudinal axis, Axis 2, extending through the lumen 1608. The plane P4 lies parallel to the Axis 2 of the lumen 1608 of the second securing portion 1640. The plane P4 can lie adjacent to a distal surface 1641 of the second securing portion 1640. The plane P3 may be angled relative to the plane P4. An angle A may be formed between the plane P3 and the plane P4. The angle A may be between 30-150 degrees. The angle A may be 60-105 degrees. The first securing portion 1630 may be offset in multiple dimensions from the second securing portion 1640.

Figure 89:
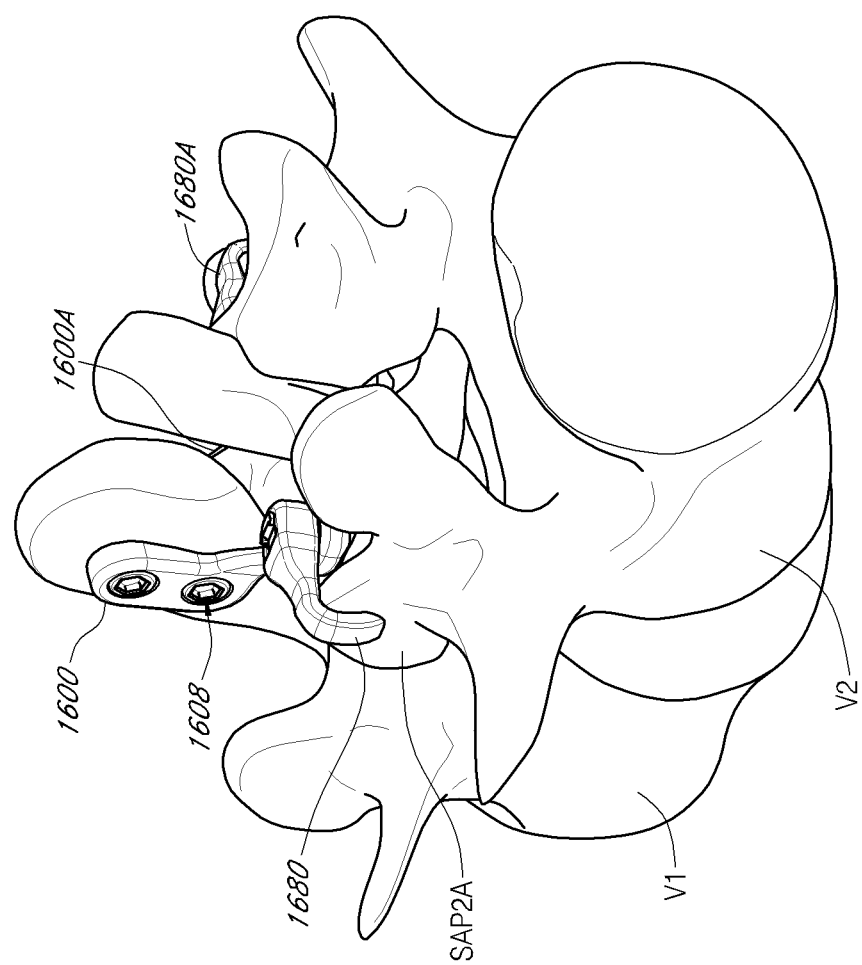
FIGS. 89-91 are perspective views of a portion of the vertebral column depicting a method of stabilizing a vertebra using a first facet reinforcement device of FIG. 88, a second facet reinforcement device, and one or more fastener members according to an embodiment.
Figure 90:
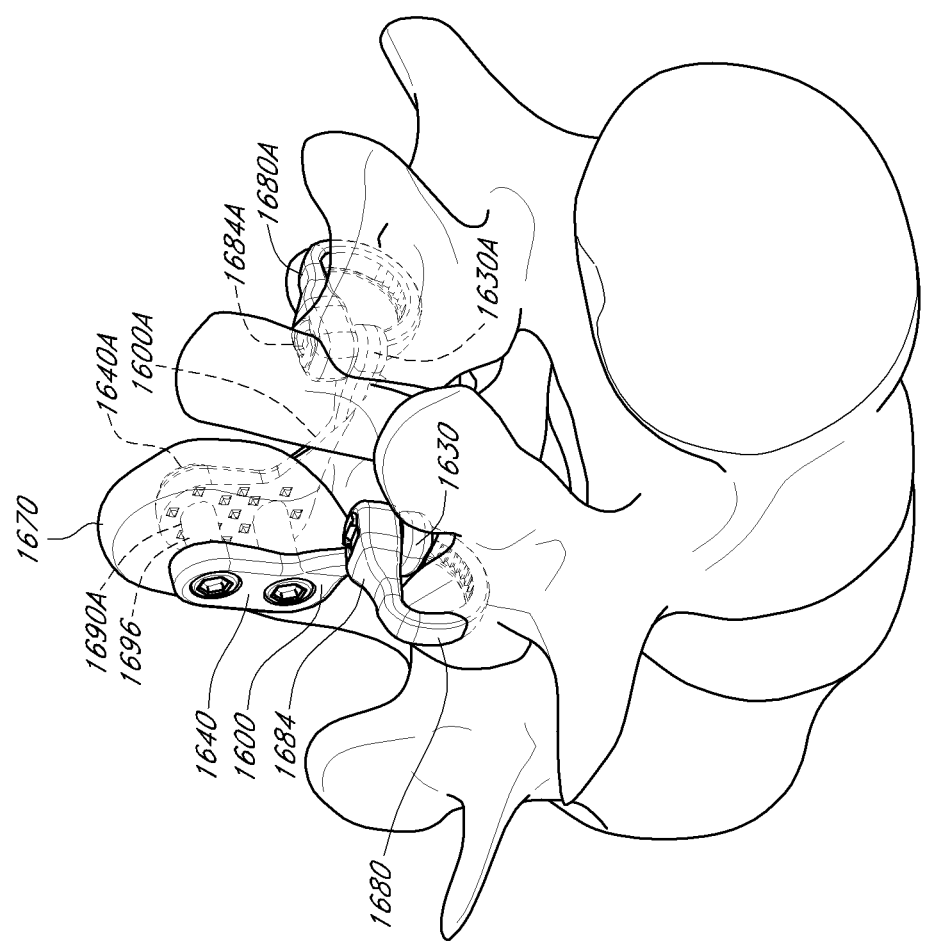
Figure 91:
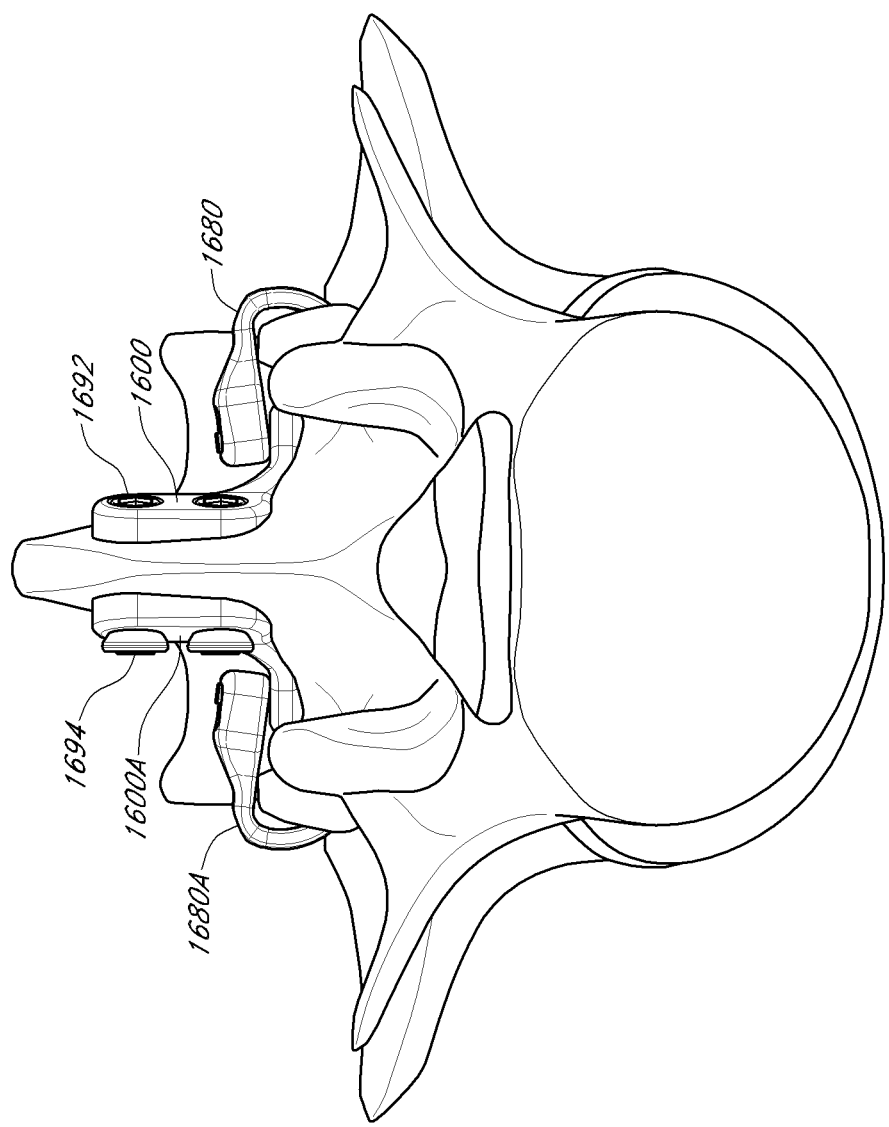

FIGS. 89-91 show perspective views of a portion of the vertebral column during a method for fusing adjacent vertebrae using a facet reinforcement device 1600 and a facet reinforcement device 1600A. The implantation of the facet reinforcement devices 1600, 1600A can be substantially similar to the implantation of the facet reinforcement device 1500.

FIG. 90 illustrates the facet reinforcement devices 1600 and 1600A placed on an outer surface of the superior vertebra V1. A first securing portion 1630 is placed on outer, posterior facing surface of the left inferior articular process IAP1A of the superior vertebra V1. A second securing portion 1640 is placed on outer surface of the spinous process 1670. A first securing portion 1630A is placed on outer, posterior facing surface of the right inferior articular process IAP1B of the superior vertebra V1. A second securing portion 1640A is placed on outer surface of the spinous process 1670.

The second securing portion 1640 can include two lumens 1608. The two lumens 1608 are oriented vertically along the spinous process in the second securing portion 1640. The second securing portion 1640A can include two lumens 1608A. The two lumens 1608A are oriented vertically along the spinous process in the second securing portion 1640A. The orientation of the lumens 1608, 1608A permits placement of fasteners 1690A across the spinous process 1670.

A lumen can be formed in superior articular process SAP2A of vertebra V2 and inferior articular process IAP of vertebra V1. A lumen can be formed in superior articular process SAP2B of vertebra V2 and inferior articular process IAP1B of vertebra V1. A fastener member 1680 and a fastener member 1680A can be inserted in a manner as described above. The proximal end portion of a fastener member 1680 can be inserted into the lumen 1606 of the first securing portion 1630, the lumen of inferior articular process IAP1A of vertebra V1, and the lumen of superior articular process SAP2A of vertebra V2. The proximal end portion of a fastener member 1680A can be inserted into a lumen in the first securing portion 1630A, the lumen of inferior articular process IAP1B of vertebra V1, and the lumen of superior articular process SAP2B of vertebra V2. An implant can be inserted between the superior articular process and the inferior articular process.

The fastener members 1680, 1680A can have the characteristics of the fastener member 1580 and can be secured in a similar manner to securing fastener member 1580. The proximal end portion of the fastener member 1680, 1680A can be inserted into a fastening mechanism 1684, 1684A. The fastener mechanism 1684, 1684A can be located at a distal end portion of the fastener member 1680, 1680A. As shown in FIG. 90, the facet reinforcement device 1600 and the fastener member 1680 can be used to fuse a vertebra V1 and vertebra V2 via the inferior articular process IAP of vertebra V1 and the superior articular process SAP2A of vertebra V2. The facet reinforcement device 1600A and a fastener member 1680A can be used to fuse a vertebra V1 and vertebra V2 via the inferior articular process IAP1B of vertebra V1 and the superior articular process SAP2B of vertebra V2. The facet reinforcement device 1600 can be substantially similar to the facet reinforcement device 1600A. The facet reinforcement device 1600 can be a mirror image of the facet reinforcement device 1600A.

A lumen is formed in the spinous process 1670. The second securing portions 1640, 1640A can be secured to V1 using the fastener members 1680, the fastener 1690, and/or the fastener 1690A. The fastener members 1680 and the fastener 1690 can be inserted in a manner as describe above with respect to fastener members 1580 and the fastener 1590. The fastener 1690 may be a screw, a bolt, a dual headed screw, a pedicle screw, a transpedicular screw, a post, a plug, a tether, artificial ligament, a rod or any other means of securing a plate to bone, which would be known to one skilled in the art. In some embodiments, the fastener 1690 is threaded and the lumen 1608 is threaded. The corresponding threading between the lumen 1608 and the fastener 1690 may facilitate the securing and/or locking of the fastener 1690 to the facet reinforcement device 1600. FIG. 89 depicts two lumens 1608 in the second securing portion 1640. The fasteners 1690 associated with the lumens 1608 may be the same or different, or a combination of similar and different fasteners for three or more lumens 1608.

The fastener 1690A may pass translaminally or through the spinous process 1670. The fastener 1690A is located between the lumen 1608 and the lumen 1608A. The fastener 1690A is located between the second securing portion 1640 and the second securing portion 1640A. Referring to FIGS. 90 and 91, the fastener 1690A is illustrated with head 1694, shaft 1696, and nut 1692. The shaft 1696 may be threaded or smooth. The fastener 1690A can take the form of a screw, a bolt, a dual headed screw, a pedicle screw, a transpedicular screw, a post, a plug, a tether, artificial ligament, a rod or any other form known in the art. Additional security may be provided by securing the two facet reinforcement devices 1600, 1600A together through the spinous process.

FIGS. 89-91 illustrate the assembled system, including the facet reinforcement device 1600 and 1600A. FIG. 91 illustrates the system, viewed from superior to V1. The fasteners 1690A may be seen passing through lumen 1608 in facet reinforcement device 1600, through spinous process 1670 and through lumen 1608A in facet reinforcement device 1600A in FIG. 90.

The assembled system is implanted on the left facet joint and the right facet joint between a superior vertebra V1 and an inferior vertebra V2. The facet joints may be compressed by the assembled system, thereby bringing the two facet surfaces in close apposition. The implantation of the second facet reinforcement device 1600A and the second fastener member 1680A may improve stabilization.

The facet reinforcement device 1400, 1500, 1600, 1600A and fasteners 1580, 1590, 1680, 1690, 1690A may be made of any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials. The facet reinforcement device 1400, 1500, 1600, 1600A may be made of multiple materials in combination. For example, the ablumenal surface 1404 can comprise a polymer, such as PEEK or polyethylene, and the luminal surface 1410 can comprise a metal or ceramic. For example, the proximal surface 1402 can comprise a polymer and the distal surface 1406 and/or the projections 1416 can comprise a metal or ceramic. The material of the facet reinforcement device 1400 can be the same as the material of the fastener member and/or the implant. The material of the facet reinforcement device 1400 can be different from the material of the fastener member and/or the implant.

Kits may be provided to facilitate spine fixation procedures. Kits may include one or more facet reinforcement devices, such as any of those described herein. Different sizes and configurations of facet reinforcement devices may be provided in a single kit. Different kits may be available that have different sizes and configurations of facet reinforcement devices. Kits may include one or more fastener members, such as any of those described herein. The kits may include one or more fasteners, such as any of those described herein. These fasteners may be screws, bolts and nuts, tethers, plugs, posts or other configurations of fastener that would be known to one of skill in the art. Kits may include one or more facet implants, such as any of those described herein.

Kits may include drills or drill bits for creating lumens in the articular processes of a facet joint. The kits may include drills or drill bits for creating lumens in the spinous process. Kits may include drills or drill bits for creating a fastener lumen in bone. The kits may include tools for preparing the facet joint surface. Kits may include one or more tools for implantation.

Methods of use may include any of the following steps. Method steps may include: using an implant deployed to restore the space between facets of a superior articular process of a first vertebra and an inferior articular process of an adjacent vertebra; forming a lumen in a superior articular process of a vertebra; forming a lumen in a inferior articular process of a vertebra; forming a lumen in a second superior articular process of a vertebra; forming a lumen in a second inferior articular process of a vertebra; and/or preparing the surface of the facet for fusion.

Method steps may include: placing a facet reinforcement device on an outer surface of the superior vertebra; placing the first securing portion on the inferior articular process; and/or placing second securing portion on outer surface of the spinous process.

Method steps may include: fusing the vertebra with a fastener member; positioning the fastener member in a first securing portion; inserting the fastener member into a lumen of a first securing portion; inserting the fastener member into the lumen of an inferior articular process of a vertebra; advancing the fastener member; and/or inserting the fastener member into the lumen of a superior articular process of a vertebra.

Method steps may include: securing the fastener member; inserting an end of the fastener member into a fastening mechanism; advancing the fastener member through the fastening mechanism; retaining the facet reinforcement device; and/or retaining the first securing portion.

Method steps may include: forming a lumen in the spinous process; positioning a fastener member in a second securing portion; positioning a fastener in a second securing portion; positioning a fastener in a second securing portion that passes tranlaminally; and/or positioning a fastener between the second securing portion of a first facet reinforcement device and the second securing portion of a second facet reinforcement device.

Method steps may include: preparing a facet joint; positioning a facet reinforcement device, placing a fastener member through a facet reinforcement device; placing a fastener member through a first articular process of a facet joint; placing a fastener member through a second articular process of the facet joint; and/or securing the fastener member over the facet reinforcement device. The positioning of the facet reinforcement device may be performed prior to preparing the facet joint or after preparing the facet joint. The step of preparing the facet joint may involve drilling a lumen through both articular processes of the facet joint. The step of preparing the facet joint may involve roughening up, drilling, burring, or otherwise preparing the articular surfaces of the facet joint.

The method may include passing the fastener member through an aperture in an implant. The method may include any of the following steps from the following order: placing a fastener member through the facet reinforcement device; then placing the fastener member through a first articular process of a facet joint; then placing the fastener member through an implant; then placing the fastener member through a second articular process of the facet joint.

The method may include securing the fastener member. The method may include passing an end of the fastener member through a fastening mechanism; inserting the proximal end portion of the fastener member 1480 into a fastening mechanism 1484; the fastener mechanism located at a distal end portion of the fastener member 1480; securing an end of the fastener member 1480 to the opposite end of the fastener member 1480; securing the proximal end portion of the fastener member 1480 to the distal end portion of the fastener member 1480; and/or advancing the proximal end portion of the fastener member 1480 through the fastening mechanism 1484. The method may include tying a first portion the fastener member to a second portion of the fastener member; forming a knot in a first end and second end; screwing the fastener member into a threaded central lumen; threading a fastener onto a threaded end of a fastener member disposed through a threaded central lumen; and/or including enlarged portions at the end of the fastener member. The method may include using the fastener member to secure the facet reinforcement device; and/or using the fastener member to secure the facet first securing portion.

The method may include securing the fastener. The method may include passing an end of the fastener through the second securing portion; passing an end of the fastener through the second securing portion of a first facet reinforcement device; and/or passing an end of the fastener through the second securing portion of a second facet reinforcement device. The step of positioning the facet reinforcement device may be followed by the step of using a fastener. The method may include using a fastener to secure the facet reinforcement device to a vertebral structure. This vertebral structure may be a spinous process, the base of a spinous process, or other posterior structure. The step of using a fastener may include placing one or more fasteners.

The method may include repeating steps to place a second facet reinforcement device at the contralateral facet joint. The method may include repeating steps to place a second facet reinforcement device at another facet joint. The method may include repeating steps to place a second facet reinforcement device at another vertebral level. The method may include using a fastener to secure the facet reinforcement device to a vertebral structure. The method may include by placing one or more fasteners through a lumen in the first facet reinforcement device and through a lumen in the second facet reinforcement device. The fastener may be placed through a vertebral structure. The fastener may be placed through a spinous process. The fastener may be secured with a nut or other securing element. The fastener may be threaded into a lumen in the first facet reinforcement device and/or a lumen in the second facet reinforcement device.

In the above embodiments, it should be understood that fastener member similar to any of those described above, for example, at 72, 280, 380, 480, 580, 680, 780, and 880, may be used with any of the embodiments of the facet reinforcement device described herein. Furthermore, the facet reinforcement devices may be used with various of the facet implants described herein, such as those with a wire or cable retaining device. Though the facet reinforcement devices are primarily described in relation to reinforcing the inferior articular process, it is to be understood that embodiments may also be used to reinforce the superior articular process. For example, for use on a surface of a superior facet, embodiments of a facet reinforcement device similar to 1500 may be shaped and sized such that the second securing portion 1540 meets the vertebra. The facet reinforcement device 1500 could permit placement of one or more fasteners 1590 through, for example, the pedicle or into the vertebral body.

Similarly, through the illustrations of the facet reinforcement device show the facet reinforcement device applied to lumbar vertebrae, it will be understood that multiple sizes and shapes may be provided adapted for placement on facet surfaces in the cervical or thoracic region.

The terms "generally" "approximately", "about", and "substantially" as used herein represent an amount or characteristic close to the stated amount or characteristic that still performs a desired function or achieves a desired result. For example, the terms "approximately", "generally" "about", and "substantially" may refer to an amount that is within less than 10% of, within less than 5% of, within less than 1% of, within less than 0.1% of, and within less than 0.01% of the stated amount or characteristic.

The term "up to about" as used herein has its ordinary meaning as known to those skilled in the art and may include 0 wt. %, minimum or trace wt. %, the given wt. %, and all wt. % in between.

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A kit for treating a spine, comprising:
a fastener member comprising a proximal end portion and a distal end portion, the distal end portion comprising a fastening mechanism configured to accept the proximal end portion forming a loop;
an implant configured to be inserted between a superior articular process and an inferior articular process, wherein the implant is configured to be retained within the loop of the fastener member; and
a facet reinforcement device comprising a proximal surface, a distal surface, and a lumen disposed between the proximal and distal surface, the lumen adapted for receiving the fastener member, wherein the facet reinforcement device is configured to be retained within the loop of the fastener member, wherein the facet reinforcement device is configured to be disposed on an outer facing surface of the superior articular process or an outer facing surface of the inferior articular process, wherein the facet reinforcement device comprises a roughened surface, wherein the proximal surface of the facet reinforcement device comprises a recess to mechanically interfit with a portion of the fastener member.

2. The kit of claim 1, wherein the distal surface of the facet reinforcement device comprises the roughened surface to engage a bony surface of a facet.

3. The kit of claim 1, wherein the roughened surface of the facet reinforcement device comprises at least one projection, the projection extends from the distal surface and includes a sharp tip.

4. The kit of claim 1, wherein the facet reinforcement device further comprises a second securing segment comprising a proximal surface, a distal surface, and at least one lumen.

5. The kit of claim 4, wherein the second securing segment of the facet reinforcement device is adapted to attach to a spinous process.

6. The kit of claim 4, wherein the second securing segment of the facet reinforcement device is adapted to attach to a lamina.

7. The kit of claim 4, wherein the second securing segment of the facet reinforcement device comprises two lumens.

8. The kit of claim 4, further comprising:
a fastener configured for securing the second securing segment of the facet reinforcement device to the vertebra.

9. The kit of claim 1, wherein the fastening mechanism is configured to allow the proximal end portion to travel through the distal end portion in only one direction.

10. The kit of claim 1, wherein the roughened surface of the facet reinforcement device comprises a plurality of spikes.

11. The kit of claim 1, wherein the roughened surface of the facet reinforcement device comprises at least one projection, wherein the projection is porous.

12. The kit of claim 1, wherein the facet reinforcement device comprises a feature to mechanically interfit with an insertion tool, wherein the kit comprises the insertion tool.

13. The kit of claim 12, wherein the feature is located on the proximal surface and wherein the distal surface of the facet reinforcement device comprises the roughened surface.

14. The kit of claim 1, wherein the roughened surface comprises at least one spike, barb, wedge, or hook projecting from at least a portion of one surface of the facet reinforcement device.

15. A kit for treating a spine, comprising:
a fastener member comprising a proximal end portion and a distal end portion, the distal end portion comprising a fastening mechanism configured to accept the proximal end portion, wherein the fastening mechanism is configured to allow the proximal end portion to travel through the distal end portion in only one direction;
an implant having an interface configured for receiving the fastener member; and
a facet reinforcement device configured to be disposed on an outer facing surface of a facet, the facet reinforcement device comprising a proximal surface, a distal surface, and a lumen disposed between the proximal and distal surface, the lumen adapted for receiving the fastener member, wherein at least a portion of the facet reinforcement device is malleable to conform to the shape of the facet, wherein the proximal surface comprises a first material and the distal surface comprises a second material, different than the first material.

16. The kit of claim 15, wherein the distal surface of the facet reinforcement device comprises a plurality of projections.

17. The kit of claim 15, wherein the facet reinforcement device is porous.

18. The kit of claim 15, further comprising an adhesive configured to bond the distal surface to the surface of the facet.

19. A kit for treating a spine, comprising:
an implant with a first face and a second face adapted to contact the bony or cartilaginous articular surfaces of the facets of adjacent vertebrae, wherein the implant has at least a plurality of apertures extending from the first face to the second face; and
a fastener member comprising a proximal end portion and a distal end portion, the fastener member configured for generally maintaining the location of the implant with respect to the facet joint, the fastener member configured to extend through the aperture in the implant,
a first enlarged structure adapted to engage an outer surface of a facet of the facet joint, wherein the first enlarged structure has a cylindrical abluminal surface and a centrally located lumen,
wherein the kit has a first configuration wherein the first enlarged structure is movable along the fastener member, and a second configuration wherein the first enlarged structure is substantially fixed relative to the flexible member and the first enlarged structure is mechanically interfit with the fastener member to increase stability of the first enlarged structure and the fastener member;
wherein the fastener member is configured to allow the proximal end portion to travel through the distal end portion in only one direction to transition from the first configuration to the second configuration.

* * * * *

UNITED STATES PATENT AND TRADEMARK OFFICE
CERTIFICATE OF CORRECTION

PATENT NO. : 9,839,450 B2
APPLICATION NO. : 14/274575
DATED : December 12, 2017
INVENTOR(S) : Jason Blain Page 1 of 1

It is certified that error appears in the above-identified patent and that said Letters Patent is hereby corrected as shown below:

In the Specification

Column 14 Line 37, Change "IAP" to --IAP1A--.

Column 14 Line 50, Change "IAP" to --IAP1A--.

Column 14 Line 56, Change "IAP" to --IAP1A--.

Column 16 Line 19, Change "IAP" to --IAP1A--.

Column 16 Line 24, Change "IAP" to --IAP1A--.

Column 17 Line 55, Change "XXIII" to --XXIII.--.

Column 23 Line 48, Change "IAP" to --IAP1A--.

Column 23 Line 53, Change "IAP" to --IAP1A--.

Column 23 Line 66, Change "IAP" to --IAP1A--.

Column 28 Line 35, Change "IAP" to --IAP1A--.

Column 30 Line 60, Change "IAP" to --IAP1A--.

Column 31 Line 19, Change "IAP" to --IAP1A--.

Signed and Sealed this
Twenty-fourth Day of April, 2018

Andrei Iancu
*Director of the United States Patent and Trademark Office*